US011406035B2

(12) United States Patent
van Pol et al.

(10) Patent No.: US 11,406,035 B2
(45) Date of Patent: *Aug. 2, 2022

(54) SENSOR DEVICE, SYSTEMS, AND METHODS FOR IDENTIFYING LEAKS IN A FLUID CONDUIT

(71) Applicant: INGU Solutions Inc., Calgary (CA)

(72) Inventors: Johannes Hubertus Gerardus van Pol, Calgary (CA); Anouk van Pol, Calgary (CA); Huibert Aren Bogerman, Ees (NL)

(73) Assignee: INGU Solutions Inc., Calgary (CA)

( * ) Notice: Subject to any disclaimer, the term of this patent is extended or adjusted under 35 U.S.C. 154(b) by 126 days.

This patent is subject to a terminal disclaimer.

(21) Appl. No.: 15/843,310

(22) Filed: Dec. 15, 2017

(65) Prior Publication Data

US 2018/0171783 A1 Jun. 21, 2018

Related U.S. Application Data

(60) Provisional application No. 62/434,860, filed on Dec. 15, 2016.

(51) Int. Cl.
*G01N 29/02* (2006.01)
*H05K 5/06* (2006.01)
(Continued)

(52) U.S. Cl.
CPC .............. *H05K 5/06* (2013.01); *E21B 47/117* (2020.05); *F16L 55/40* (2013.01); *G01D 11/245* (2013.01);
(Continued)

(58) Field of Classification Search
CPC ..................................................... G01N 29/02
(Continued)

(56) References Cited

U.S. PATENT DOCUMENTS 3,720,797 A 3/1973 Gunn et al.
3,732,434 A 5/1973 French
(Continued)

FOREIGN PATENT DOCUMENTS

EP 1962089 8/2008
WO 200170422 9/2001
(Continued)

OTHER PUBLICATIONS

European Patent Office, Partial European Search Report for EP Patent App. No. 17020577.7, dated May 2, 2018.
European Patent Office, Partial European Search Report for EP Patent App. No. 17020578.5, dated May 2, 2018.
Ingu Solutions, Specifications document for Xploring WiseMotesTM, downloaded from www.Ingu-solutions.com.

*Primary Examiner* — John Fitzgerald
*Assistant Examiner* — Rodney T Frank
(74) *Attorney, Agent, or Firm* — Own Innovation; James W. Hinton

(57) ABSTRACT

Provided is a method, system, and sensor device for identifying and detecting presence of a leak in a fluid conduit. The sensor device freely flows with a fluid within the fluid conduit. The sensor device includes an outer capsule that is free flowing within the fluid and provides fluid-tight containment to an interior compartment, at least one acoustic sensor mounted within the interior compartment, wherein the at least one acoustic sensor senses acoustic properties of the fluid to detect the presence of the leak, and a conductor for activating the at least one acoustic sensor to sense the acoustic properties of the fluid and the fluid conduit, wherein the conductor passes from the interior compartment and through to the outer capsule.

13 Claims, 53 Drawing Sheets

(51) Int. Cl.
*G01D 11/24* (2006.01)
*G01M 3/24* (2006.01)
*G01N 33/18* (2006.01)
*F16L 55/40* (2006.01)
*G01L 19/14* (2006.01)
*E21B 47/117* (2012.01)
*G01F 1/684* (2006.01)
*H05K 5/02* (2006.01)
*F16L 101/30* (2006.01)
*G01N 33/28* (2006.01)
*G01F 1/34* (2006.01)
*G01K 13/02* (2021.01)

(52) U.S. Cl.
CPC ............ *G01F 1/684* (2013.01); *G01L 19/149* (2013.01); *G01M 3/246* (2013.01); *G01N 29/02* (2013.01); *G01N 33/1886* (2013.01); *H05K 5/0247* (2013.01); *F16L 2101/30* (2013.01); *G01F 1/34* (2013.01); *G01K 13/02* (2013.01); *G01N 33/18* (2013.01); *G01N 33/28* (2013.01)

(58) Field of Classification Search
USPC ....................................................... 73/152.29
See application file for complete search history.

(56) References Cited

U.S. PATENT DOCUMENTS

| | | | |
|---|---|---|---|
| 8,098,063 | B2 | 1/2012 | Paulson |
| 2005/0113853 | A1 | 5/2005 | Noriega et al. |
| 2007/0117392 | A1 | 5/2007 | Smith et al. |
| 2008/0204008 | A1* | 8/2008 | Paulson ............... F17D 1/08 324/220 |
| 2008/0252254 | A1 | 10/2008 | Osada |
| 2010/0223988 | A1 | 9/2010 | Crow et al. |
| 2011/0253373 | A1* | 10/2011 | Kumar ............... E21B 23/10 166/306 |
| 2012/0312078 | A1 | 12/2012 | Bakhtiar |
| 2015/0113853 | A1 | 4/2015 | McKeough et al. |
| 2015/0155920 | A1 | 6/2015 | Talnishnikh et al. |
| 2015/0268213 | A1 | 9/2015 | Wortche et al. |
| 2015/0285059 | A1 | 10/2015 | Wortche et al. |
| 2018/0177064 | A1* | 6/2018 | van Pol ............... H05K 5/0247 |

FOREIGN PATENT DOCUMENTS

| | | | |
|---|---|---|---|
| WO | 2003100153 | 12/2003 | |
| WO | WO-2004059274 A2 * | 7/2004 | ............ G01M 3/246 |
| WO | 2006081671 | 8/2006 | |
| WO | 2008149092 | 12/2008 | |

* cited by examiner

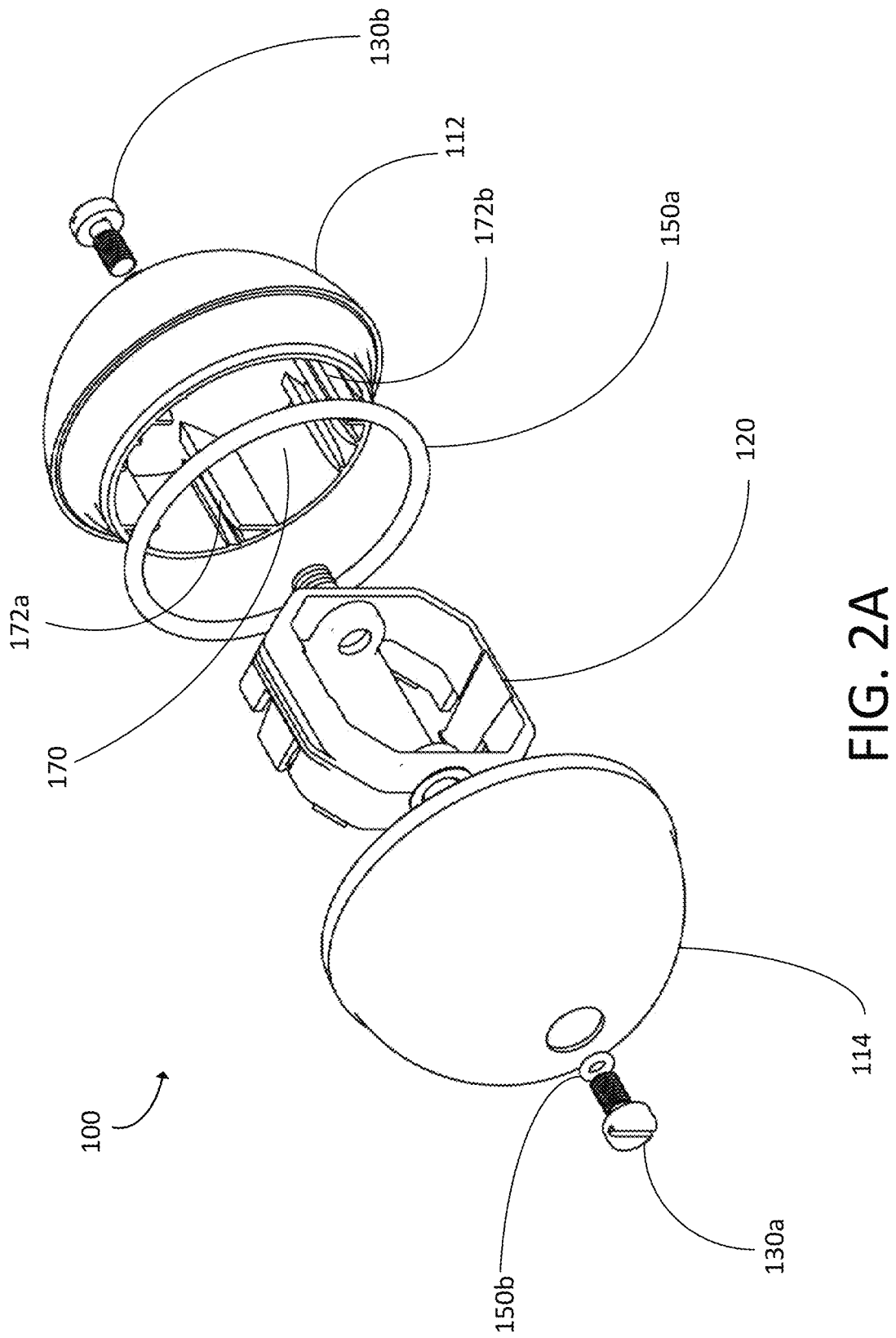

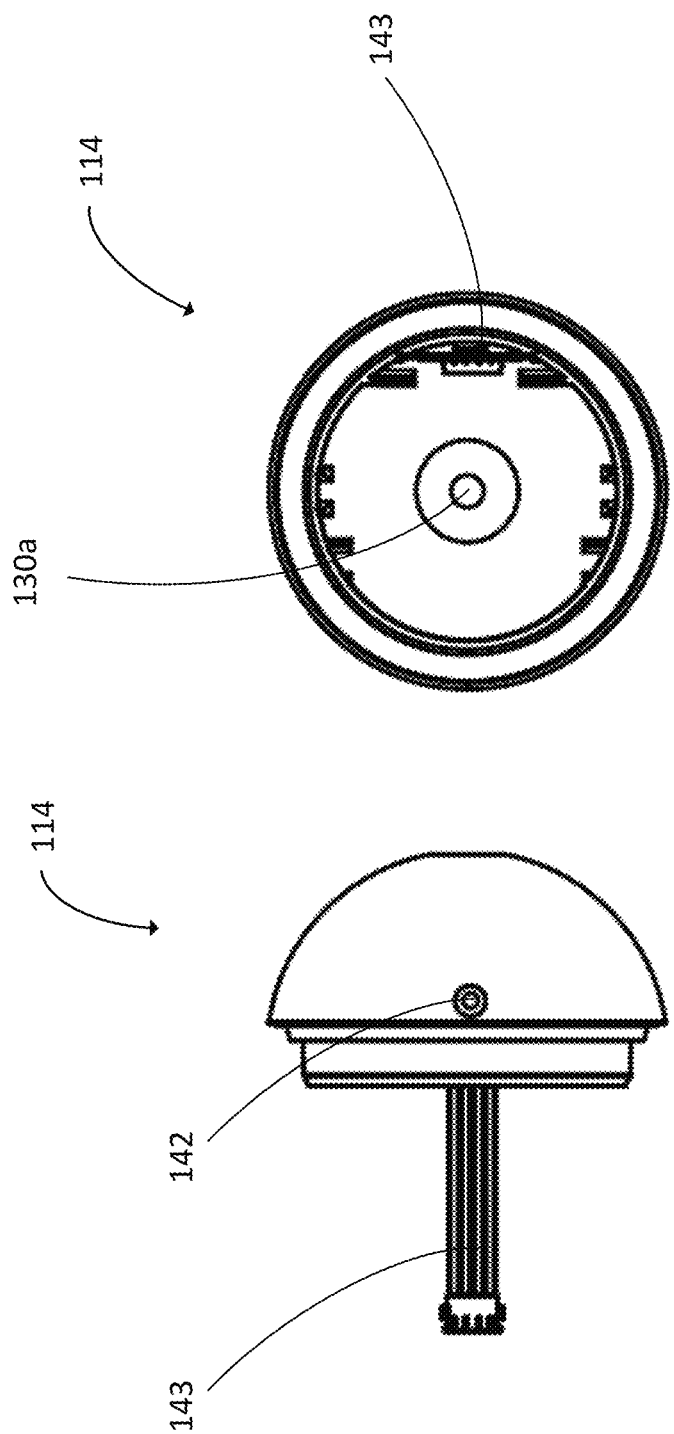

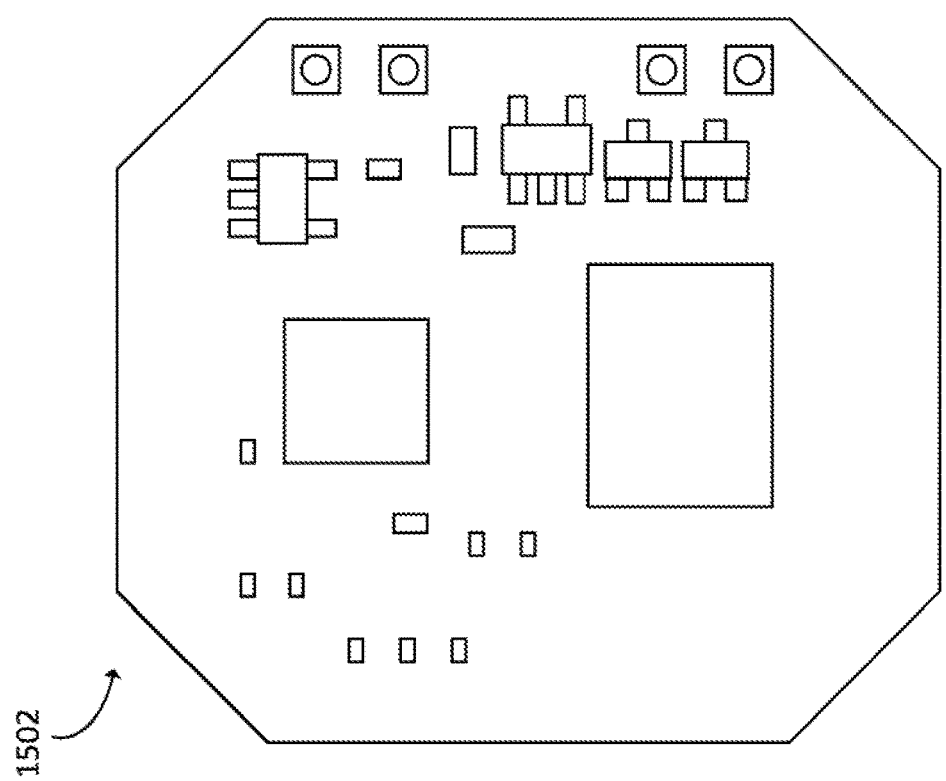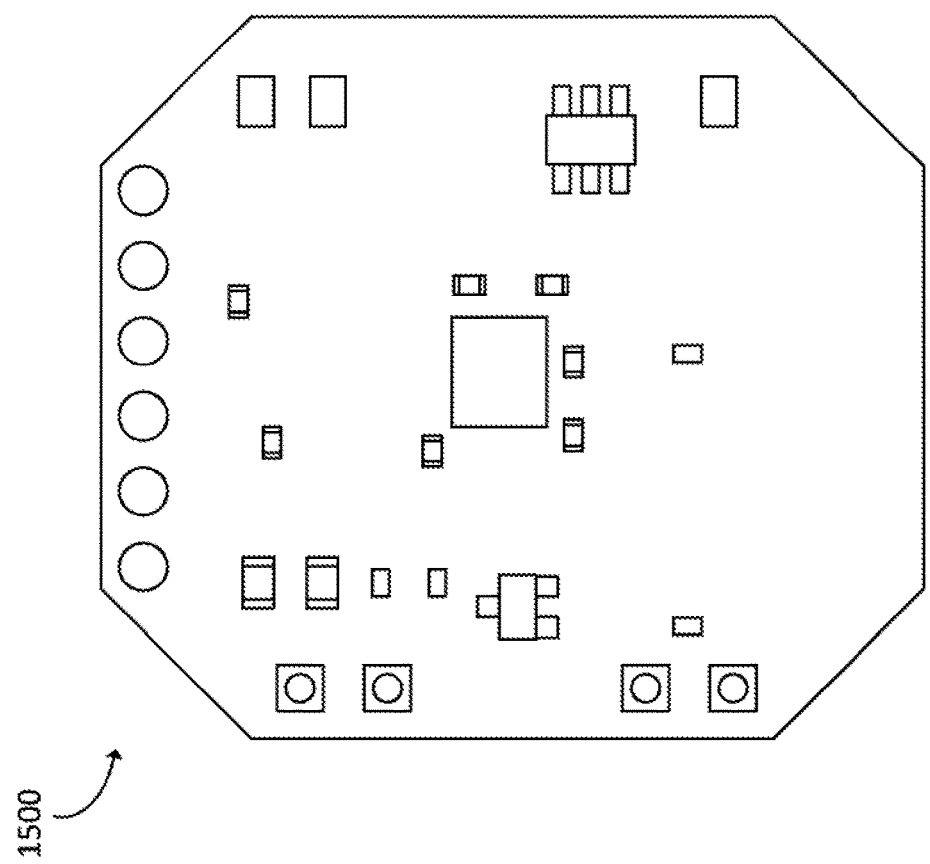
FIG. 3D

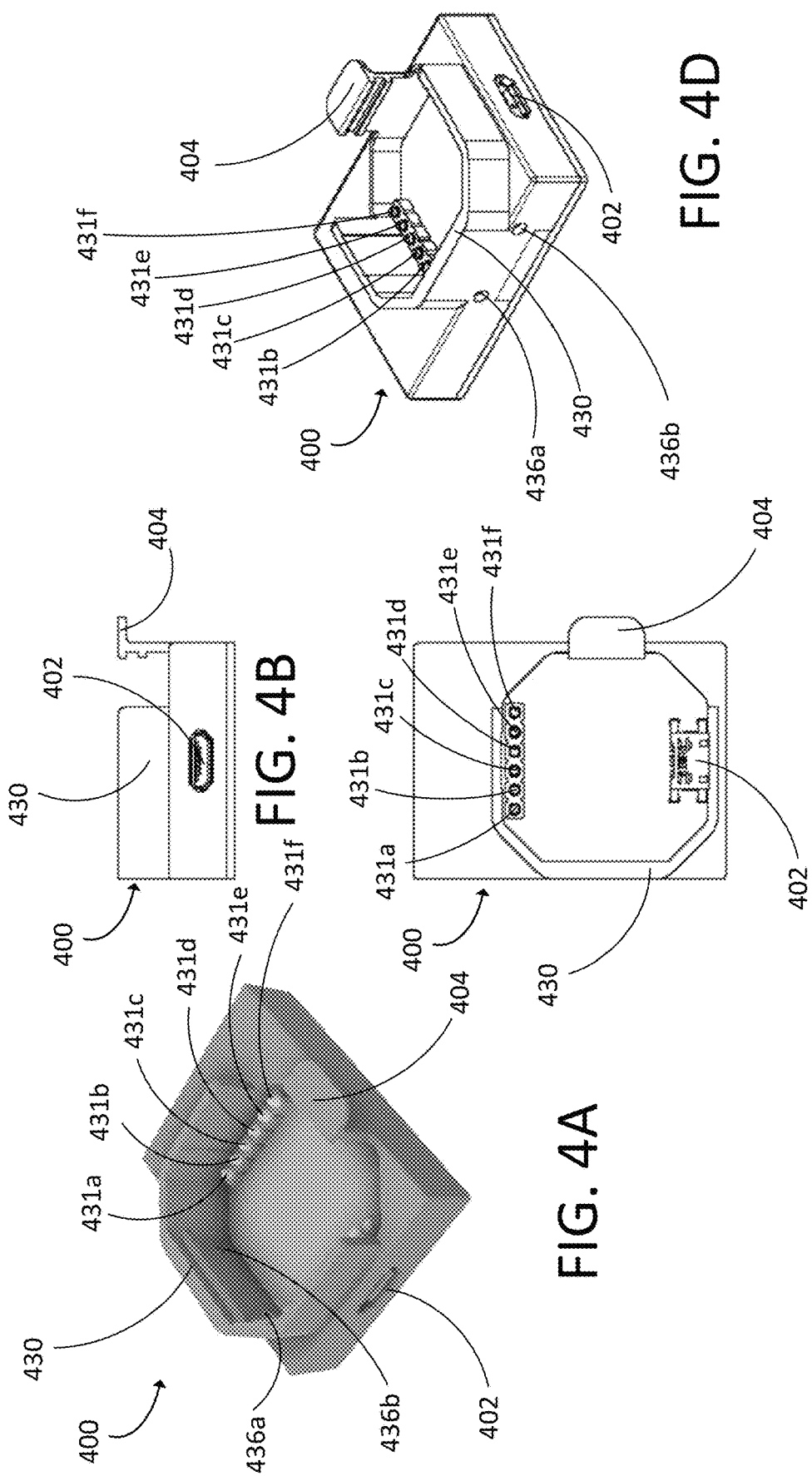

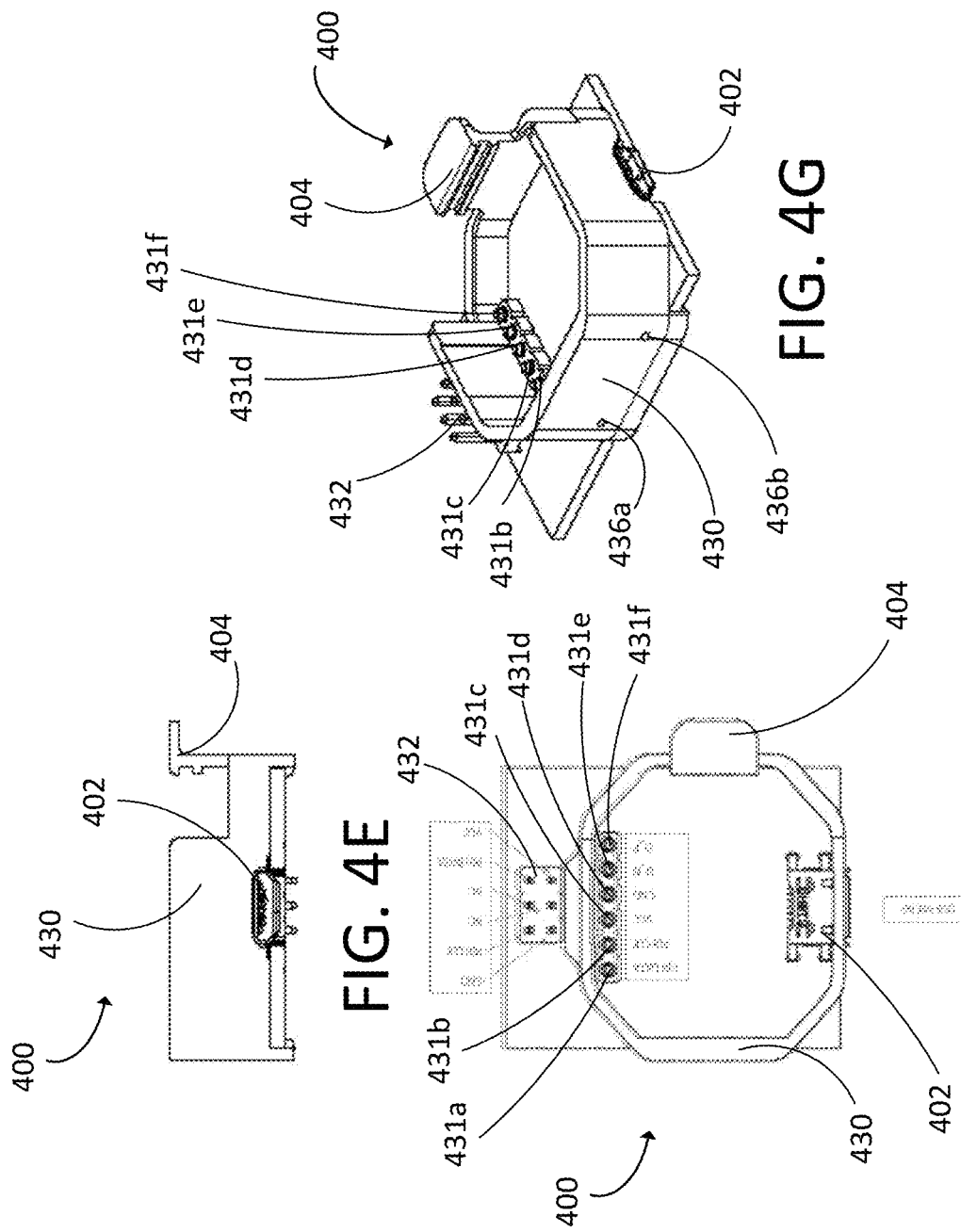

SENSOR DEVICE, SYSTEMS, AND METHODS FOR IDENTIFYING LEAKS IN A FLUID CONDUIT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The embodiments disclosed herein relate to sensing and data collection, and, in particular, to an apparatus, systems, and methods for collecting fluid data, in both liquid and gas phases, and identifying a leak in a fluid conduit data.

INTRODUCTION

A sensor device such as a sensor mote typically refers to a relatively small sensor with its own energy storage. Conventionally, the sensor mote is part of a wireless network via which the sensed environmental parameter is communicated to a remote computer. A motes-system includes a plurality of sensor motes which together form a plurality of sensors for sensing the environmental parameter. Such motes-systems may be used in many diverse applications, from earthquake measurements to warfare.

Conventionally, the motes include a controller, transceiver, power source and one or more sensors. One example of environmental monitoring can be found in the NASA sensor web. This network comprises spatially distributed sensors that wirelessly communicate with each other. In this network, every mote sends out collected data to every other mote, so substantially every mote knows what is happening in the network. Alternatively, sensor networks may be configured to use GPS communication and/or may be configured to handle large data sets.

Using such known sensor networks for environmental mapping or monitoring, the position of the individual motes should be known which requires extensive communication with the outside world, for example, via a Global Positioning System (further also indicated as GPS). However, in some remote environments, such as, for example, oil wells, pipelines, or sewer systems in cities, the GPS signal does not reach the individual motes and other ways of measuring the environment parameter have to be found.

United States Patent Application Publication No. 2015/0268213 to Wörtche et al. (hereinafter '213) describes a mote having a maximum outer dimension of less than 10 millimeters. '213 describes a mote having a wireless antenna for communicating with an external device, which may present an upper limit as to how many motes can be interfaced with at any particular time. Reliability of transmission may also be an issue, especially where a large number of motes are used. A mote having a maximum outer dimension of less than 10 millimeters may preclude certain kinds of components from being used and may also affect repairability. A mote of less than 10 millimeters may also be more likely to get caught in certain crevices in the path of the fluid flow.

Accordingly, there is a need for an improved sensor device, systems, and methods for determining fluid parameters as described herein.

SUMMARY

In an aspect, there is a sensor device for detecting presence of a leak in a fluid conduit. The sensor device flowing with a fluid within the fluid conduit. The sensor device includes an outer capsule that is free flowing within the fluid and provides fluid-tight containment to an interior compartment; at least one acoustic sensor mounted within the interior compartment, wherein the at least one acoustic sensor senses acoustic properties of the fluid to detect the presence of the leak; and a conductor for activating the at least one acoustic sensor to sense the acoustic properties of the fluid and the fluid conduit, wherein the conductor passes from the interior compartment and through to the outer capsule.

The at least one acoustic sensor may include a piezo transducer for converting vibrations of the outer capsule into electrical signals representing the sensed acoustic properties of the fluid.

The outer capsule may include a first capsule portion and a second capsule portion that enclose the interior compartment and that can be separated to provide access to the interior compartment.

The conductor may include a fastener to close the first capsule portion with the second capsule portion.

The sensor device may further include a memory within the interior compartment for storing the sensed fluid properties; and a power source within the interior compartment for providing power to the at least one acoustic sensor and the memory.

The sensor device may further include an inner frame for supporting the at least one acoustic sensor, the memory, and the power source within the interior chamber.

The sensor device may further include at least one of a pressure sensor, a temperature sensor, an ultrasonic sensor, an accelerometer, a gyroscope and a magnetometer for sensing other fluid properties.

The sensor device may further include at least one indicator light mounted within the interior compartment, the at least one indicator light for indicating the status of the sensor device, and wherein the first capsule portion is transparent such that the at least one indicator light is visible.

In an aspect there is a system for determining presence of a leak in a fluid conduit. The system includes a sensor device for freely flowing with the fluid within the fluid conduit to sense acoustic properties of the fluid, the sensor device having at least one acoustic sensor for sensing the acoustic properties of the fluid, the sensor device having a memory for storing the sensed acoustic properties as at least one audio recording; and an external electrical connector for connecting to the memory, the external electrical connector for providing the at least one audio recording to a computer system.

The memory (for example a micro-SD card) may be removable, and the dedicated memory may be connected (for example via a SD card reader) to a computer for read out.

The acoustic sensor of the sensor device may include a piezo transducer for converting vibrations imposed on the piezo transducer by the fluid to electrical signals representing the sensed acoustic properties of the fluid.

The system may further include the fluid conduit, wherein the fluid conduit comprises a plurality of different sections, the acoustic properties of the fluid within the plurality of different sections substantially corresponding to a plurality of recognizable section-specific audio signatures, the acoustic properties of the fluid within each section of the plurality of different sections substantially corresponding to at least one recognizable section-specific audio signature of the plurality of recognizable section-specific audio signatures, the at least one recognizable section-specific audio signature being identifiable from the at least one audio recording.

The plurality of different sections may include any one or more of a launching section, a straight section, a bend section, a welded section, a flange section, a valve section, a regulator section, an actuator section, a rising section, a falling section, and a receiving section.

The computer system may dissect the provided at least one audio recording into categorized and uncategorized regions, the categorized regions including the plurality of recognizable section-specific audio signatures, the uncategorized regions having at least one uncategorized audio signature not similar to the plurality of recognizable section-specific audio signatures, each uncategorized regions having at least one neighboring categorized region.

The computer system may determine the presence of the leak within the fluid conduit by comparing the at least one uncategorized audio signature of the uncategorized regions to the at least one recognizable section-specific audio signature of the at least one neighboring categorized region.

The comparison of the at least one uncategorized audio signature of the uncategorized regions to the at least one recognizable section-specific audio signature of the at least one neighboring categorized region by the computer system may include determining any one or more of presence of intense spikes, density of intense spikes and presence of irregular patterns.

The human operator may determine the presence of the leak in the fluid conduit by listening to the audio.

The at least one audio recording may include a plurality of audio recordings. The computer system may determine the presence of the leak within the fluid conduit by comparing each of the plurality of audio recordings together and may determine the difference between each of the plurality of audio recordings.

In aspect there is a method for determining presence of a leak in a fluid conduit carrying a fluid. The method includes sensing acoustic properties of the fluid with a sensor device that flows freely along a path of the fluid conduit and storing the sensed acoustic properties as a first acoustic dataset; after waiting a period of time, sensing acoustic properties of the fluid with the sensor device along the same path and storing the sensed acoustic properties as a second acoustic dataset; and comparing the first acoustic dataset with the second acoustic dataset to determine the presence of the leak in the fluid conduit.

The method may further include connecting the sensor device to an external device for providing the external device with the first acoustic dataset and the second acoustic dataset and performing the comparison of the first acoustic dataset with the second acoustic dataset for determining the presence of the leak in the fluid conduit on the external device.

The determination of the presence of the leak in the fluid conduit on the external device may include: comparing the first acoustic dataset with the second acoustic dataset; identifying differences between the first acoustic dataset and the second acoustic dataset; determining whether the differences are attributable to the presence of the leak within the fluid conduit by listening to audio recording corresponding to the differences.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings:

FIG. 2A is an exploded view of the sensor device of FIG. 1A, with certain components removed;

FIGS. 2B and 2C are a side view and a bottom view, respectively, of the second capsule portion of the sensor device of FIG. 1A, with an external-facing sensor;

FIG. 3D are front and back photographs of a circuit board for the sensor platform of sensor device of FIG. 1A;

FIGS. 4A, 4B, 4C, and 4D are a perspective view, a side view, a top view, and another perspective view, respectively, of a capsule dock for the sensor device of FIG. 1A, in accordance with an embodiment;

FIGS. 4E, 4F, and 4G are a side view, a top view, and a perspective view, respectively, of a capsule dock for the sensor device of FIG. 1A, with a pin header in accordance with an embodiment;

FIG. 5B is a perspective view of the activator unit of FIG. 5a;

DETAILED DESCRIPTION

Figure 1A:
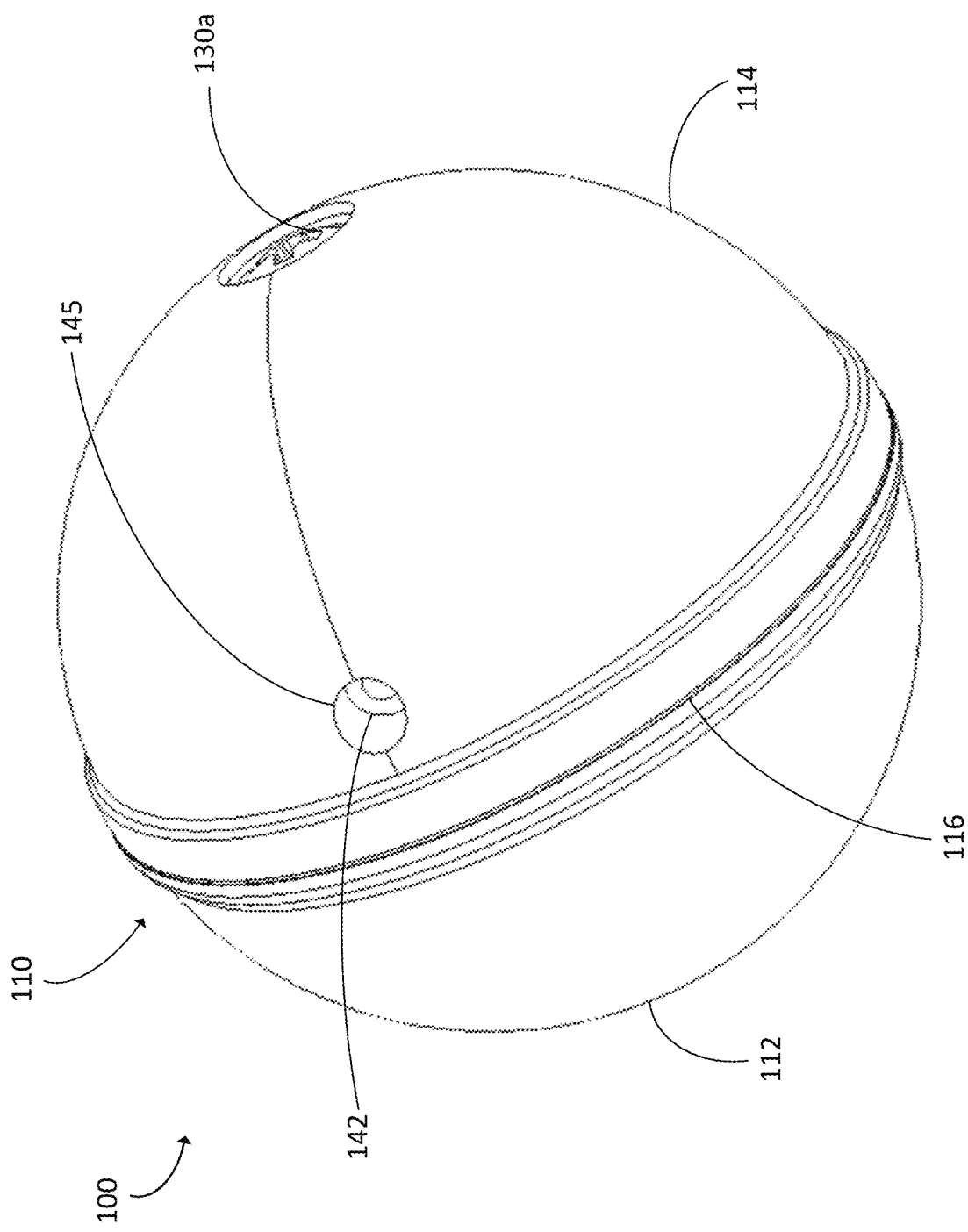
FIG. 1A is a perspective view of a sensor device, in accordance with an embodiment.
Figure 1B:
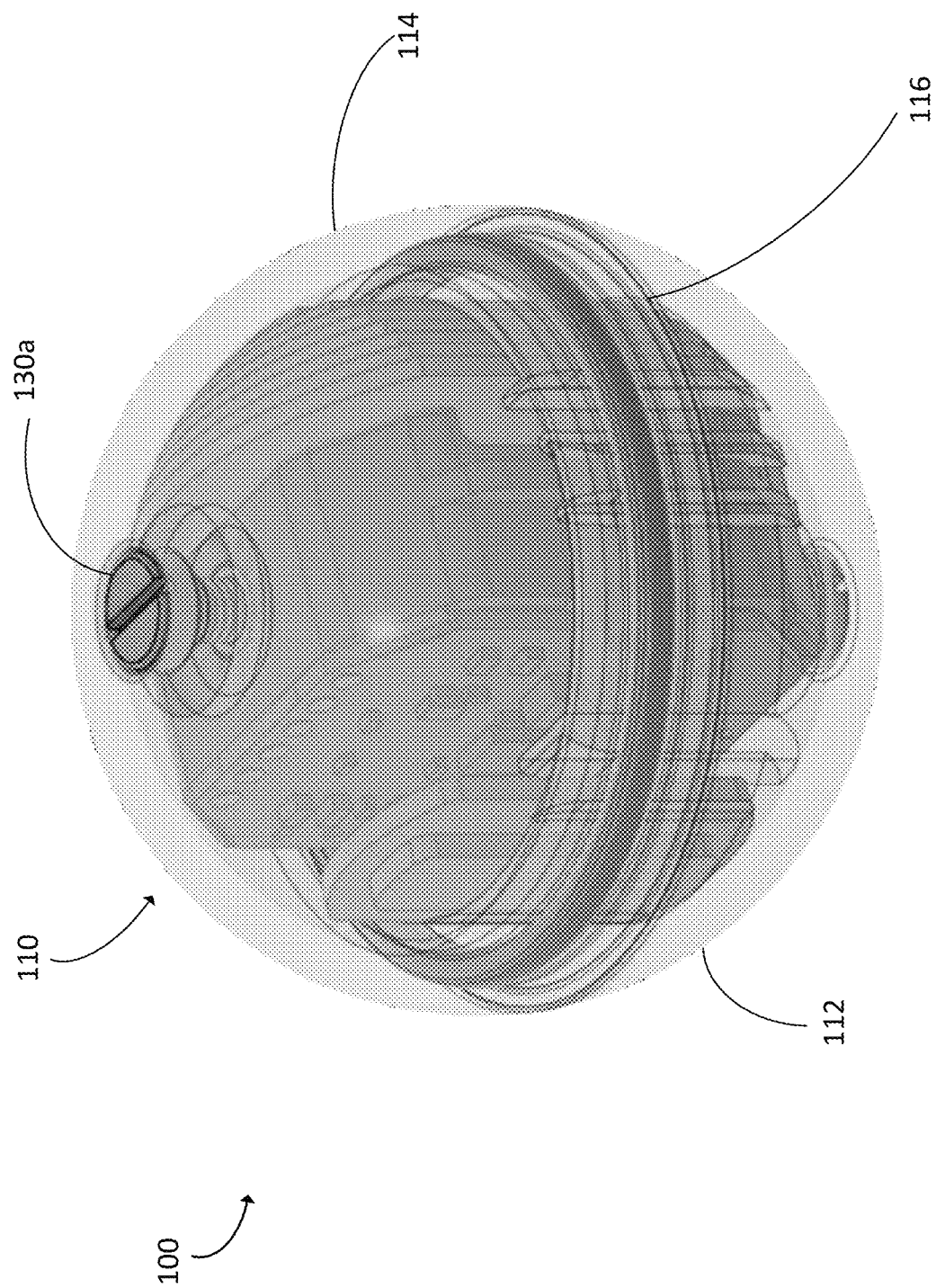
FIG. 1B is a transparent perspective view of the sensor device of FIG. 1A, without a pressure/temperature sensor in an aperture of an outer capsule.
Figure 1C:
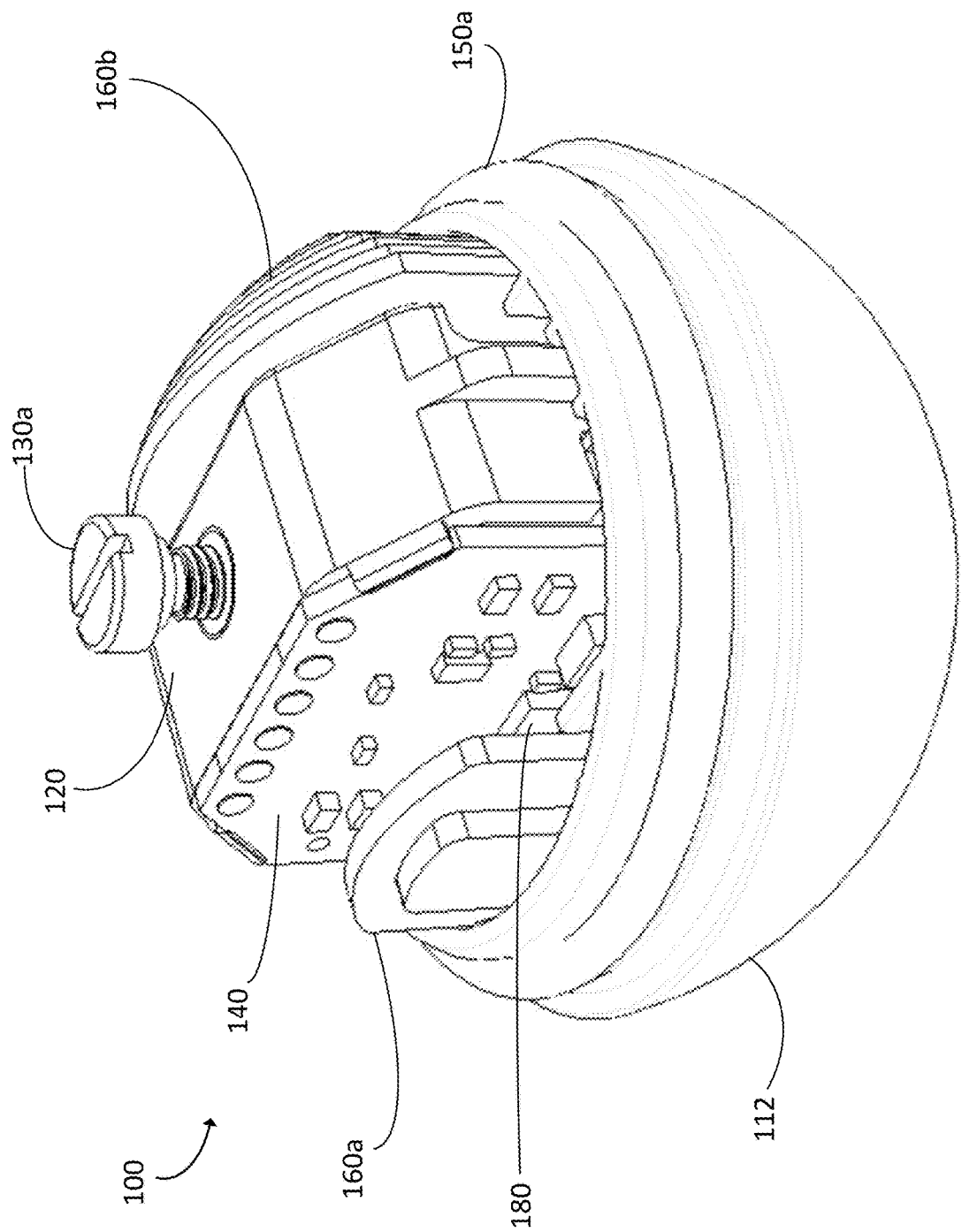
FIG. 1C is a perspective view of the sensor device of FIG. 1A, with an outer portion removed to expose an interior compartment of the sensor device.
Figure 1D:
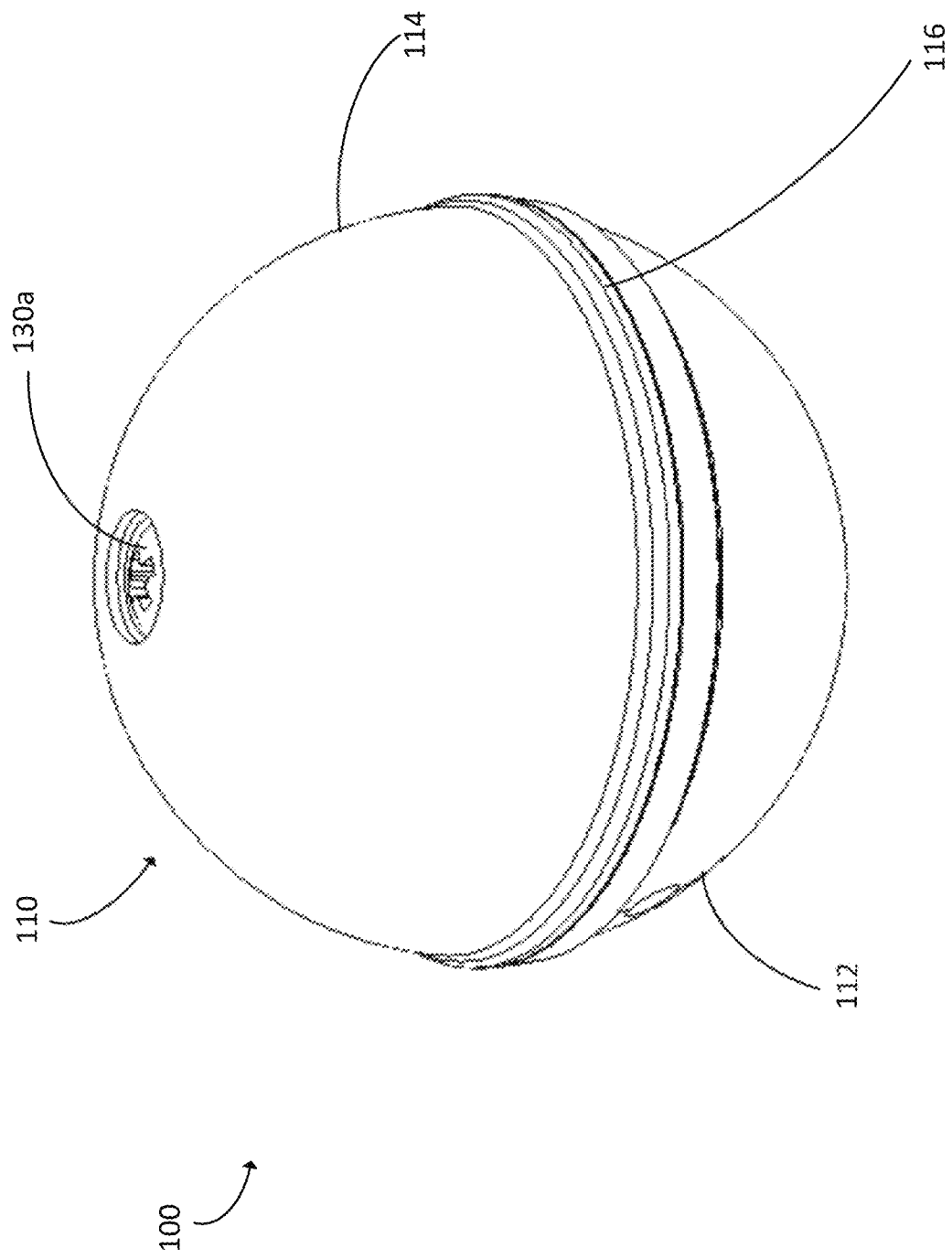
FIG. 1D is a perspective view of the sensor device of FIG. 1A.
Figure 1E:
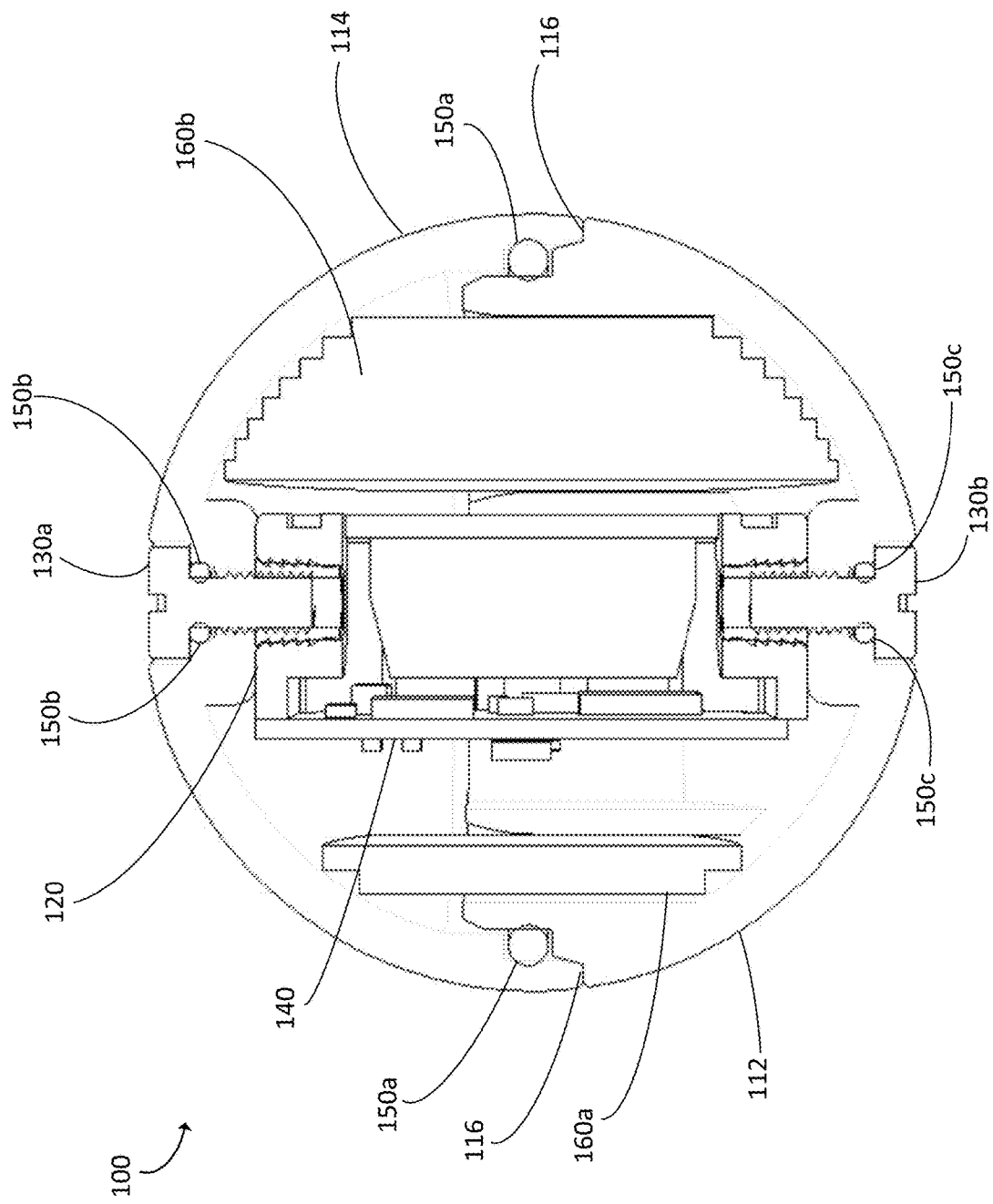
FIG. 1E is a cross-sectional view of the sensor device of FIG. 1A.
Figure 1F:
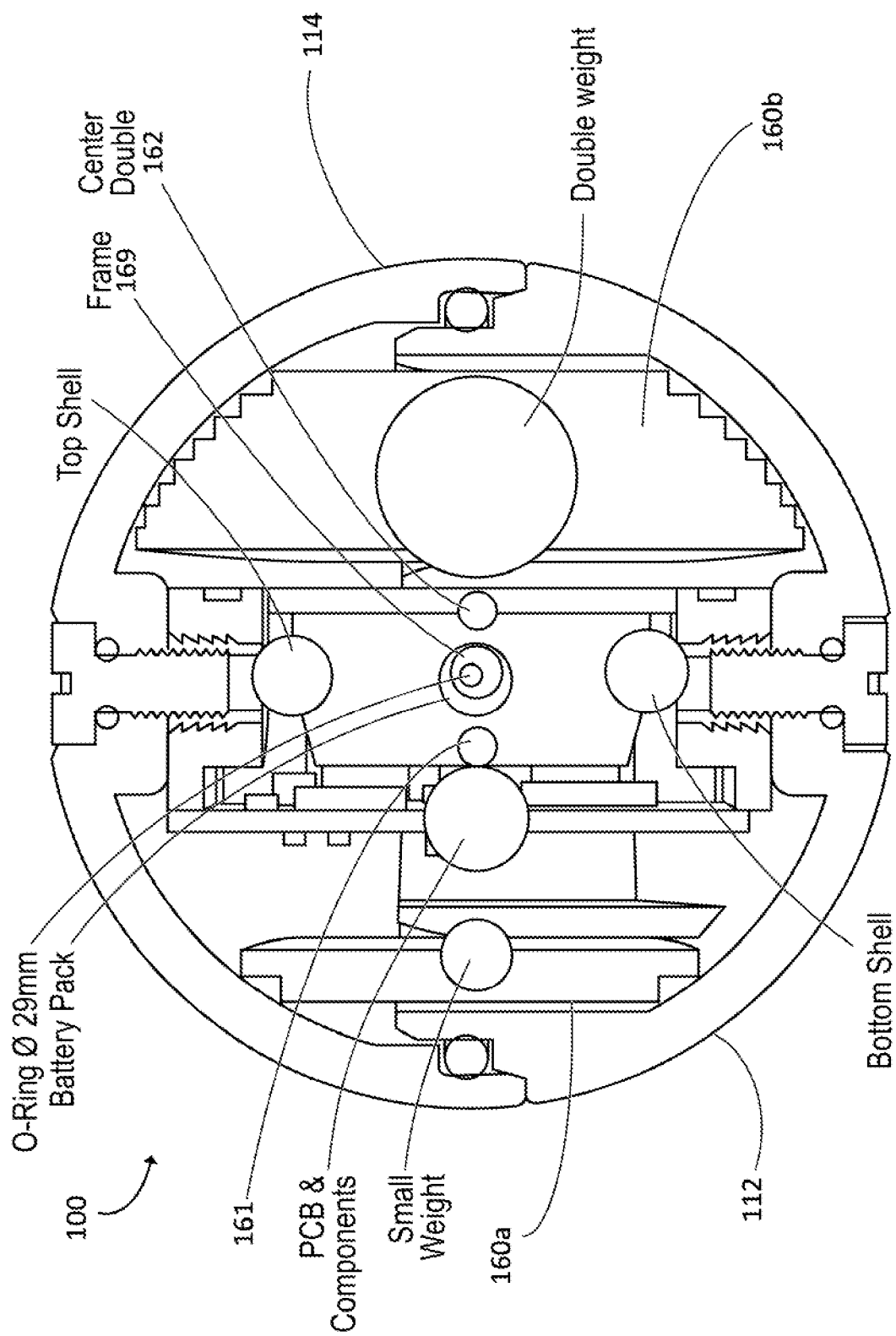
FIG. 1F is a mass distribution diagram of the sensor device of FIG. 1A.
Figure 1G:
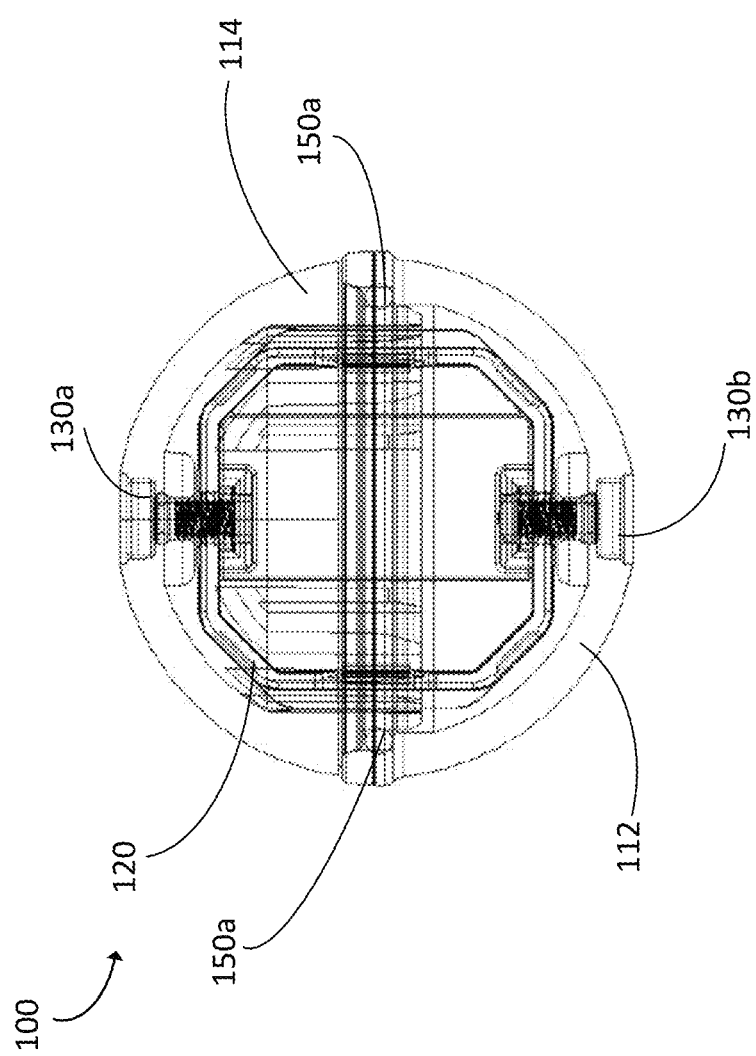
FIGS. 1G, 1H, 1I, and 1J are cross-sectional views of the sensor device of FIG. 1A.
Figure 1I:
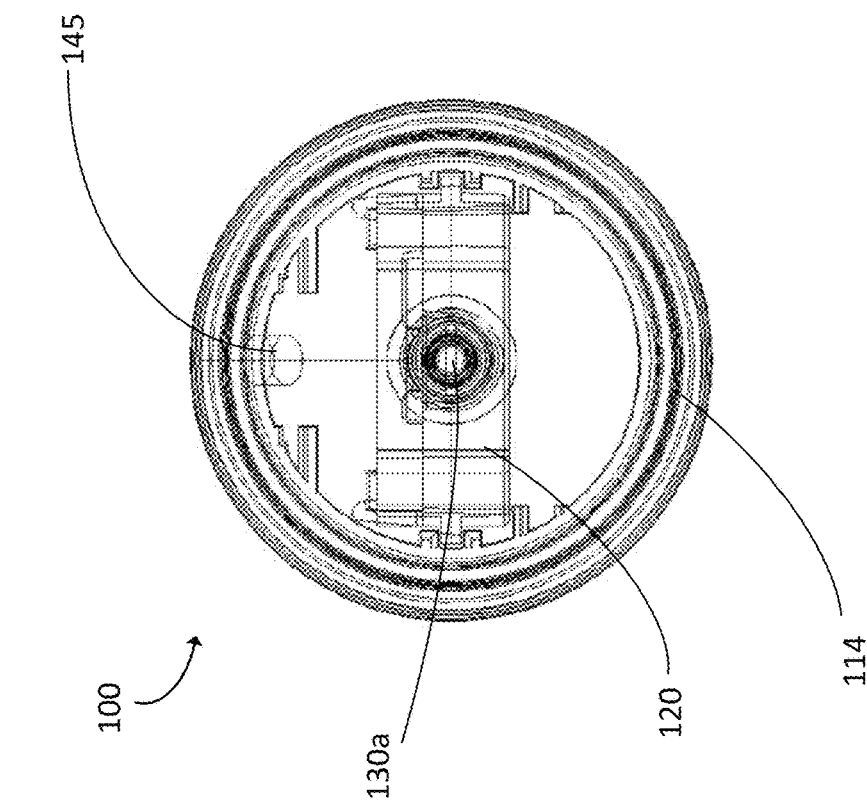
Figure 1H:
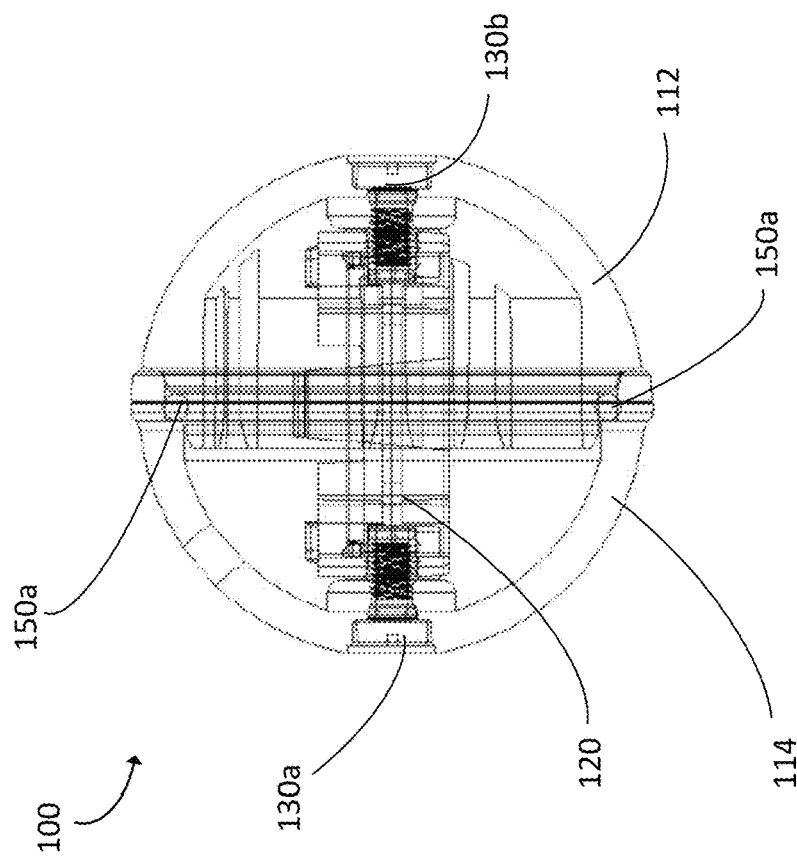
Figure 1J:
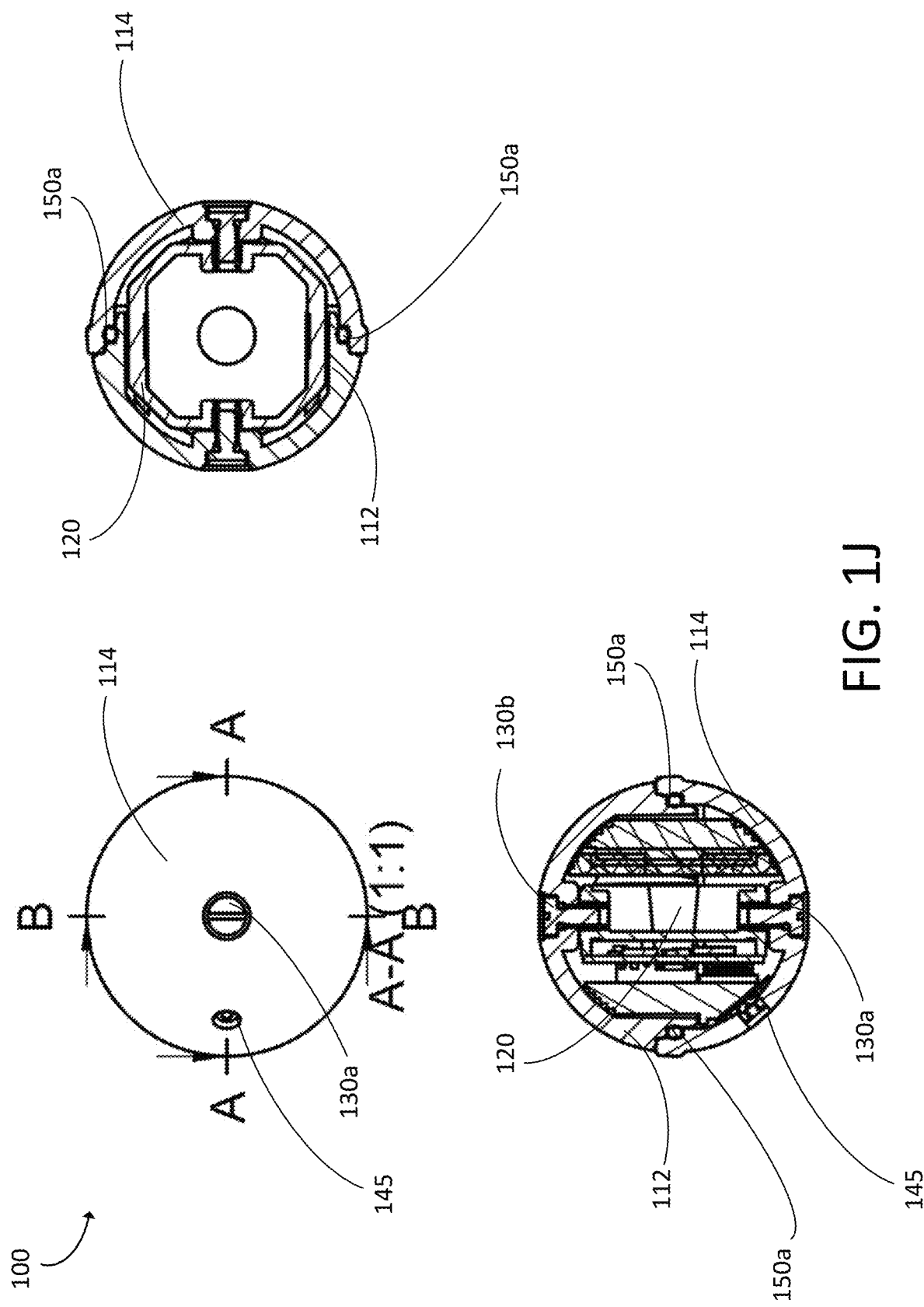

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, and personal computer, cloud based program or system, laptop, personal data assistance, cellular telephone, smartphone, or tablet device.

Reference is made to FIGS. 1A-J and FIGS. 2A-C, illustrated therein a sensor device 100 for sensing fluid properties and fluid conduit properties and collecting fluid data and fluid conduit data, in accordance with an embodiment. The word fluid as used herein includes fluid in liquid, gas and/or mixture of liquid and gas phases. The sensor device 100 can be used to explore, inspect, and/or map areas that are difficult to access such as fluid conduits and fluid surfaces. The sensor device 100 may be free flowing such that the sensor device 100 is not tethered and is transported with the flow of liquid directly. The sensor device 100 captures sensing data along the flow of the liquid.

In a variant, the sensor device 100 may be mounted on a cleaning pig and flows within, e.g., a gas pipeline, with the cleaning pig.

The sensor device 100 may be robust, miniaturized, and suited to measure the actual flow behavior of liquids. For example, the sensor device 100 may be placed in fluid conduits such as pipelines, industrial installations, wave flumes, and open water and measure the properties thereof. The sensor device 100 may be used in industries such as water utilities, waste water plants, oil and gas, fluid dynamics laboratories, and industrial chemical production.

The sensor device 100 may measure the flow dynamics of liquids in an environment. The sensor device 100 may move with the liquid during regular operation and may continuously measure and store the flow dynamics. The sensor device 100 may provide information to better understand flow and optimize processes.

When used in a pipeline, the sensor device 100 may not interrupt the operation of the pipeline, which makes the sensor device 100 suited for frequent use in water, oil, chemical, and slurry pipelines. The capabilities and size of the sensor device 100 may be used in pipelines with challenging dimensions and operation. The collected data contributes to the understanding of the fluid dynamics and condition of the pipeline. The sensor device 100 may also be used in a gas pipeline by being mounted on a cleaning pig that may be launched and received through a launching pigging valve and a receiving pigging valve, respectively. Alternatively, for both liquid and gas pipelines, the receiving and launching pigging valves may be modified by adding a removable accessory for ease of introduction and extraction of the sensor device 100.

When used in a mixing process, the weight of the sensor device 100 may be adjusted to match the weight of commonly used liquids and solids to measure the dynamics of multiphase fluids or multi fluid liquids during operation in an industrial mixer.

Not only useful in the mixing process, but also the ability to adjust the weight of the sensor device 100 can help in adjusting the vertical location of the sensor device 100 within a pipeline. For example, making the sensor device 100 heavier might mean that it can flow lower in the pipeline while making it lighter might mean it can flow higher in the pipeline. By doing so, information about different heights within a pipeline may be gathered. For example, when the sensor device 100 flows closer the bottom of the pipeline it may collect more information regarding the fluid and the conduit in that lateral location. For example, when the fluid comprises of a multiple layers of fluids, by adjusting the weight and thereby the vertical location of the sensor device 100 within the pipeline, the sensor device 100 can collect information about the boundaries between the layers, shear force between the boundaries, differences between layers' flow speeds, presence of water in an oil pipeline, presence of gaseous particles such as air in the pipeline, etc.

The sensor device 100 may be used to measure waste water dynamics. A wastewater stream may have a highly heterogeneous character which may make it difficult to determine flow dynamics and sedimentation. The sensor device 100 may mimic the weight and dynamics of components in the stream and may be particularly suited to optimize transport.

The sensor device 100 may be mixed or combined with other products to perform internal measurements such as movement, temperature, pressure, magnetic field and acoustic measurements to better understand the transportation and full fluid distribution process. Data captured may reveal information about the conditions to which products or resource materials are exposed.

The sensor device 100 includes an outer capsule 110 for providing fluid-tight containment to an interior compartment 170. The outer capsule 110 may be free flowing such that the outer capsule 110 is not tethered to anything and is not required to ride on a surface of a flow conduit (e.g., pipeline).

The outer capsule 110 may also provide pressure resistivity to the interior compartment 170. The outer capsule 110 includes a first capsule portion 112 and a second capsule portion 114 that meet at a capsule seam 116. The first and second capsule portions 112, 114 enclose the interior compartment 170. The first and second capsule portions 112, 114 can be separated to provide access to the interior compartment 170. The sensor device 100 includes a fastener (e.g., 130a, 130b) that closes the first capsule portion 112 with the second capsule portion 114.

In some embodiments, the outer capsule 110 may be roughly spherical and between 1" and 2" in diameter, making sensor device 100 less likely to catch on, for example, sediment in a fluid, or other obstructions. In other embodiments, the outer capsule 110 may be a cube, or may be irregularly shaped. The outer capsule 110 may also be larger than 2" or smaller than 1" in diameter.

The outer capsule 110, when closed, is robust and may be designed to withstand the forces of, for example, being struck by an operating turbine blade installed in the path of fluid flow, or hitting pipeline walls and bends. The outer capsule 110 may also be designed to withstand, for example, around a 435 PSI or 30 bar pressure measured from the interior compartment 170 of the outer capsule 110 to the outside. In other embodiments, the outer capsule 110 may be designed to withstand a pressure of 1450 PSI or 100 bar. The pressure may be limited by the pressure sensor and not the properties of the outer capsule 110.

The outer capsule 110 may also be made of a material that can allow it to operate at temperatures up to about 80 degrees Celsius, and up to about 125 degrees Celsius for short periods. The outer capsule 110 may also be made of a material that is chemically inert with respect to the fluids that the sensor device 100 is intended to be used in. In some embodiments, the outer capsule 110 may be made of an amorphous, transparent polyamide, such as GRILAMED TR™. In other embodiments, other pressure, temperature, and chemical specifications may be used. For example, the outer capsule 110 may be made of one or more metals.

The outer capsule 110, when assembled, is fluid-tight and/or pressure-resistive. Referring to FIG. 2A, the sensor device 100 includes an O-ring 150a for sealing the outer capsule seam 116. The sensor device 100 includes O-rings 150b, 150c for sealing other apertures in the outer capsule 110. The sensor device 100 may also include an O-ring for sealing a pressure sensor 142 that is installed in an aperture 145 in the outer capsule 110.

In other embodiments, the outer capsule 110 may be made fluid-tight and/or pressure-resistive using seals other than the O-rings 150a, 150b, 150c such as, for example, glue or thread seal tape. In other embodiments, the outer capsule 110 may be made effectively fluid-tight and/or pressure-resistive by pressuring the interior compartment 170. In other embodiments, the outer capsule 110 may not be perfectly fluid-tight and/or may not be pressure-resistive, and the contents of the interior compartment 170 may be protected, such as, for example, using conformal coating (e.g. 129 at FIG. 3C) to provide fluid resistance to the components in the interior compartment 170.

The sensor device 100 may include no weights or may include one or more weights, such as weight 160a and weight 160b, for adjusting the mass of the sensor device 100. The weights 160a and 160b may be seated in grooves 172a and 172b provided in the interior compartment 170, and may conform to the shape of the outer capsule 110 so as to fit inside the outer capsule 110 when the first capsule portion 112 is assembled with the second capsule portion 114. Using the weights, such as weight 160a and 160b, the specific gravity of the sensor device 100 may be adjusted to a value between 0.5 and 3 times the specific gravity of water. In other embodiments, the specific gravity of the sensor device 100 may be adjusted between 0.85 and 2.35 times the specific gravity of water. In some embodiments, the mass of the sensor device 100 may be adjusted to be neutrally buoyant with the fluid being measured by the sensor device 100. In other embodiments, higher or lower specific gravities may be attained, for instance, by using different weights and/or an outer capsule of a different size.

While the sensor device 100 includes two weights 160a, 160b, it will be understood that none, one or both of weights 160a, 160b may be used in the interior compartment 170, depending on the desired mass. Where additional weights are available, different combinations of those weights may also be used to yield different masses for the sensor device 100.

The weights 160a and 160b may be shaved or adjusted to change their mass. The weights 160a and 160b may also be made of a high density and soft material such as brass, may resist corrosion, and have a high density so as to minimize the volume. Brass weights may also have the added advantage of being adjustable (e.g. by machining) to tune the weight of the sensor device 100 to compensate for variations in the mass of the sensor device 100.

The weights 160a, 160b may also adjust a center of mass of the sensor device 100. For example, referring specifically to FIG. 1F, the center of mass of the sensor device 100 without using weights 160a, 160b is located at a point 161 within the sensor device 100, while the center of mass of the sensor device 100 with weights 160a, 160b is located at a point 162 within the sensor device 100.

The center of mass of the sensor device 100 may be adjusted (e.g. using weights 160a and/or 160b) such that the center of mass is different from a geometrical center 169 of the sensor device 100. Where the center of mass of the sensor device 100 is different from the geometrical center 169 of the sensor device 100, the sensor device 100 may be more attitudinally stable when moving through a fluid. To increase the distance between the geometrical center of the sensor device 100 and its center of mass, different configurations and/or selections of materials may be used for the components of the sensor device 100, such as the outer capsule 110, the inner frame 120, and the weights 160a, 160b. In embodiments where the outer capsule 110 is not convex, or in embodiments where the sensor device 100 includes a plurality of outer capsules, the center of mass of sensor device 100 may be located outside the sensor device 100.

The outer capsule 110 and weights 160a and 160b may also be (together or individually) colored differently depending on the mass of the weights used for weights 160a and 160b, so as to make it easier to distinguish between sensor devices of different masses.

The sensor device 100 also includes at least one sensor 180 for sensing fluid properties and fluid conduit properties. The sensor 180 may be an inertial measurement unit (IMU). The IMU measures linear and angular motion. The IMU may have its center at a geometrical center of the sensor device 100. The sensor 180 also includes a magnetometer for measuring the strengths of magnetic fields. In other embodiments, the sensor 180 may include any one or more of pressure, temperature, and ultrasonic sensors. In some embodiments, the sensor 180 may include an external-facing sensor such as the pressure sensor 142, installed in the aperture 145 in the outer capsule 110.

In an embodiment, the sensor device 100 includes a sensor 180 that measures the vibration of the outer capsule 110 to determine the acoustic properties of the fluid and fluid conduit at a given location. This vibration sensor 180 may detect leaks in the fluid conduit, as discussed in more detail below.

The sensor device 100 also includes a sensor platform 140. The sensor 180 is provided on the sensor platform 140. The sensor platform 140 provides support to other components that support the operation of the sensor 180. The sensor platform 140 may be provided on a printed circuit board with soldered components. For example, FIG. 3D illustrates a circuit board front 1500 and back 1502 in accordance with an embodiment of the sensor platform 140. Referring specifically to FIGS. 2B and 2C, an external-facing sensor such as the pressure sensor 142 may include a set of wires 143 for connecting the pressure sensor 142 to the sensor platform 140.

The sensor device 100 also includes conductors 130a and 130b for activating the sensor 180 to sense fluid data and fluid conduit data. The conductors 130a and 130b are each electrically connected to sensor platform 140, and are exposed on the surface of outer capsule 110, so as to allow signals to be sent to and/or received from the sensor platform 140. While sensor device 100 uses two conductors, in other embodiments, one or more conductors may be used.

In the sensor device 100, the conductors 130a and 130b include fasteners to close the first capsule portion 112 to the second capsule portion 114. The fasteners are threaded bolts that are received in threaded apertures on opposite surfaces of the inner frame 170. In other embodiments, the outer capsule 110 may be closed using fitted self-locking grooves disposed where the edges of the first capsule portion 112 meet the edges of the second capsule portion 114 along the outer capsule seam 116. In other embodiments, the conductors 130a and 130b may not be necessary to close the first capsule portion 112 to the second capsule portion 114.

The sensor device 100 also includes an inner frame 120, which can be physically installed in and removed from the interior compartment 170. The sensor platform 140 is mounted on the inner frame 120. The inner frame 120 also provides a conduit for the conductors 130a, 130b to activate the sensor 180 via the sensor platform 140. The conductors 130a, 130b also close the first capsule portion 112 to the second capsule portion 114 by each attaching the respective capsule portion 112, 114 to the inner frame 120.

Figure 3B:
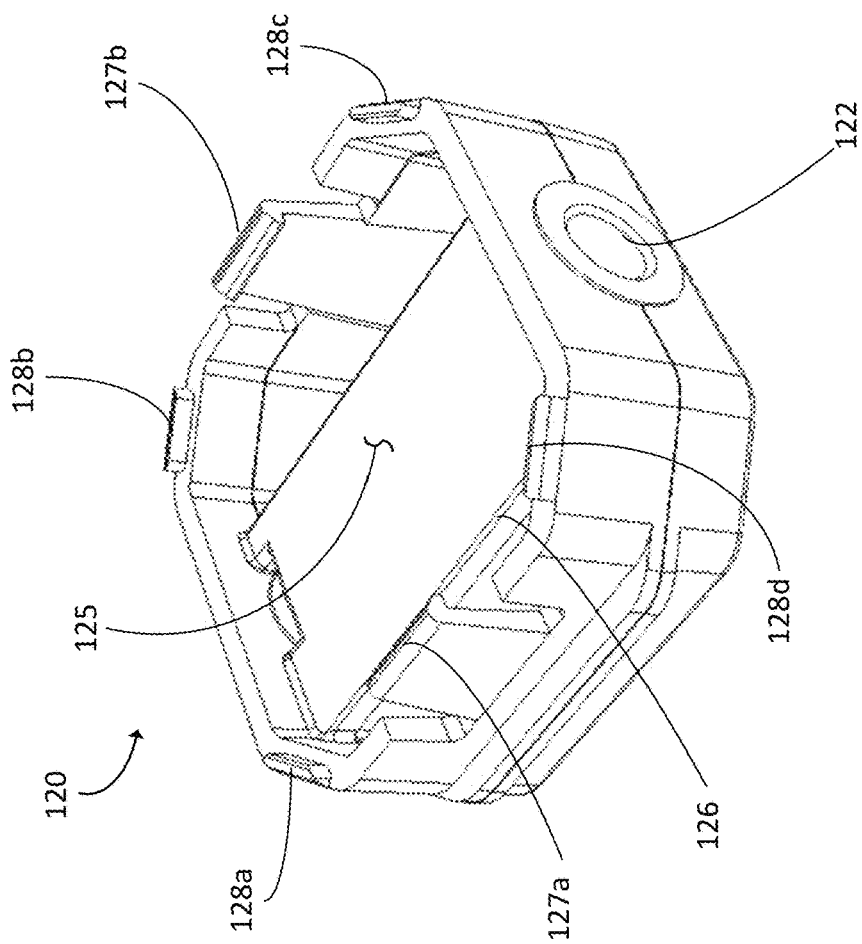
FIGS. 3A and 3B are top and bottom perspective views, respectively, of an inner frame of the sensor device of FIG. 1A.
Figure 3A:
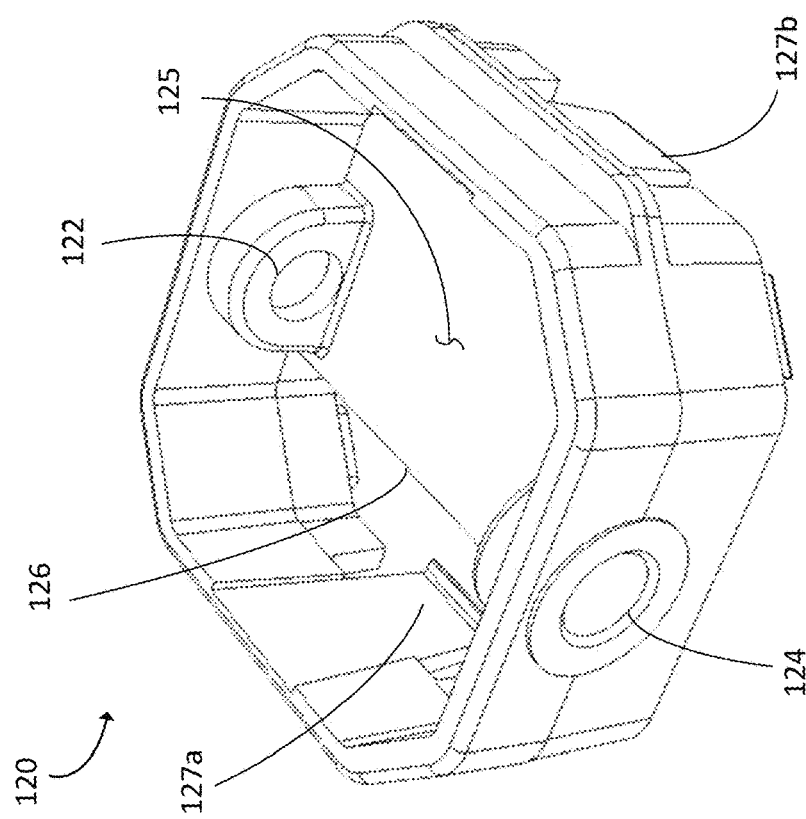
Figure 3C:
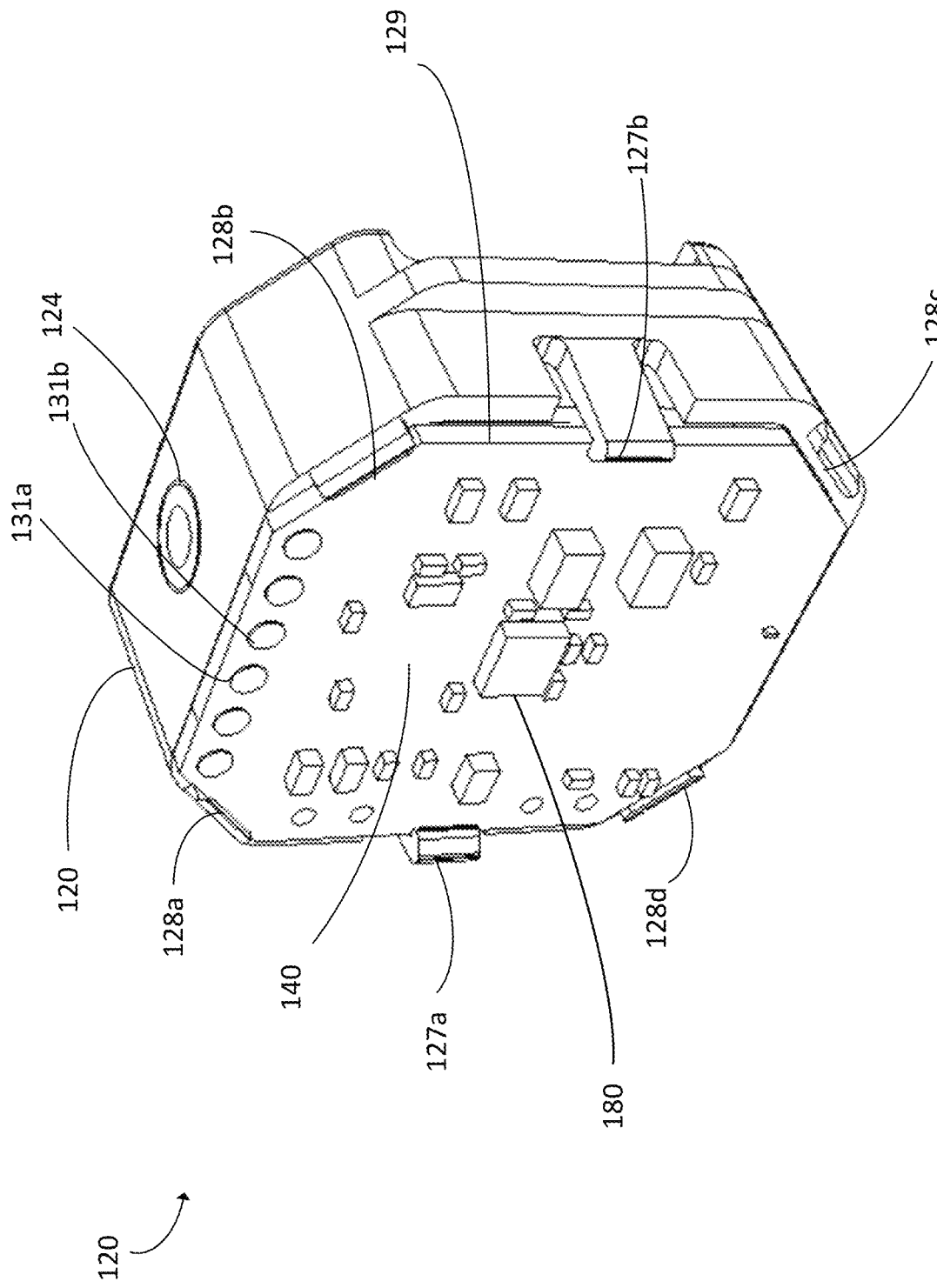
FIG. 3C is a bottom perspective view of the inner frame and a sensor platform of the sensor device of FIG. 1A.

Reference is now made to FIG. 3A and FIG. 3B, which depict the top and bottom perspective views of the inner frame 120 of sensor device 100, respectively, where the sensor platform 140 has been removed. Reference is also made to FIG. 3C, which depicts a bottom perspective view of the inner frame 120 of the sensor device 100 where the sensor platform 140 has been installed.

The inner frame 120 provides a frame for mounting the sensor platform 140. The inner frame 120 includes clips 127a, 127b and spacing ridges 128a, 128b, 128c, 128d for holding the sensor platform 140 in place. Referring specifically to FIG. 3C, the spacing ridges 128a, 128b, 128c, 128d prevent the sensor platform 140 from sliding out from under the clips 127a, 127b. The clips 127a, 127b may be the only elements that hold the sensor platform 140 in place, such that no other component is needed to affix the sensor platform 140 to the inner frame 120, increasing the simplicity of the design of the inner frame 120. Use of the clips 127a, 127b to secure the sensor platform 140 to the inner frame 120 also allows the sensor platform 140 to be removable from the inner frame 120, e.g., for repairs and inspection of the sensor platform 140. In other embodiments, the sensor platform 140 may be affixed to the inner frame 120 using, for example, glue, fasteners, etc., or may form a part of the inner frame 120 itself.

The inner frame 120 and/or the sensor platform 140 may also, in some embodiments, be coated with a fluid-resistant substance in order to protect the sensor platform 140. For example, the sensor platform 140 may be coated in a conformal coating 129, such as a thin polymeric film.

The inner frame 120 also includes coaxially opposed threaded bores 122 and 124, which receive threaded conductors 130a and 130b to secure the first capsule portion 112 and the second capsule portion 114 to the inner frame 120. The inner frame 120 includes a plate element 126 for separating the sensor platform from other components, such as a power source. The plate element 126 may include a non-conductive surface 125, to protect the circuitry of the sensor platform 140 and/or to prevent shorting with the power source.

In some embodiments, the inner frame 120 may also include a back plate for securing the power source to the inner frame, and/or to protect the power source. The back plate may be glued to the body of the inner frame 120, or may snap in place and/or be removed to service the power source.

Figure 6:
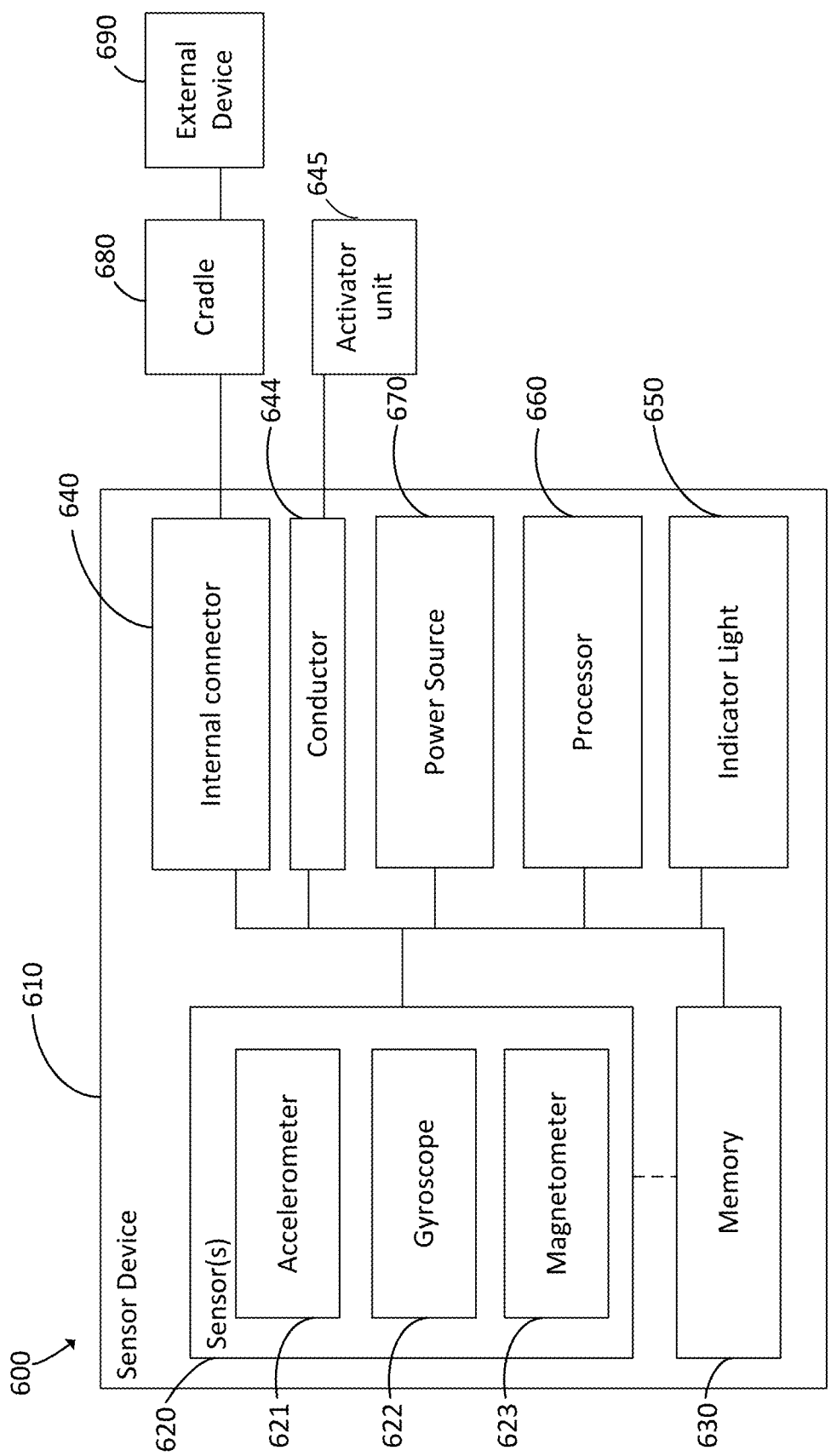
FIG. 6 is a block diagram of a system for collecting fluid data and fluid conduit data, in accordance with an embodiment.

The inner frame 120 can be removed from the interior compartment 170 and be fitted into a cradle (e.g. cradle 400 at FIG. 4A) to allow the sensor platform 140 to be connected to an external device (e.g. device 690 of FIG. 6). The sensor platform 140 includes internal connectors 131a, 131b to facilitate connection of the sensor platform 140 with an external device through the use of the cradle. The internal connectors 131a, 131b may each correspond to a spring-loaded pin (e.g. 431a, 431b at FIG. 4) provided by the cradle, such that when the inner frame 120 is fitted into the cradle, the internal connectors 131a, 131b are each connected to their corresponding spring-loaded pin. In some embodiments, the inner frame 120 does not have to be fitted to a cradle in order to connect the sensor platform 140 to an external device, and the sensor platform 140 may not include the internal connectors 131a, 131b. In some embodiments, the inner frame 120 does not have to be removed from the interior compartment 170 in order to be connected to the external device. In such embodiments, the sensor platform 140 may be connected to an external device by way of, e.g., a USB port (not shown) installed on the sensor platform 140. Moreover, in such embodiments, the inner frame 120 may be fused to or form a part of the outer capsule 110.

Reference is now made to FIGS. 4A-D, which illustrates a cradle or capsule dock 400, in accordance with an embodiment. Reference is also made to FIGS. 4E-H, which illustrate a cradle or capsule dock 400 in accordance with another embodiment. Reference is also made to FIGS. 4I-L, which illustrate a cradle or capsule dock 400 in accordance with another embodiment.

The cradle 400 includes a connection 402 to an external device (e.g. device 690 of FIG. 6). In some embodiments, the connection 402 may include a USB port. The cradle 400 mates with the inner frame 120 and sensor platform 140 of the sensor device 100. The cradle 400 includes a cradle latch 404 for positioning the sensor device 100 in the cradle 400. The cradle 400 connects to the memory of the sensor device 100 and provides the stored fluid data and fluid conduit data to a computer system (e.g. device 690 of FIG. 6). The cradle 400 also includes view ports 436a, 436b for viewing any indicator lights that may be on the sensor platform 140 when the sensor platform 140 has been connected to the cradle 400.

The cradle 400 may be adapted to fit the inner frame 120 of the sensor device 100 while the inner frame 120 is attached to a portion of the outer capsule 110 of the sensor device 100.

The cradle device 400 also includes an interface 430 for connecting to a sensor platform (e.g. sensor platform 140 of FIG. 3C). The interface 430 may include spring-loaded pins 431a, 431b, 431c, 431d, 431e, 431f to connect to the internal connectors of the sensor platform (e.g. 131a, 131b at FIG. 3C). The cradle 400 also includes a logic board 410, for providing the components necessary to interface an external device (e.g. device 690 of FIG. 6) with a sensor platform (e.g. sensor platform 140 at FIG. 3C). The logic board 410 is connected to the interface 430. The logic board 410 is also connected to the connection 402. The cradle 400 may also include an additional power LED to indicate when the logic board 410 is getting power from the connection 402.

Figure 4H:
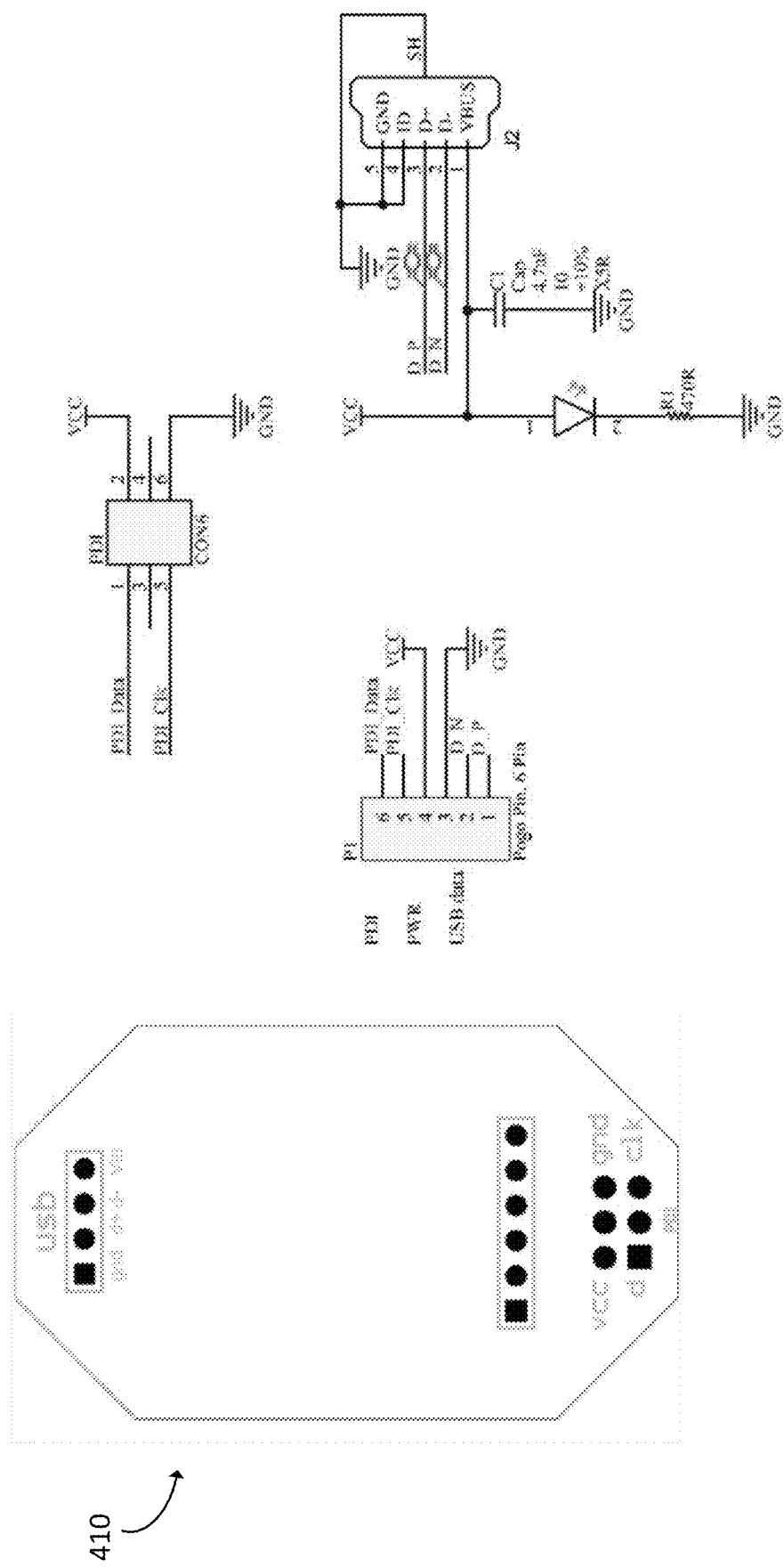
FIG. 4H is a circuit schematic and PCB layout of the logic board of the capsule dock of FIG. 4E.
Figure 4J:
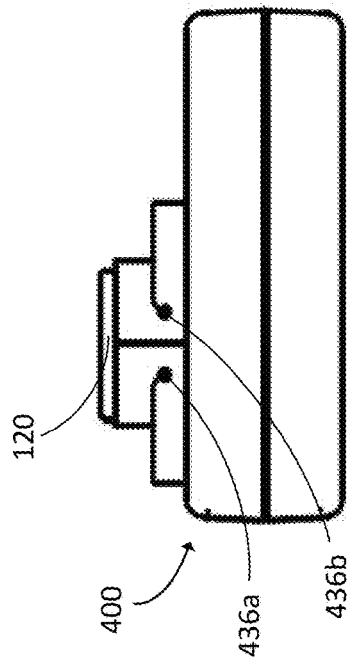
FIGS. 4I, 4J, 4K, and 4L are a side view, another side view, a top view, and a perspective view, respectively, of a capsule dock for the sensor device of FIG. 1A with an inner frame of FIG. 3A installed, in accordance with an embodiment.
Figure 4I:
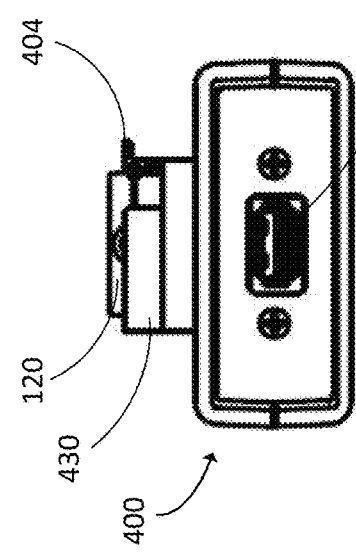
Figure 4L:
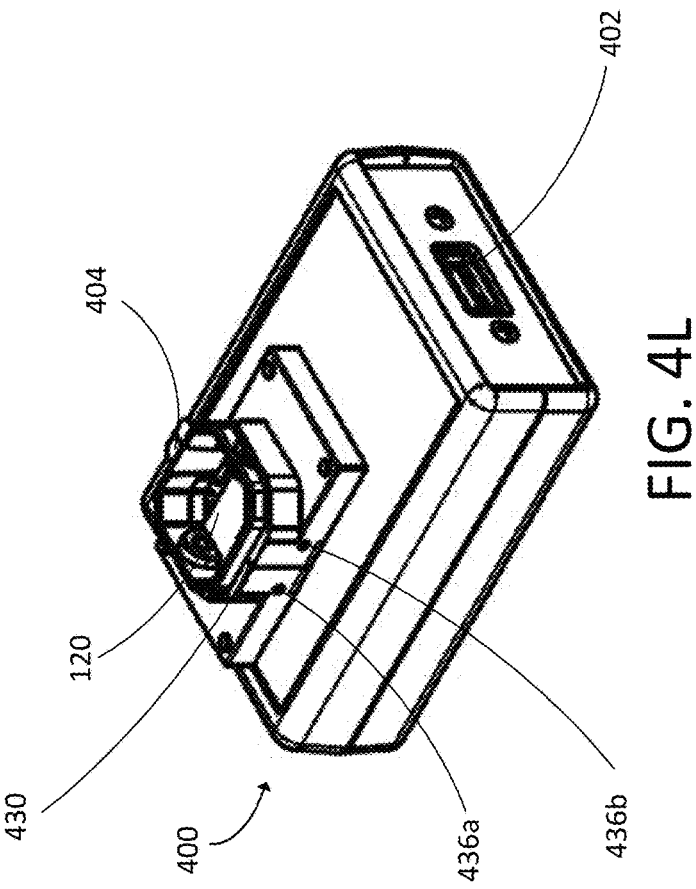
Figure 4K:
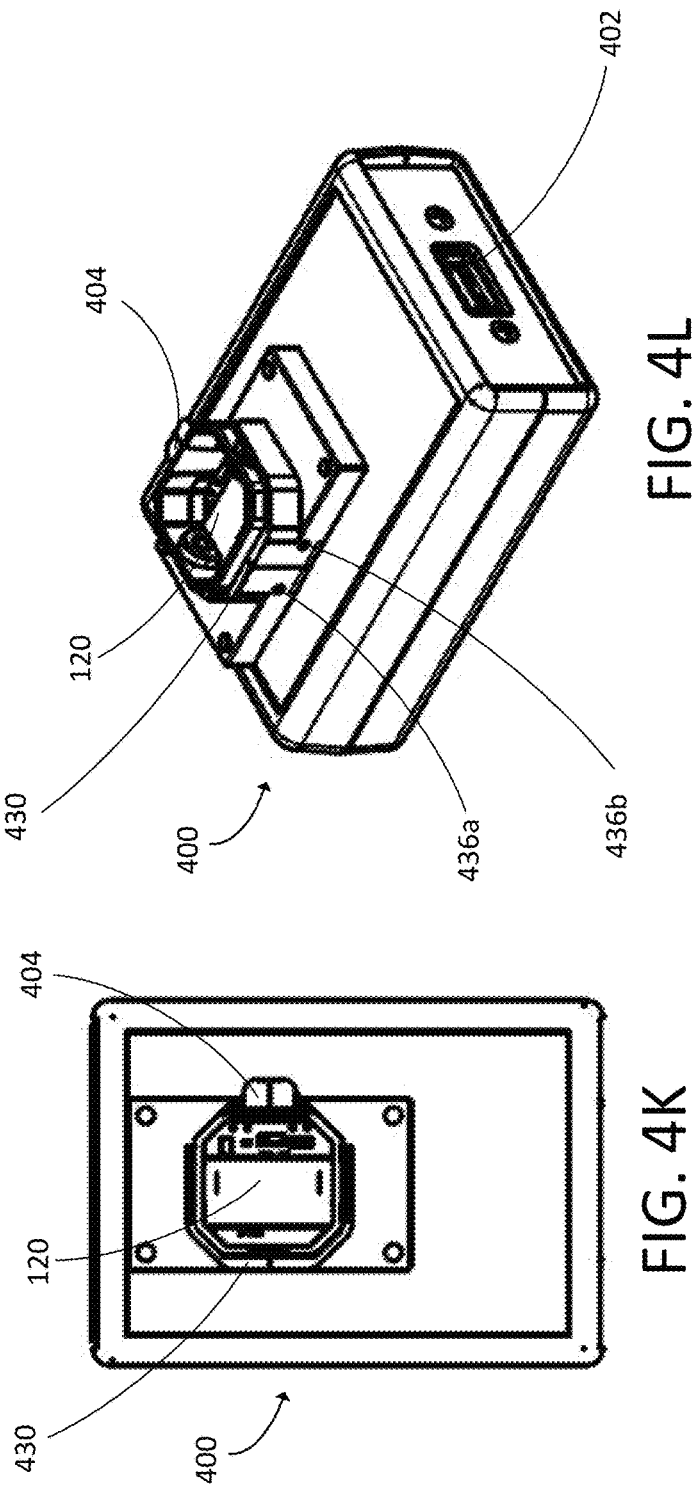
Figure 4P:
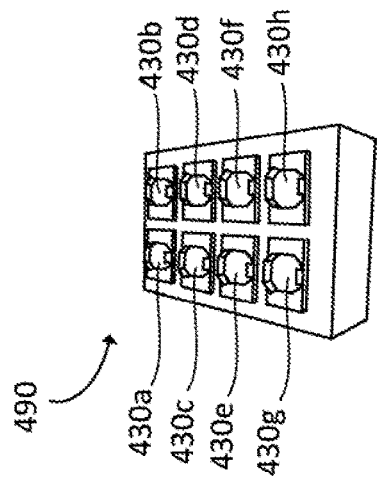
FIGS. 4M, 4N, 4O, and 4P are a side view, a top view, a perspective view and another perspective view, respectively, of a capsule dock for a plurality of the sensor devices of FIG. 1A, in accordance with an embodiment.
Figure 4O:
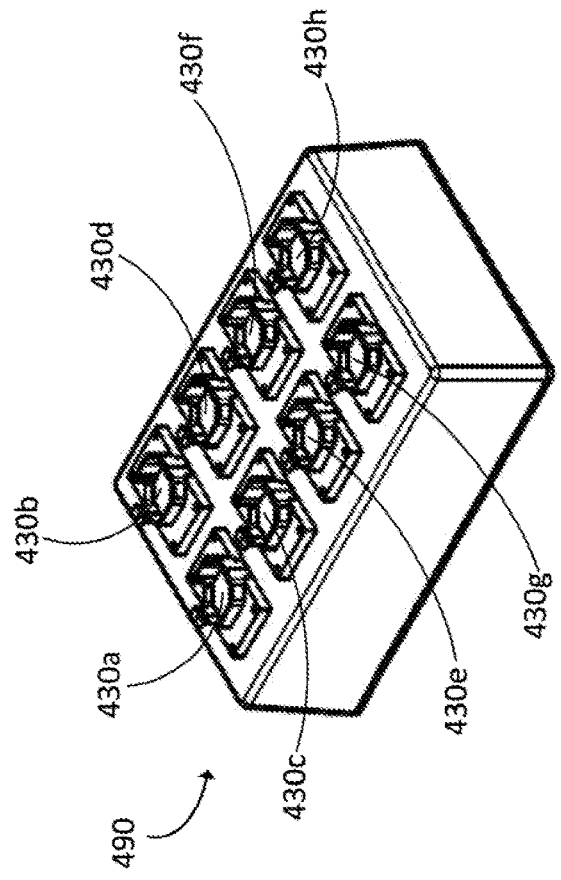
Figure 4M:
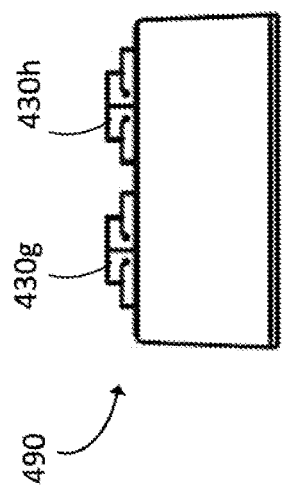
Figure 4N:
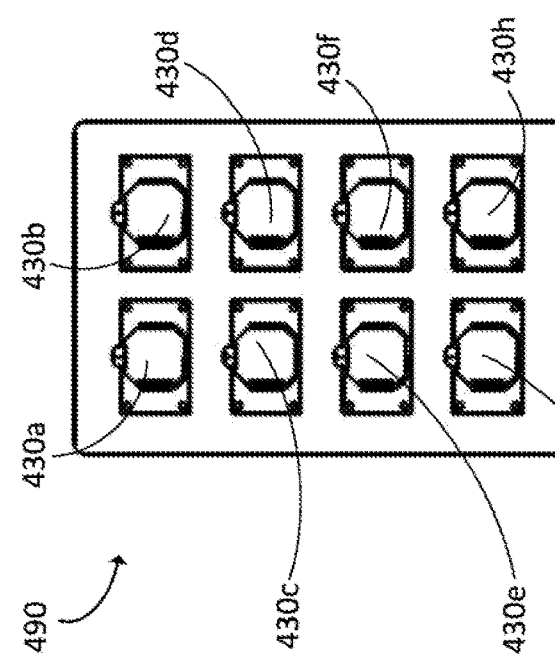

Referring specifically to FIGS. 4E-G, some embodiments of the cradle 400 may include a pin header 432 for connecting to an external device (e.g. device 690 of FIG. 6). Connections between the pin header 432 and the spring-loaded pins 431a, 431b, 431c, 431d, 431e, 431f may be provided by logic board 410. The pin header 432 may be used to provide an interface for external programming and/or on-chip debugging of a sensor platform (e.g. sensor platform 140 of FIG. 3C). In some embodiments, the interface may implement the Program and Debug Interface specification by Atmel®. A circuit schematic and PCB layout for specifically implementing the Program and Debug Interface can be found in FIG. 4H. The pinouts described in FIG. 4H correspond to the pinouts indicated in FIG. 4F. Specifically, to implement the Program and Debug Interface, some of the spring-loaded pins 431a, 431b, 431c, 431d, 431e, 431f may correspond to VCC, GND, PDI_Data and PDI_Clk, as required by the Program and Debug Interface specification. The spring-loaded pins 431a, 431b, 431c, 431d, 431e, 431f not used for the Program and Debug Interface may be connected to the connection 402 (e.g. D+ and D− of the USB specification). Not all of the spring-loaded pins 431a, 431b, 431c, 431d, 431e, 431f may be connected to the pin header 432. In some embodiments, the external device that connects to the pin header 432 may be different from the external device that connects using connection 402.

While the cradle device 400 may be asymmetric having pins in the location where the sensor system is going, the cradle device 400 may be symmetric to shift the pins out such that there would be no faulty connection.

Reference is now made to FIG. 4M-P, which illustrates a perspective view of cradle or capsule dock 490, in accordance with another embodiment. The capsule dock 490 includes a plurality of interfaces 430a, 430b, 430c, 430d, 430e, 430f, 430g, 430h for connecting to multiple sensor platforms (e.g. sensor platform 140 of FIG. 3C) to an external device (e.g. device 690 of FIG. 6). The capsule dock 490 may also include a plurality of logic boards 410a, 410b, each corresponding to an interface of the plurality of interfaces 430a, 430b, 430c, 430d, 430e, 430f, 430g, 430h, each for providing the components necessary to interface an external device (e.g. device 690 of FIG. 6) with a sensor platform (e.g. sensor platform 140 of FIG. 3C). In other embodiments, the capsule dock 400 includes only a single logic board 410a.

Figure 5A:
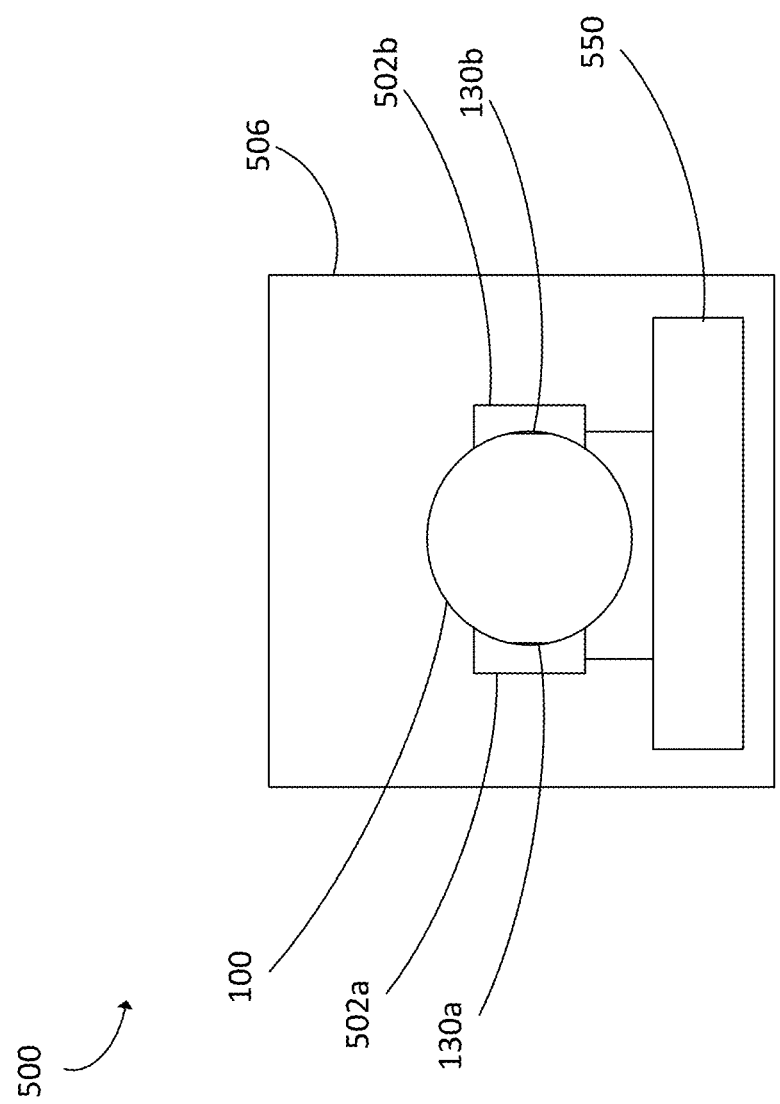
FIG. 5A is a block diagram of an activator unit for the sensor device of FIG. 1A, in accordance with an embodiment.
Figure 5B:
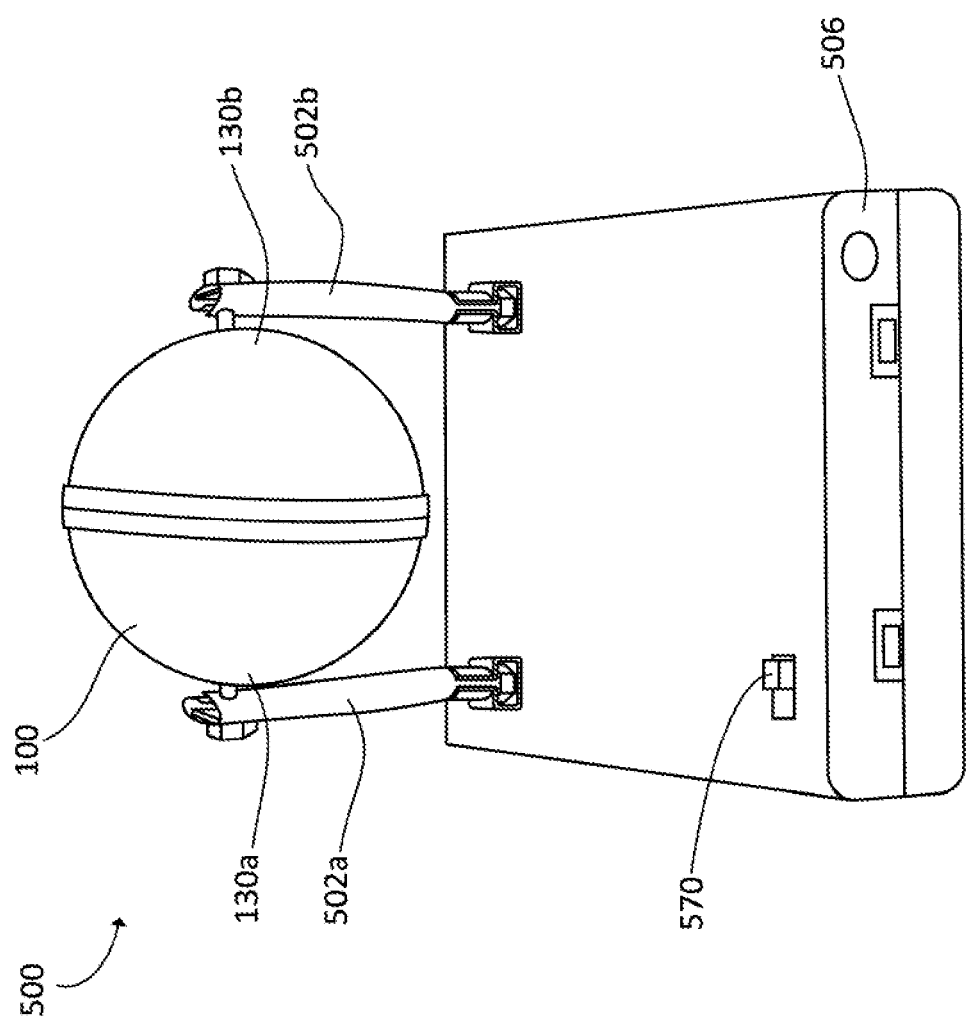

Reference is now made to FIGS. 5A and 5B, which illustrates perspective views of an activator unit 500. The activator unit 500 may be used to apply a signal across the conductors of a sensor device (e.g. 130a, 130b of FIG. 1E). The activator unit 500 includes a base 506 supporting a pair of conducting arms 502a, 502b connected to an activator power source 550.

The activator power source 550 may include a pair of AA batteries. In other embodiments, the activator power source 550 may instead include other sources of electromotive force, such as a 9V battery, or a rectifier for use with a power outlet. In other embodiments, activator power source 550 may provide AC power.

The conducting arms 502a, 502b may apply a signal across the conductors of a sensor device (e.g. 130a, 130b of FIG. 1E) when connected to those conductors. Various signals may be applied using conducting arms 502a, 502b. For example, a signal may be applied by applying, through the conducting arms 502a, 502b, the activator power source 550 to the conductors of a sensor device (e.g. 130a, 130b of FIG. 1E) for 2 or more seconds. This signal may be interpreted by the sensor device differently than, for example, a signal that is less than 2 seconds long. In some embodiments, a signal provided by the activator unit 500 may be used to activate the sensor device (e.g. sensor device of FIG. 1A).

In some embodiments, the activator unit 500 may include an on/off switch 570. The on/off switch 570, when closed, connects the activator power source 550 to the conducting arms 502a, 502b. When the on/off switch 570 is open, the activator power source 550 is not connected to the conducting arms 502a, 502b. This allows the sensor device 100 to be attached to the conducting arms 502a, 502b without a signal being sent across the conductors 130a and 130b of the sensor device 100.

Reference is now made to FIG. 6, which illustrates a system 600 for collecting fluid data and fluid conduit data, in accordance with an embodiment. The system 600 includes an encapsulated sensor device 610, such as the sensor device 100 described with reference to FIGS. 1A-F, 2A-C, and 3A-D, for immersing in a fluid to collect the fluid data and fluid conduit data. The system 600 also includes cradle 680, which can communicate with an external device such as a computer system 690. The sensor device 610 includes an outer capsule that is free flowing within the fluid and provides fluid-tight containment to an interior compartment.

The free flowing nature of the sensor device 610 may advantageously provide for the reduction or elimination of background noise. The reduction or elimination of background noise may provide for the easier identification of leaks or other fluid properties. In particular, the reduction or elimination of background noise may increase efficiency of the system by reducing the need for a pre-processing noise elimination step in the processing of sensed properties. In particular, the free-flowing nature of the sensor device 610 may advantageously lead directly to the identification of fluid properties such as the identification of a leak.

The sensor device 610 includes a sensor 620 for taking measurements about a property of the fluid. The sensor 620 may include any one or more of a triaxial accelerometer 621, a triaxial gyroscope 622, and a triaxial magnetometer 623. In other embodiments, the sensor 620 may include other sensors. For example, sensor 620 may include a pressure sensor, a temperature sensor, and/or an ultrasonic sensor.

The sensor device 610 includes a memory 630 for storing measurements taken by the sensor 620. The memory 630 may include 1 GB of Serial NOR Flash Memory. In other embodiments, the memory 630 may include other forms and sizes of computer-readable memory. The memory 630 may also be removable and/or swappable. For example, the memory 630 may be an SD or microSD card fitted to an appropriate interface. The memory 630 may receive data directly from the sensor 620, or it may communicate with sensor 620 via a processor 660. When the memory 630 is full, it may shut down the sensor device 610 automatically by signaling the memory status to the processor 660.

The sensor device 610 includes at least one internal connector 640 (e.g., 131a, 131b at FIG. 3C) for communicating with the computer system 690. The internal connector 640 includes selectively exposed electrical contacts connected to the processor 660. The exposed electrical contacts correspond to a set of pins (e.g. 431a-f in FIG. 4A) in the cradle 680, such that when the sensor device 610 is interfaced with the cradle 680, the processor 660 can be connected to the computer system 690. In some embodiments, the internal connector 640 may include a USB port directly connected to the processor 660. In other embodiments, the conductors 640 may include other forms of connectors, such as jumper headers, an RS-232 serial port, a FireWire port, etc.

The sensor device 610 may also include conductors 644 (e.g. 130a and 130b at FIG. 2A). The processor 660 may accept different instructions through the internal connector 640 than through the conductors 644 of sensor device 610. For example, the processor 660 may only turn on or off the sensor device 610 in response to signals received through the conductors 644 via an activator unit 645. In other embodiments, all signals from sensor device 610 to the computer system 690 may be routed through the conductors 644.

The sensor device 610 includes a set of indicator lights 650 for indicating the status of the sensor device 610. The indicator lights 650 may include a red light and a green light. The indicator lights 650 may be light-emitting diodes. The indicator lights 650 may be operated by the processor 660 to provide an indication of the status of the sensor device 610. For example, a constant red light may indicate that the power source 670 of sensor device 610 is charging. A constant green light may indicate that power source 670 of sensor device 610 is full and cannot be charged any further. The indicator lights 650 may also blink three times to indicate that the sensor device 610 has been turned on. The indicator lights 650 may also blink every 10 seconds to indicate that the sensor device 610 has been turned on, but that use of the sensor 620 has been delayed for some pre-set duration. The indicator lights 650 may also blink every 2 seconds to indicate that the sensor 620 is operational and collecting data. The indicator lights 650 may also blink twice every second to indicate that the memory 630 is full and cannot record any further measurements from the sensor 620. The indicator lights 650 may also blink twice in rapid succession to indicate when the sensor device 610 has just been turned off. In other embodiments, other quantities, types, colors and/or operations of the indicator lights 650 may be used. In an embodiment, the indicator lights 650 may be positioned on the cable (e.g., the proprietary cable 300 shown in FIGS. 14A and 14B, discussed below).

The sensor device 610 includes the processor 660 for performing logical operations. The processor 660 may be an ATxmega128A4U-CU processor manufactured by Atmel. The processor 660 may be reprogrammable (e.g. using instructions from computer system 690) to change the capabilities and configuration of sensor device 610. For example, the processor 660 may be programmed to set the rate at which data is captured by sensor 620, and/or the time the sensor device 610 should wait before beginning to collect data using sensor 620. The processor 660 may also accept instructions to change the range of values that the sensor 620 should measure, and the number of bits that should represent each measurement. In other embodiments, an appropriate general purpose processor (or a combination of such processors) may be used for the processor 660, and other instructions could be accepted by the processor 660.

The processor 660 may also instead be implemented as a state machine to simplify the design and/or power consumption of sensor device 610.

The sensor device 610 includes a power source 670 for providing power to the components of the sensor device 610. The power source 670 provides stored power to perform continuous measurements by the sensor 620. For example, the power source 670 may be a 3.7V lithium polymer rechargeable battery with approximately 165 mAh in charge which provide continuous sensing for around one hour or more. When the power source 670 is low on stored power, it may turn off the sensor device 610 automatically by sending a signal to the processor 660. The power source 670 may be chargeable through the set of conductors 644 with the activator unit 645.

In other embodiments, the power source 670 may be a different battery, or may be, e.g., a converter of electromagnetic radiation into electrical current. The power source 670 may be charged using the internal connectors 640, and charging may occur when the sensor device 610 is interfaced with the cradle 680. The power source 670 may be charged by USB power.

The computer system 690 may be a general purpose computer that includes a USB port. In other embodiments, other ports can be used, depending on the ports available on the cradle 680. The computer system 690 is configurable to accept data from the sensor device 610 by way of the internal connectors 640, and optionally, the cradle 680. Where cradle 680 is not used, the computer system 690 includes an interface for interfacing directly with the conductors 640 (e.g. jumper headers, an RS-232 serial port, a FireWire port, a USB port, etc.). The computer system 690 may be able to instruct the processor 660 to erase data stored in the memory 630 (i.e. to make space for future data).

Figure 7A:
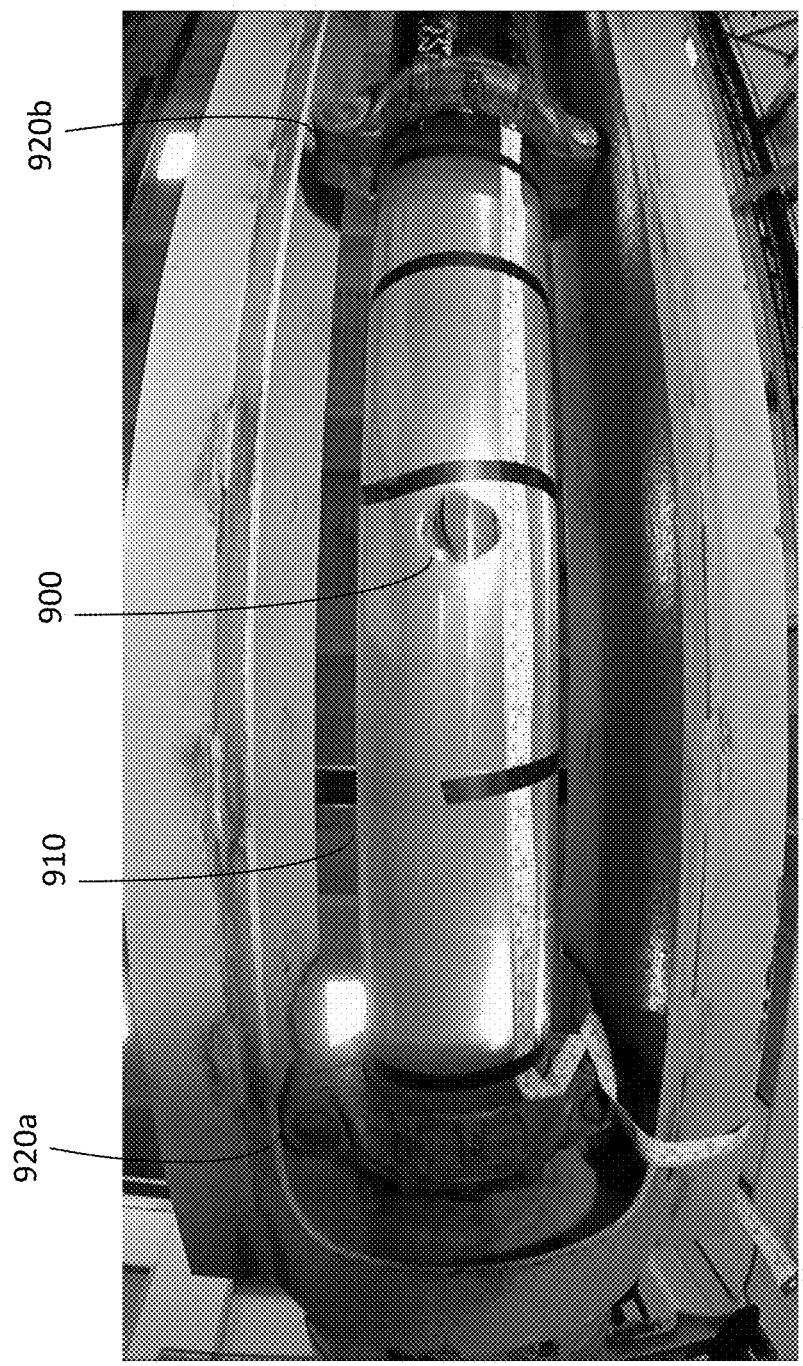
FIG. 7A is a photograph of a sensor device suspended in a fluid inside a pipeline, in accordance with an embodiment.

Reference is now made to FIG. 7A, which depicts a sensor device 900 suspended in a fluid, the fluid conveyed inside a pipeline 910. As the sensor device 900 is conveyed through the pipeline by the fluid, the sensor device 900 may collect data at regular intervals. For example, the sensor device 900 may collect inertial data that includes the acceleration and orientation of the sensor device 900. The sensor device 900 may also collect magnetometer data, which allows the sensor device 900 to sense the Earth's magnetic field. The sensor device may use the Earth's magnetic field as a constant reference. The sensor device 900 may also sense magnetic signals given off by a magnetic flow meter, a pump, a heater, etc. The sensor device 900 may also sense any material that generates a magnetic signature. For example, the sensor device 900 may sense, for instance, ferrous flanges 920a and 920b, any welds, etc. that may be located along the length of the pipeline, which may be used as indicators of location.

Figure 7B:
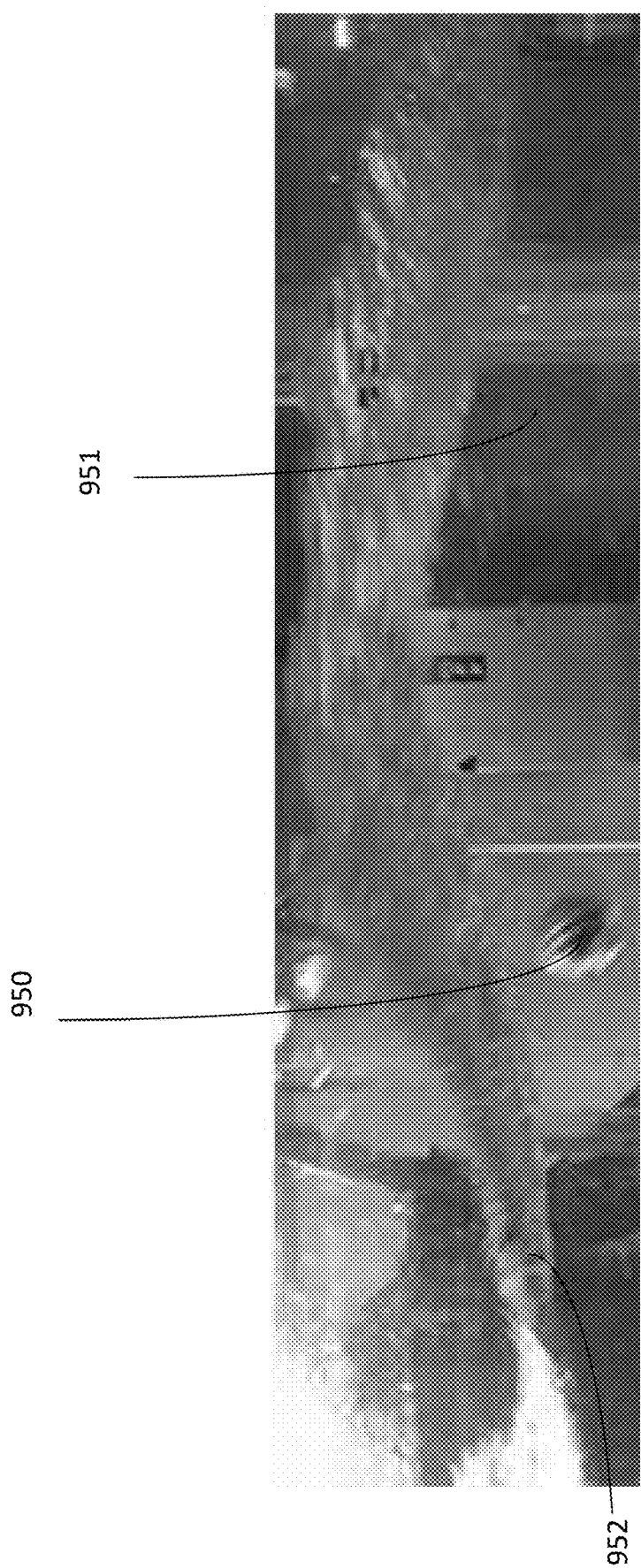
FIG. 7B is a photograph of a sensor device suspended in a fluid with a wave passing through the fluid, in accordance with an embodiment.

Reference is now made to FIG. 7B, which depicts a sensor device 950 suspended in a fluid 951 with a wave 952 passing through the fluid. The sensor device 950 may collect data that allows the flow dynamics of the wave 952 to be analyzed.

Figure 8:
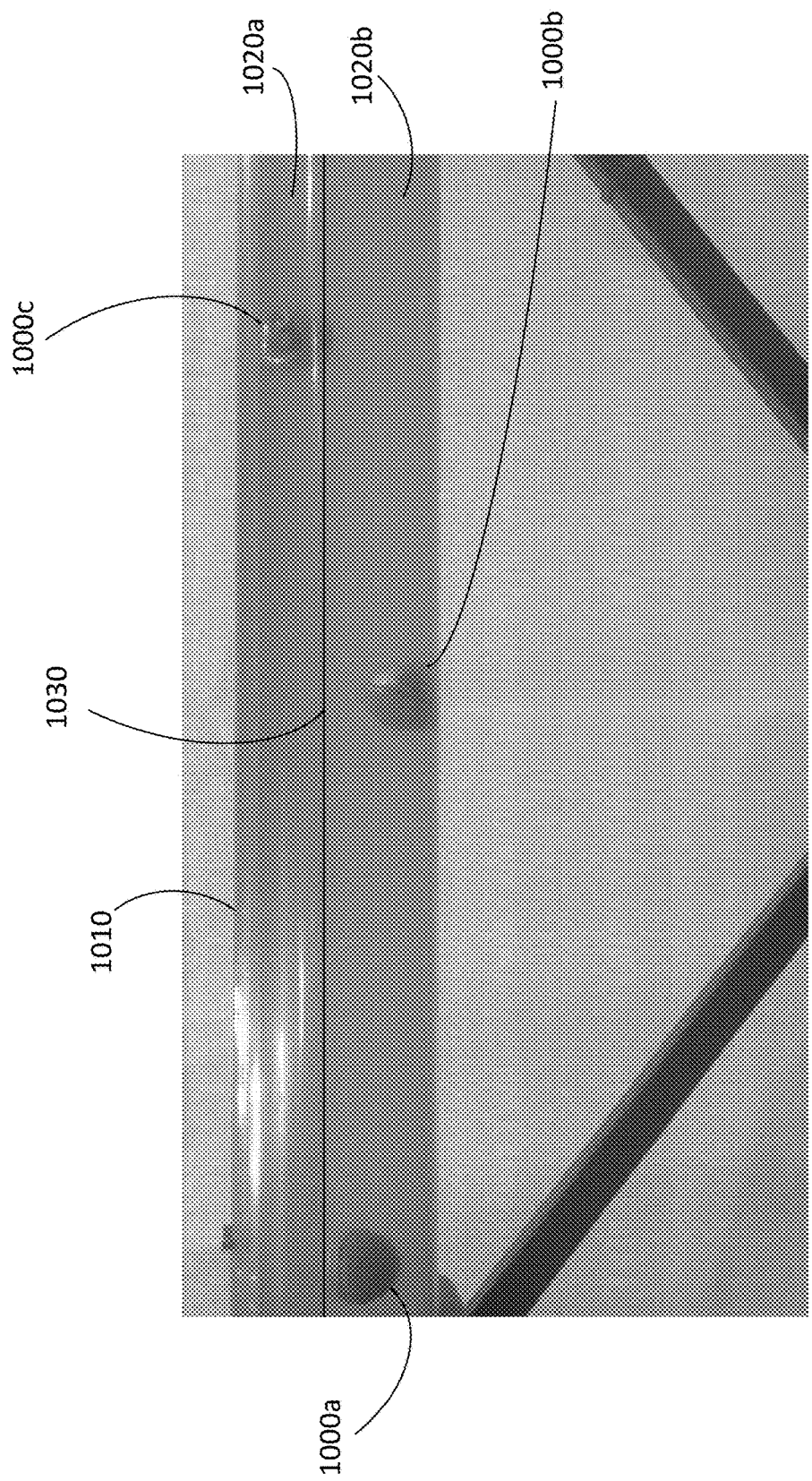
FIG. 8 is a photograph of a plurality of sensor devices inside a pipeline containing several fluids of different densities, in accordance with an embodiment.

Reference is now made to FIG. 8, which depicts a set of sensor devices 1000a, 1000b, and 1000c suspended in a fluid, the fluid conveyed inside pipeline 1010. The pipeline 1010 may contain two or more different fluids of different densities, here 1020a and 1020b, which meet at a fluid interface 1030. The fluids may also be in different phases (e.g. liquid and gas). By adjusting the average density of each of sensor devices 1000a, 1000b, and 1000c (e.g. using weights), the first set of sensor devices can be suspended in fluids 1020a and 1020b at different heights within pipeline 1010. By increasing the number of sensor devices, i.e., more sensor devices at each height within the pipeline or more sensor devices within each layer, the accuracy of measurements can be increased.

Not only increasing the number of sensor devices, but also conducting measurements over multiple runs can further increase the accuracy of measurements. This way data collected by each sensor at each measurement run can be compared to other measurement runs conducted by the same sensor or other sensors. This may also be helpful in determining changes of the fluid and fluid conduit properties over a time period.

Figure 9:
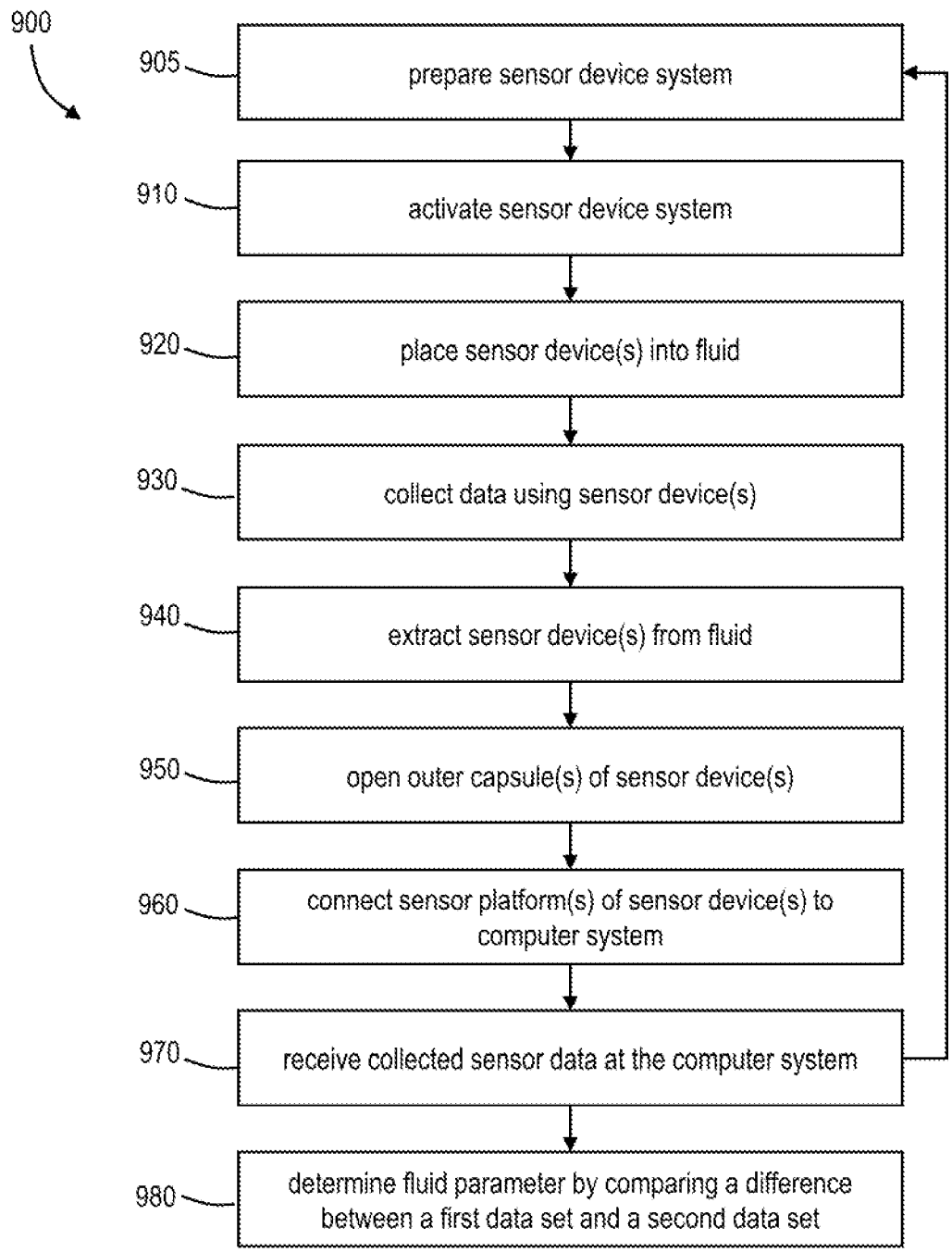
FIG. 9 is a flowchart of a method for collecting data, in accordance with an embodiment.

Reference is now made to FIG. 9, which depicts a flowchart of a method 900 for using a sensor device system for collecting fluid data and fluid conduit data, such as the one described with reference to FIG. 6 and FIG. 19, below. While the method depicted in FIG. 9 discloses the use of one sensor device, it will be understood that multiple sensor devices can be used to increase the amount of data available and to increase the accuracy of the fluid properties and fluid conduit properties determined by the method.

At 905, the sensor device system is prepared. Preparing the sensor system may involve connecting each sensor device to a computer system. Further details of such connections are disclosed below in relation to 960. Preparing the sensor device system may include changing the settings of each sensor device using the computer system. In other embodiments, the settings of each sensor device may be changed without a computer system. Settings may include, for example, how long a sensor device should wait after being activated before beginning to collect data. Settings may also include the range and sampling rate of each sensor. Preparing the sensor device system may also include erasing the data of each sensor device. Preparing the sensor device system may also include charging the power source of each sensor device. Where a plurality of sensor devices are used, 905 may include synchronizing the clocks of the sensor platforms of each sensor device. Alternatively, the clocks of the sensor platforms of each sensor device may be each be synchronized with an external clock. The synchronization may occur automatically, e.g., when each sensor device is connected to the computer system, or when the settings of each sensor device are changed.

At 910, the sensor device system is activated. Activating the sensor device system includes activating each sensor device of the sensor device system. This can be achieved by, for instance, using the activator unit (e.g. 500 at FIG. 5A or 700 at FIG. 15B) to send a signal across the conductors of each sensor device (e.g. 130a, 130b at FIG. 2A or 230a, 230b at FIG. 12). Alternatively, each sensor device could be activated using other mechanisms, such as magnets, a wireless signal, a sudden force, etc.

At 920, each activated sensor device is placed into the fluid. The fluid may be in a pipeline. In some pipelines, placing each activated sensor device into the fluid may involve placing each activated sensor device into an entry chamber connected to the pipeline, sealing the entry chamber from the outside, and then opening a hatch inside the pipeline to release each sensor device from the entry chamber into the pipeline. For example, as discussed in more detail below, the entry chamber may be a launching pigging valve that may be used for introducing a cleaning pig into the pipeline. The sensor device may be placed within the launching pigging valve and be entered the pipeline. If the fluid is a gas, the sensor may actually be mounted on a cleaning pig, as discussed below. Thereafter, the cleaning pig with the sensor mounted thereon can be introduced into the pipeline through the launching pigging valve. The sensor device can travel in the pipeline along with the cleaning pig.

In case the fluid is not in a pipeline, for example an open body of water such as a lake, the sensor can be placed on the surface of the fluid. Depending on where within the fluid measurements should be conducted, weight of the sensor device can be adjusted, e.g., by adjusting weights 160*a* and 160*b*, so that the sensor device can buoy at a desired vertical location or flow within the fluid at that vertical location.

At 930, each activated sensor device collects data from the fluid. This data may include, for instance, accelerometer data, gyroscopic data, and magnetometer data. Pressure, and/or temperature data may also be collected. In addition, as discussed in more detail below, acoustic data may also be collected. The fluid properties and fluid conduit properties are sensed with the sensor device that flows freely along a path of a fluid conduit and the collected fluid data and fluid conduit data is stored as a first fluid dataset. The activated sensor device may collect data from the fluid while conveyed by the fluid along a specific path through a fluid conduit. For example, the specific path may correspond to the flow path established by a pipeline. The specific path need not be exact line, and may be defined by a region of highest probability with regard to the path a fluid is expected to take through a fluid conduit. The specific path may also include chaotic elements, such as a turbine blade disposed along the length of the fluid conduit, a spool, a multi-section bend, a jumper section, a valve, etc. as discussed in more details in relation to FIGS. 16A-18D, below.

Each sensor device may be configured to collect data at regular time intervals. For example, each sensor device may be configured to collect accelerometer data at a constant rate of between 10 samples per second and 2000 samples per second. Data may also be collected by different sensors in the same sensor device at different intervals. For example, the magnetometer of a sensor device may collect data at a constant rate between 0.1 samples per second and 100 samples per second, while the gyroscope of the same sensor device collects data at a constant rate between 10 samples per second and 1000 samples per second.

The data may be recorded by each sensor device such that each value is represented by a 16-bit number. In other embodiments, a higher or lower bit length, such as 32 or 8 bits, could be used to increase or decrease the precision of the data. The precision of the data may also be increased by adjusting the scale of the recorded values. For example, if a sensor device is not expected to be subject to accelerations exceeding 4 g, that sensor device could be configured such that each of the $2^{16}$ possible values of a 16 bit number corresponds to a single acceleration value between 0 and 4 g. If, on the other hand, the sensor device is not expected to be subject to accelerations exceeding a lower value of 2 g, the precision of the accelerometer data could be increased by configuring the sensor device such that each of the $2^{16}$ possible values of a 16-bit number corresponds to a single acceleration value between 0 and 2 g—a smaller range.

Each sensor device may also be configured to delay data collection for some predetermined interval or after a triggering signal (e.g. a reading from the magnetometer of a ferromagnetic element), such that data collection does not begin immediately when the sensor device is activated. For example, each sensor device could be configured to begin collecting data 3600 seconds, more or less, after being activated. Alternatively, each sensor device could be configured to begin collecting data 20 minutes, more or less, after being activated, which may be advantageous if, e.g., it will take that sensor device up to 20 minutes to be conveyed by the fluid to an area of interest.

At 940, each activated sensor device is extracted from the fluid. Each sensor device may be extracted from the fluid after a certain time has elapsed from when it was placed into the fluid. Each sensor device may continue to collect data when it is extracted. In other embodiments, each sensor device may have ceased collecting data before it is extracted. If a sensor device is still collecting data when it is extracted, 940 may optionally include deactivating that sensor device, e.g., by sending a signal across the conductors of that sensor device (e.g. 130*a*, 130*b* at FIG. 2A) using an activator unit (e.g., 500 of FIG. 5). If the sensor device was placed in a pipeline, it may be extracted through a receiving pigging valve, as discussed in more detail below in relation to FIGS. 16-18D.

At 950, the fluid-resistant outer capsule of each sensor device is opened. The outer capsule is opened in order to gain access to the sensor platform of each sensor device. In some embodiments, this may involve unscrewing or unfastening the conductors (e.g. 130*a*, 130*b* at FIG. 2) of each sensor device. In other embodiments, the sensor platform may be able to interface with a computer system using the conductors of each sensor device (e.g. 130*a*, 130*b* at FIG. 2) or wirelessly, and 950 may be unnecessary.

At 960, the sensor platform of each sensor device is connected to a computer system. The computer system may be a computer, a laptop, or any computing device capable of receiving data from the sensor platform of each sensor device. In some embodiments, the sensor platform of each sensor device may be connected to a computer system via a cradle (e.g. 400 at FIG. 4A) fitted to the inner frame (e.g. 120 at FIG. 3C) of each sensor device. In alternative embodiments, each sensor platform may be connected to the device by the use of a USB port (e.g. 221 at FIG. 13A) provided with that sensor platform. Alternatively, the sensor device may have a removable memory card, e.g., a micro SD card, placed in a memory card slot (e.g., 266 at FIG. 13B). The memory card may be removed from the memory card slot and be received by the computer.

At 970, the computer system receives data from each sensor platform. The data may be received in binary form, or may be received as comma separated values (CSV). In other embodiments, other data formats can be used. The computer system may include readout software for processing the data and/or presenting it in real-time.

At 980, at least one fluid parameter is determined from the data received from each sensor platform. The fluid parameter may include information about the system that the fluid is passing through, such as fluid conduit data.

The determination may be performed on the computer system. In other embodiments, the determination may have already been performed by the sensor device. Examples of fluid parameters include those relating to flow dynamics: the flow speed, whether there is laminar flow, whether there is turbulent flow, wave patterns, the existence of sedimentation ("waxing"), the existence of air pockets, pipe diameter changes, the existence of flow-interrupting artifacts in a pipeline, the position of corners, the position of flow-ups in a pipeline, the position of flow-downs in a pipeline, etc. The fluid parameter might have a value that changes over time, or may have a single value calculable for any particular subset of the received data.

After waiting a period of time, the method may include sensing fluid properties and fluid conduit properties with the sensor system again, e.g., along the same specific path as that of a first fluid dataset, and storing the collected fluid data as a second fluid dataset. The first fluid dataset would then be compared with the second fluid dataset to determine at least one fluid conduit property. A fluid property may be calculated by comparing a recently determined fluid parameter to a fluid parameter determined at a past time. This comparison may take place for fluid parameters corresponding to a specific path through a fluid conduit, taken by each sensor device during collecting fluid data at 930. This comparison can provide information on new blockages in a pipeline, for instance, or an increased need for maintenance in a particular area of interest. Generally, aspects of this process can be repeated over time to generate a plurality of fluid datasets (i.e. of data collected by the sensor system for the same specific path at different times), and this plurality of fluid datasets may be stored in a fluid database. The fluid database may then be used and analyzed to better understand flow and pipeline dynamics. Analysis of the fluid database may also lead to predictive capabilities on pipeline failure and may inform pipeline design.

The fluid parameter may include leak detection. A sensor for leak detection may measure the vibration of the device outer capsule to determine the acoustic properties of the fluid and fluid conduit at a given location. The acoustic properties can be used to detect a fluid leak in the conduit as discussed in more detail below with respect to FIGS. 12-13C and FIGS. 16A to 18D.

In embodiments with a plurality of sensor devices, a fluid parameter can be determined from the data of received from a set of sensor platforms. For example, a fluid parameter may be determined by averaging several corresponding data values received from each of the set of sensor platforms. A fluid parameter may also be determined by taking quartiles, finding the maximums or minimums, and/or performing other statistical analyses of these corresponding data values.

Figure 10A:
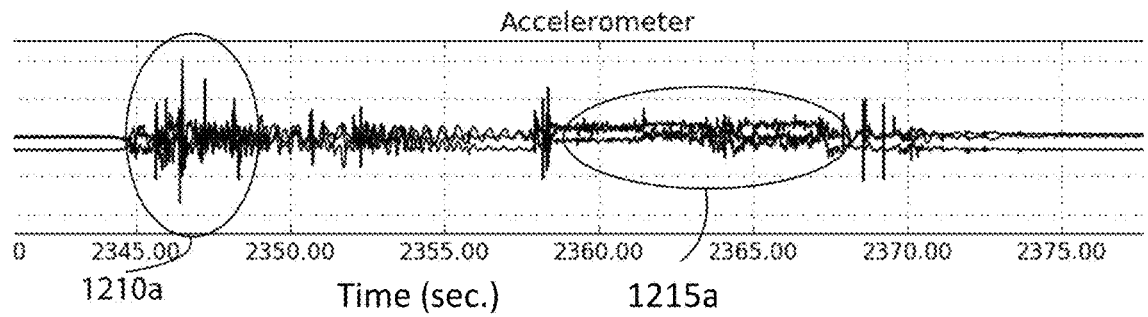
FIGS. 10A-10R are graphs of acceleration, gyroscopic, and magnetic measurements, collected by a sensor device, in accordance with an embodiment.
Figure 10B:
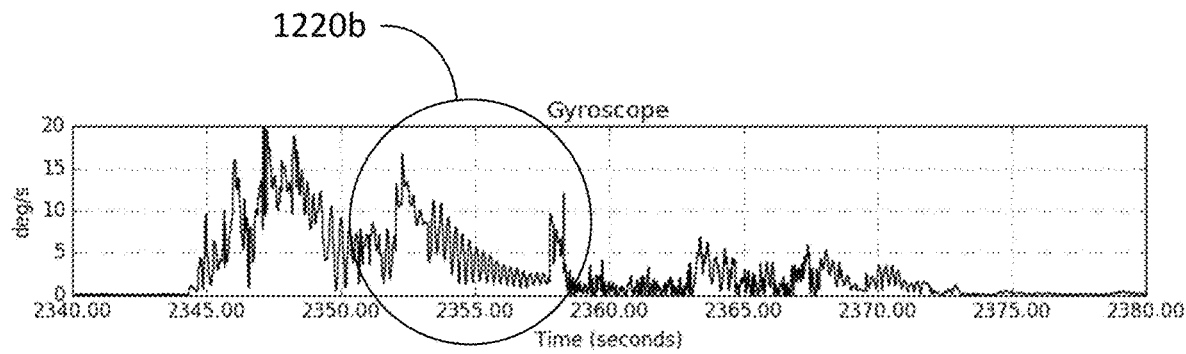
Figure 10C:
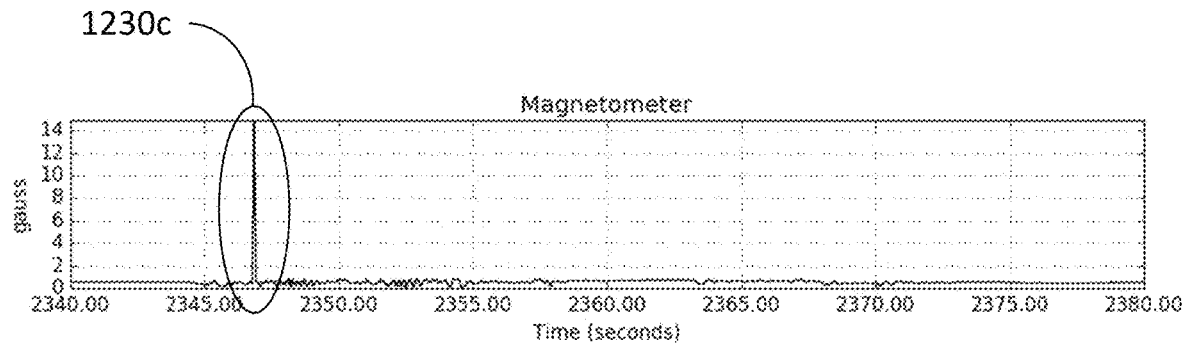
Figure 10D:
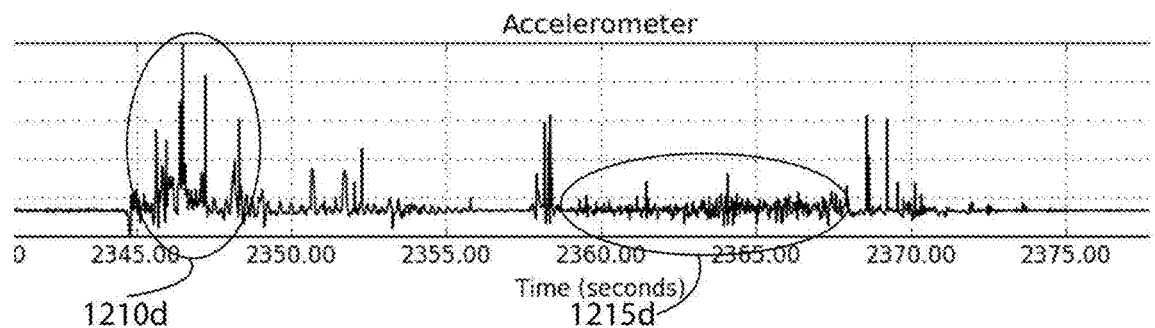
Figure 10E:
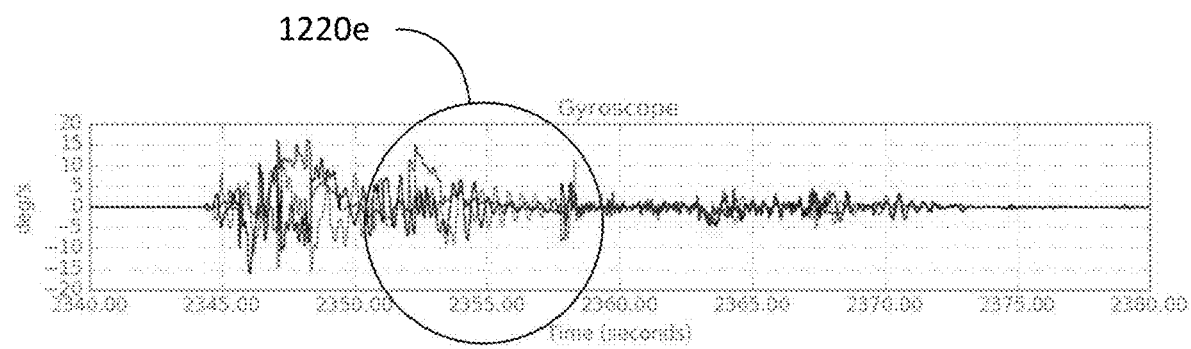
Figure 10F:
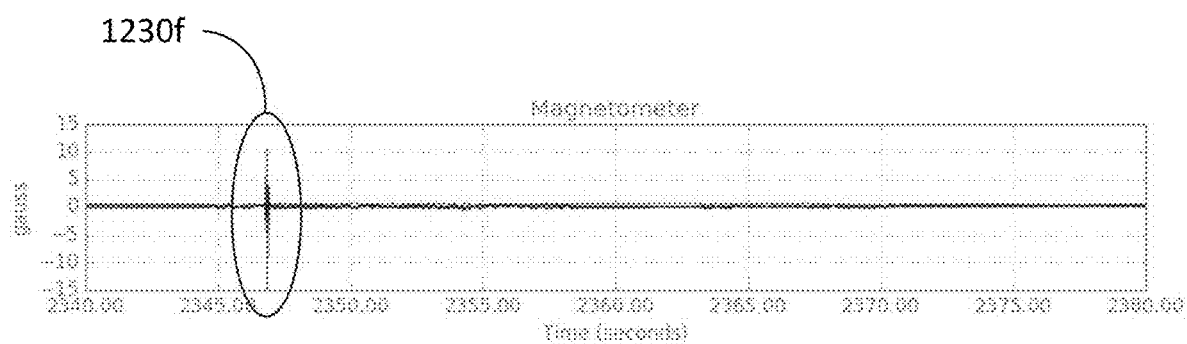
Figure 10G:
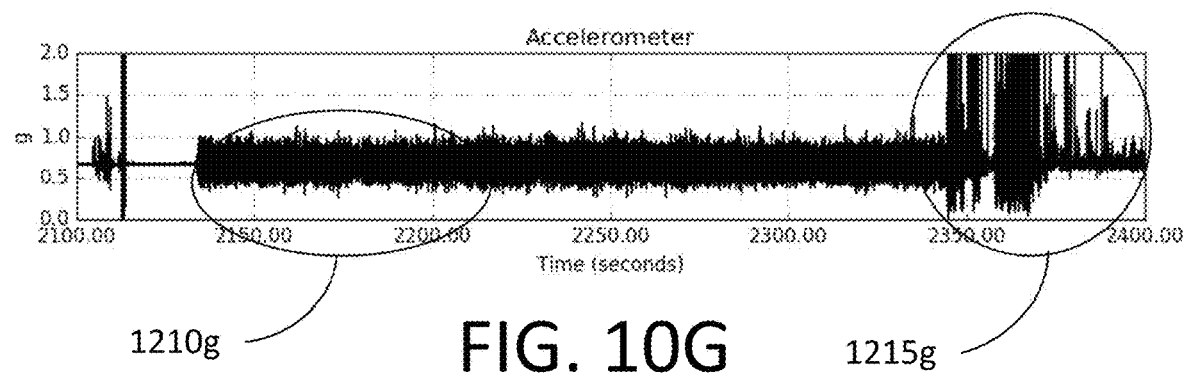
Figure 10H:
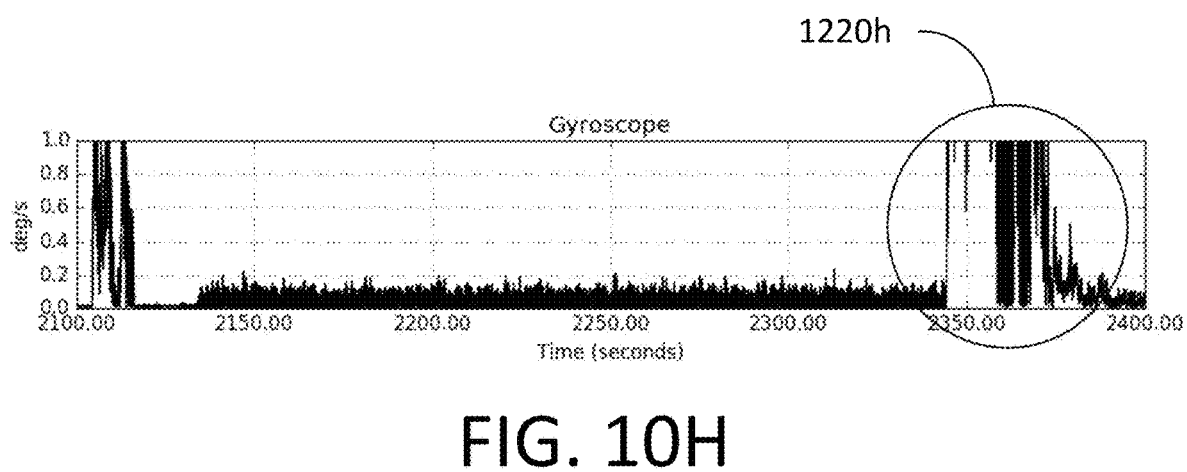
Figure 10I:
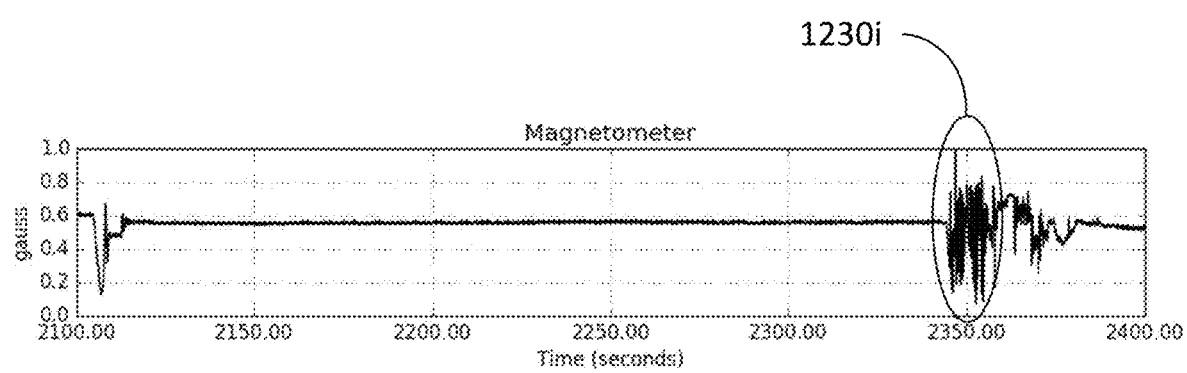
Figure 10J:
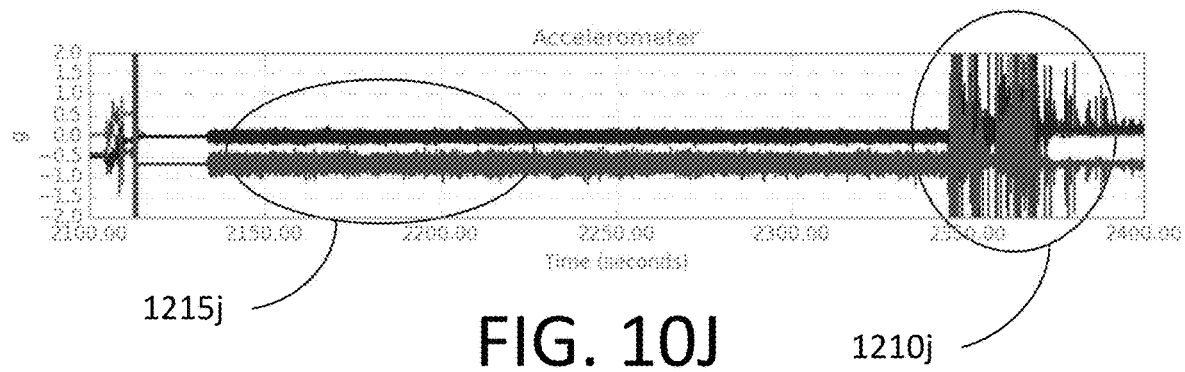
Figure 10K:
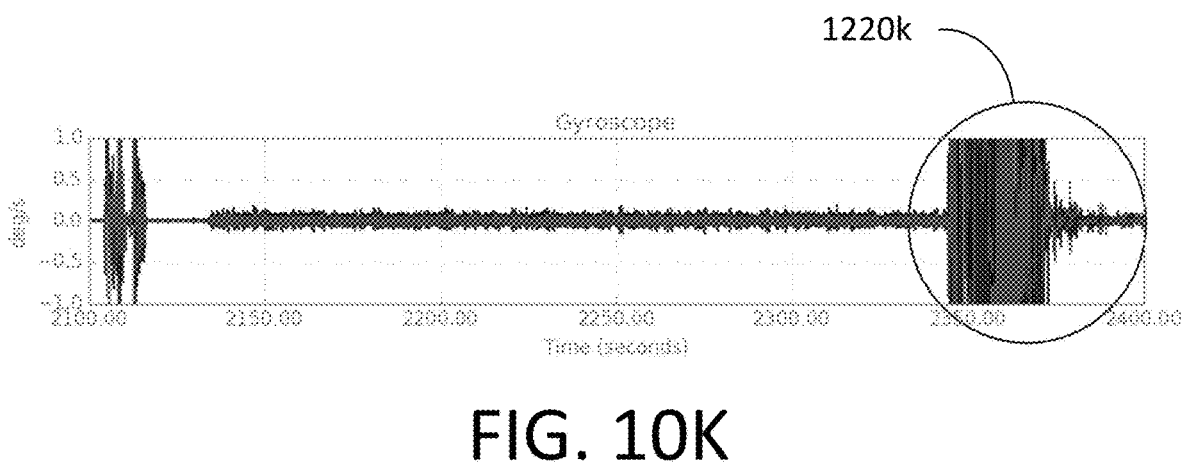
Figure 10L:
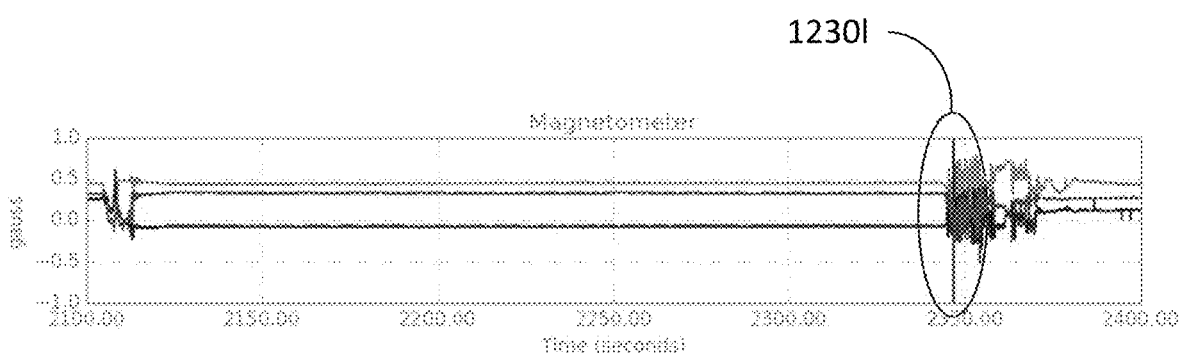
Figure 10M:
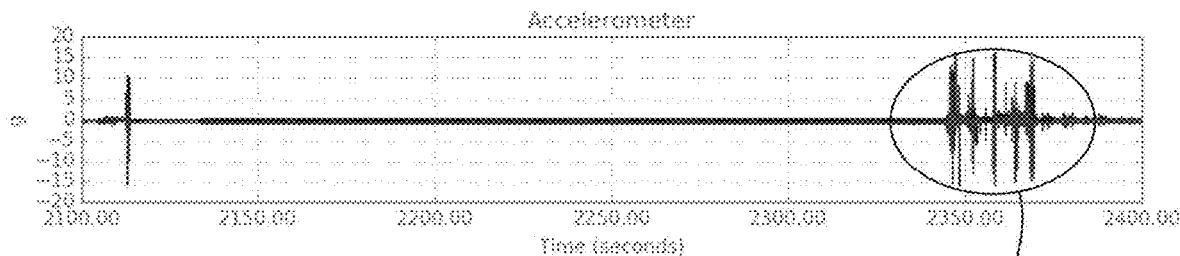
Figure 10N:
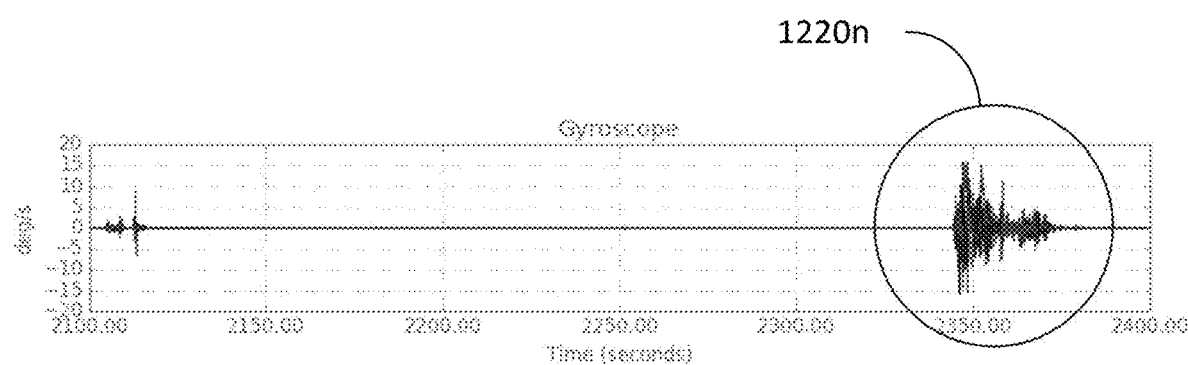
Figure 10O:
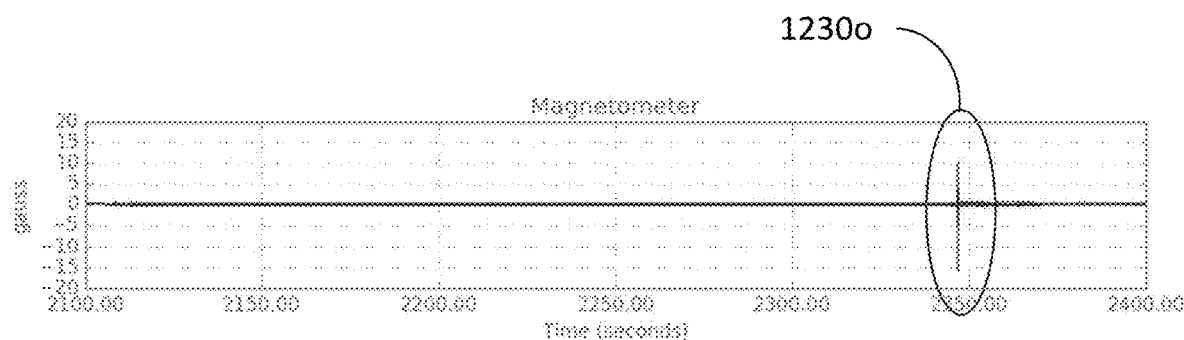
Figure 10P:
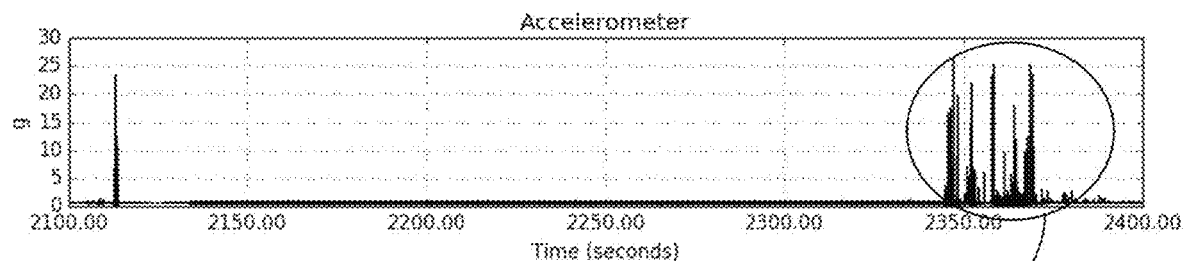
Figure 10Q:
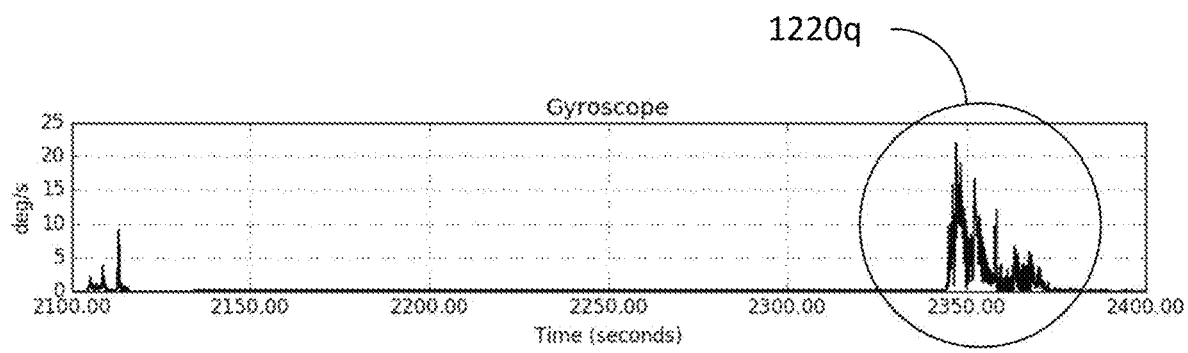
Figure 10R:
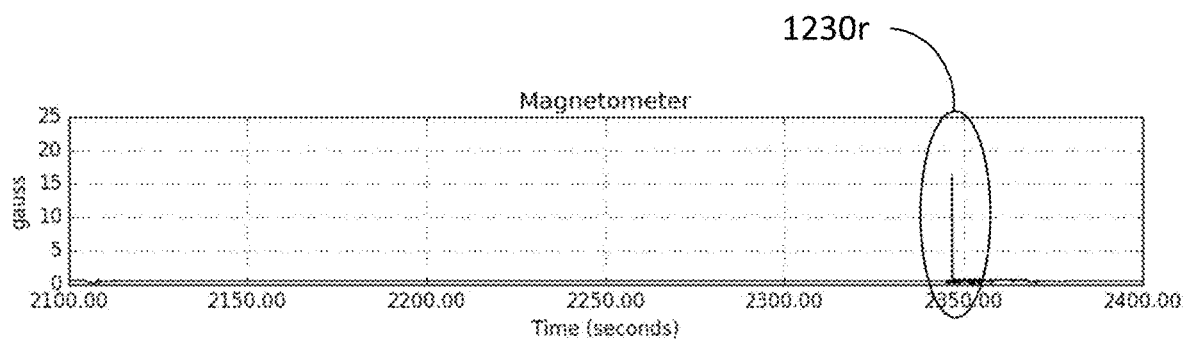

Reference is now made to FIGS. 10A-R, which depict examples of data collected by a sensor device system for collecting fluid data, such as the sensor system 600 described with reference to FIG. 6. FIGS. 10A-C, 10G-I, and 10P-R are graphs of the magnitudes of the resultant vectors calculated from the triaxial data depicted in the graphs of FIGS. 10D-F, 10J-L, and 10M-O, respectively.

FIGS. 10A, 10D, 10G, 10J, 10M, and 10P show examples of accelerometer data, collected by a sensor device at regular time intervals. Regions 1210a and 1210d show many sudden accelerations, may indicate a turbulent flow. A turbulent flow may in turn indicate sediment or an obstruction in the path of fluid flow. An individual peak or set of peaks in accelerometer data may be indicative of a collision, which could be caused by directional changes or obstructions in the fluid path. Regions 1215a and 1210d show a more constant acceleration, may, in contrast, indicate a region of more laminar flow, with fewer obstructions in the path of fluid flow. The accelerometer data may include forces on the accelerometer caused by gravity. This accelerometer data may be used, on its own or combined with data from other sensors, to determine the orientation of the sensor device. A region of no gravitational acceleration may be indicative of a free fall of the sensor device through a fluid.

Region 1210g in FIG. 10G and region 1215j in FIG. 10J shows a stronger accelerometer response compared to the part before, as this is the moment where the flow is on, but the sensor device is not yet flowing through the loop.

Looking at FIGS. 10M, 10N, 10P and 10Q, regions 1210m, 1220n, 1215p and 1220q show the run. This illustrates stronger signals in the accelerometer and gyroscope, as the sensor device flows through the loop.

Regions 1210a and 1215a in FIG. 10A and regions 1210d and 1215d in FIG. 10D are examples of turbulent versus laminar flow. Regions 1210a, and 1210d showing many sudden accelerations and regions 1215a and 1215d show a more constant acceleration.

FIGS. 10B, 10E, 10H, 10K, 10N, and 10Q show examples of gyroscope data, collected by a sensor device at regular time intervals. Regions 1220b and 1220e, 1220h show dampened rotational oscillation, may indicate that the fluid flow had recently changed direction but is now stabilizing after such an event. As with regions of many sudden accelerations described above, regions of many sudden changes in sensor device orientation may also be indicative of a turbulent flow. This, in turn, may be because the sensor device has passed through a curved section of pipeline, or an obstacle in the fluid flow, or a shockwave.

FIG. 10C, 10F, 10I, 10L, 10O, and 10R show examples of magnetometer data, collected by a sensor device at regular intervals. Regions 1230c, 1230f, 1230i, 1230l, 1230o, and 1230r, showing a peak in magnetic field strength, may correspond to the event of the sensor device passing a ferrous flange or some other magnetic marker (e.g. a magnetic flow meter or pump) placed along the path of fluid flow. The magnetic field of the Earth may also appear in the magnetometer data. Changes in the strength of the measured magnetic field of the Earth may correspond to changes in the type of structure that each sensor device is passing through. The magnetic field of the Earth may also present directional components, which may be further analyzed to get an indication of orientation of each sensor device (i.e. relative to the Earth).

Region 1220n in FIG. 10N and region 1220q in FIG. 10Q indicate the full run (as region 1210m in FIG. 10M and region 1215p in FIG. 10P for the accelerometer). Looking at the zoomed in FIGS. 10K and 10H of FIGS. 10N and 10Q respectively, there is an increased response in the gyroscope at the same time of the increased response in the accelerometer indicated by 1210g in FIG. 10G and 1215j in FIG. 10J. This again shows that the flow is turned on but the sensor device is not flowing through the loop yet. The dampened oscillation is shown at region 1220b in FIG. 10B and region 1220e in FIG. 10E.

Regions 1215g, 1220h, 1230i, 1210j, 1220k and 12301 in FIGS. 10G-L, again highlight the run which is highlighted by regions 1210m, 1220n, 1215p and 1220q.

As a brief summary of some of the data phenomena and analyses described above: (1) spikes in the accelerometer data are indicative of collisions which could be caused by directional changes or obstructions in the fluid path; (2) irregular behavior in the gyroscope data (and potentially the accelerometer data) can be used to distinguish between laminar and turbulent flows; (3) regular dampening patterns in the gyroscope data may be indicative of a sensor device that is stabilizing after a distortion which may have been caused by, e.g., a directional change or hitting a bend; (4) sharp peaks in the magnetometer graph are indicative of a source of strong magnetic fields, such as a magnetic flow meter or pump or a ferrous material; (5) regular patterns in each of the sensors are indicative of the dynamics of the fluid, and may capture, e.g., the frequency of certain waves in the fluid; (6) the effects of gravity and the Earth's magnetic field are generally expected to appear in the data; (7) the absence of gravity in the data may be indicative of a free fall; (8) changes in the readings caused by Earth's magnetic field may provide information about the type of structure the sensor device is passing through; and (9) data collected from the Earth's magnetic field may have directional components that may be used to get an indication of the orientation of the sensor device. The magnetic field of the Earth may only be visible when not shielded e.g., by the pipeline. Where the Earth's magnetic field is shielded, other indicators such as the magnetization of the pipeline may be used.

Figure 11:
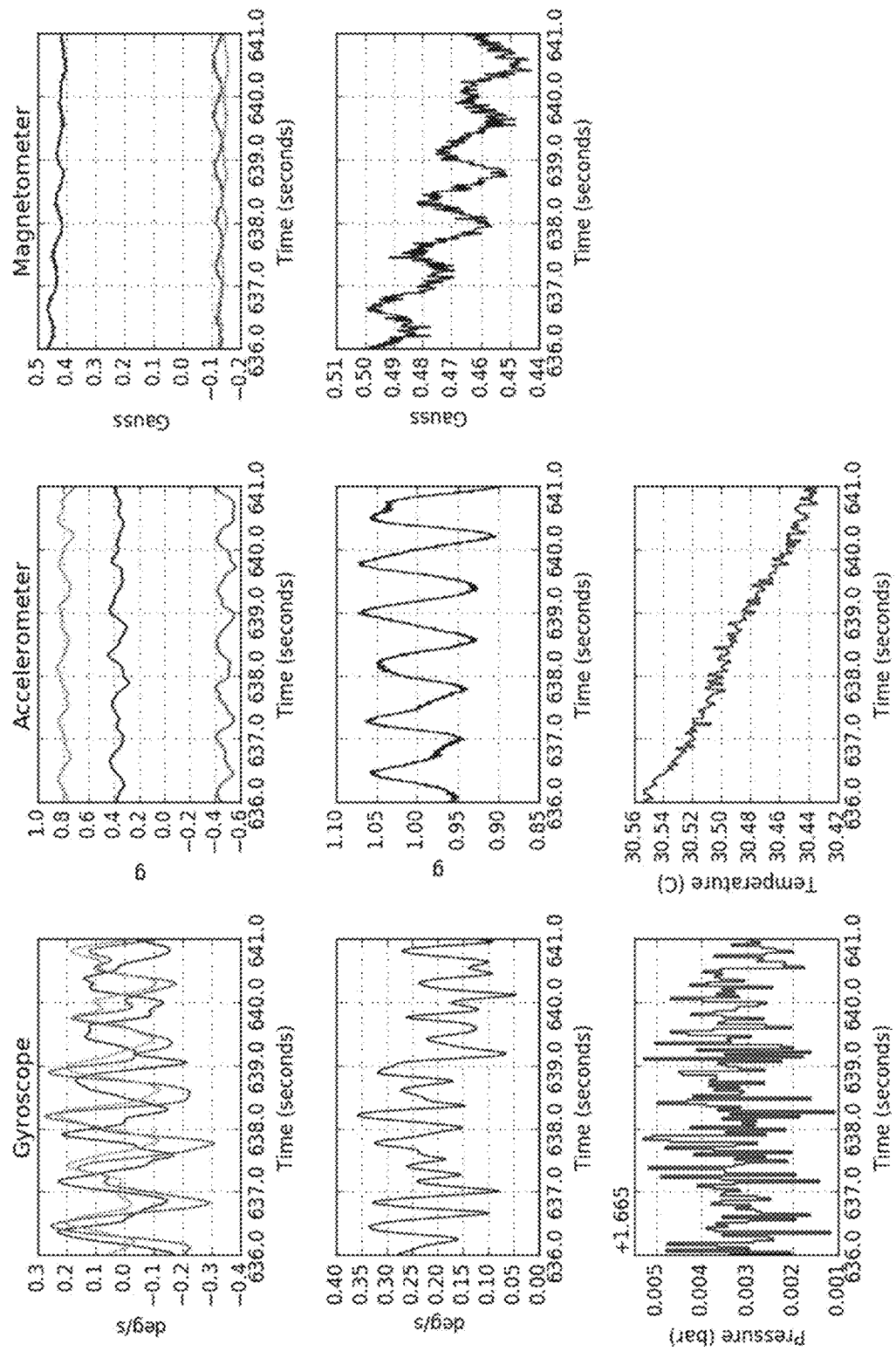
FIG. 11 is a set of graphs of acceleration, gyroscopic, magnetic, pressure, and temperature data collected by a sensor device, in accordance with an embodiment.

Reference is now made to FIG. 11, which depicts several graphs of data collected by several sensors of a sensor device over a time period. The first row of graphs includes triaxial data collected by the gyroscope, accelerometer, and magnetometers. The second row of graphs includes the magnitudes of resultant vectors calculated from the triaxial data of the first row of graphs. The third row of graphs include pressure and temperature data collected concurrently with the gyroscope, accelerometer, and magnetometer data of the first two rows of graphs.

Reference is now made to FIGS. 12 and 13A-C, illustrating a sensor device 200 and its components in accordance with another embodiment. The sensor device 200 is similar to the sensor device 100, described above, with the exception of the differences discussed below. To avoid repetition, similarities are not discussed. Accordingly, other than below-discussed differences, everything said heretofore about the sensor device 100 may apply to the sensor device 200 as well.

In FIGS. 12 and 13A-C, like elements as in FIGS. 1-3F is referred to with like reference numbers incremented by 100. In other words, if an element of the sensor device 100 is referred to by reference number 1XX and this element has a counterpart in the sensor device 200, the counterpart element in the sensor device 200 is referred to by reference number 2XX.

Figure 12:
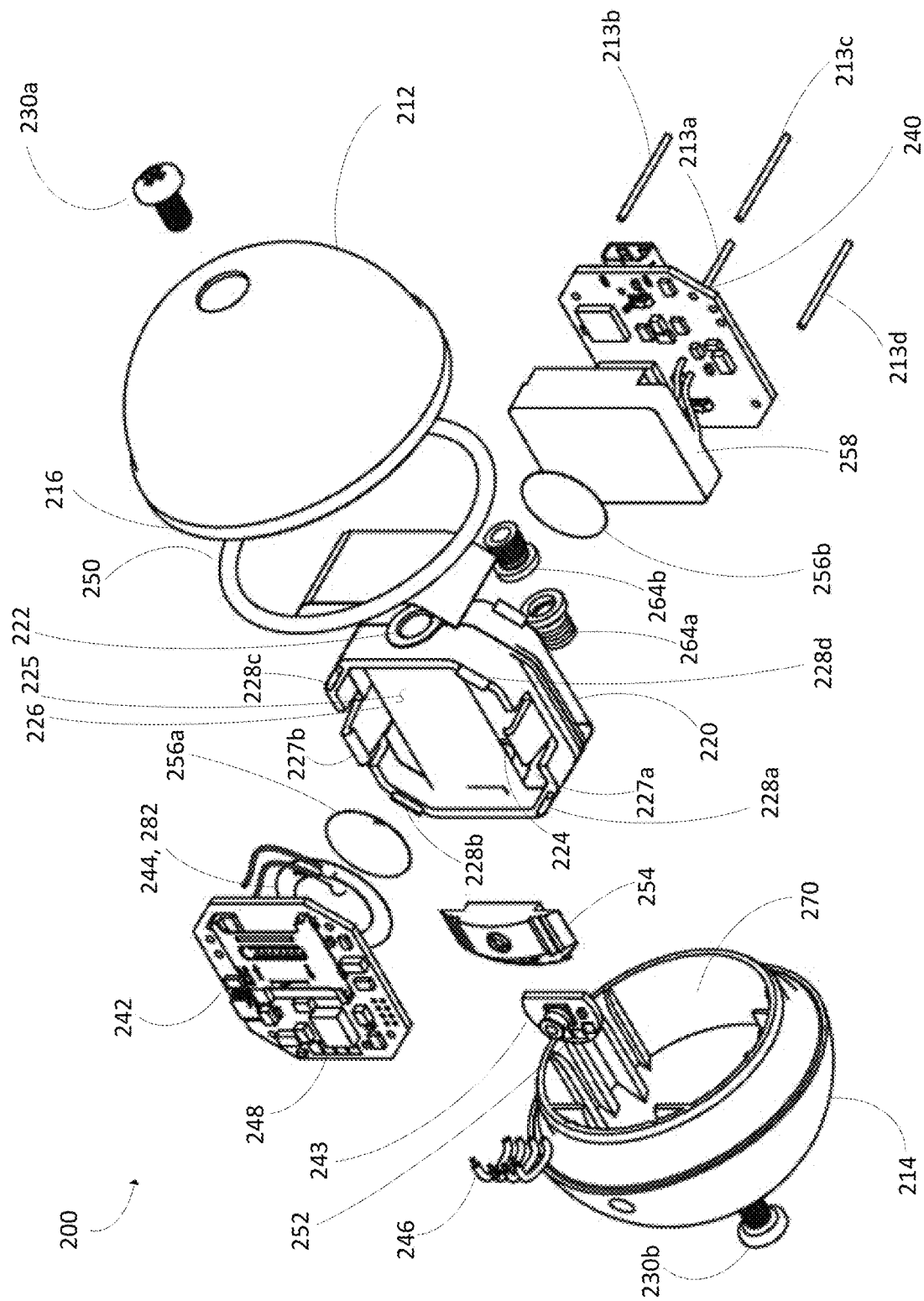
FIG. 12 is an exploded view of a sensor device, in accordance with another embodiment.

Referring to FIG. 12, in the example illustrated, the sensor device 200 includes an outer capsule including a first capsule portion 212 and a second capsule portion 214 for providing fluid-tight containment to an interior compartment 270. The first capsule portion 212 and the second capsule portion 214 meet at a capsule seam 216. The first and second capsule portions 212, 214 enclose the interior compartment 270. The first and second capsule portions 212, 214 can be separated to provide access to the interior compartment 270. The sensor device 200 includes conductors 230a and 230b that can also act as fasteners to fasten the first capsule portion 212 to the second capsule portion 214, as discussed below. The outer capsule, when assembled, is fluid-tight and/or pressure-resistive.

Referring still to FIG. 12, the sensor device 200 includes an O-ring 250 for sealing the outer capsule seam 216. The sensor device 200 can include other O-rings for sealing other apertures in the outer capsule, the first capsule portion 212 and the second capsule portion 214. Similar to the outer capsule 110, the outer capsule of the sensor device 200, in other examples, may be made fluid-tight and/or pressure-resistive using seals other than the O-ring 250 such as, for example, glue or thread seal tape. In other embodiments, the outer capsule of the sensor device 200 may be made effectively fluid-tight and/or pressure-resistive by pressuring the interior compartment 270. In other embodiments, the outer capsule of the sensor device 200 may not be perfectly fluid-tight and/or may not be pressure-resistive, and the contents of the interior compartment 270 may be protected, such as, for example, using conformal coating (e.g. 129 at FIG. 3C) to provide fluid resistance to the components in the interior compartment 270.

Similar to the sensor device 100, the sensor device 200 may also include one or more weights (not shown), such as weight 160a and weight 160b shown with respect to the sensor device 100, for adjusting the mass and center of gravity of the sensor device 200.

Figure 13A:
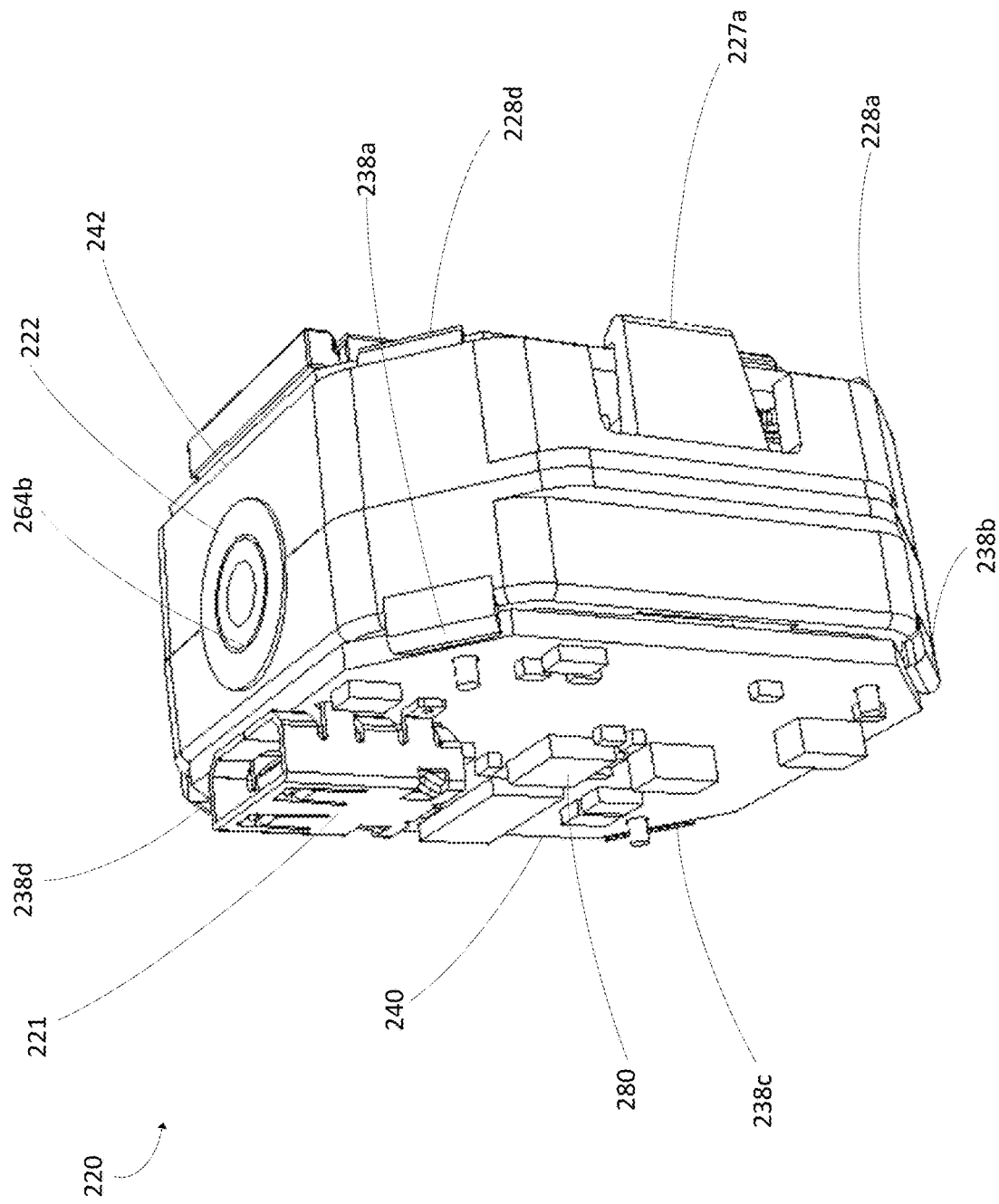
FIG. 13A is a perspective view of an inner frame and a sensor platform of the sensor device of FIG. 12.
Figure 13B:
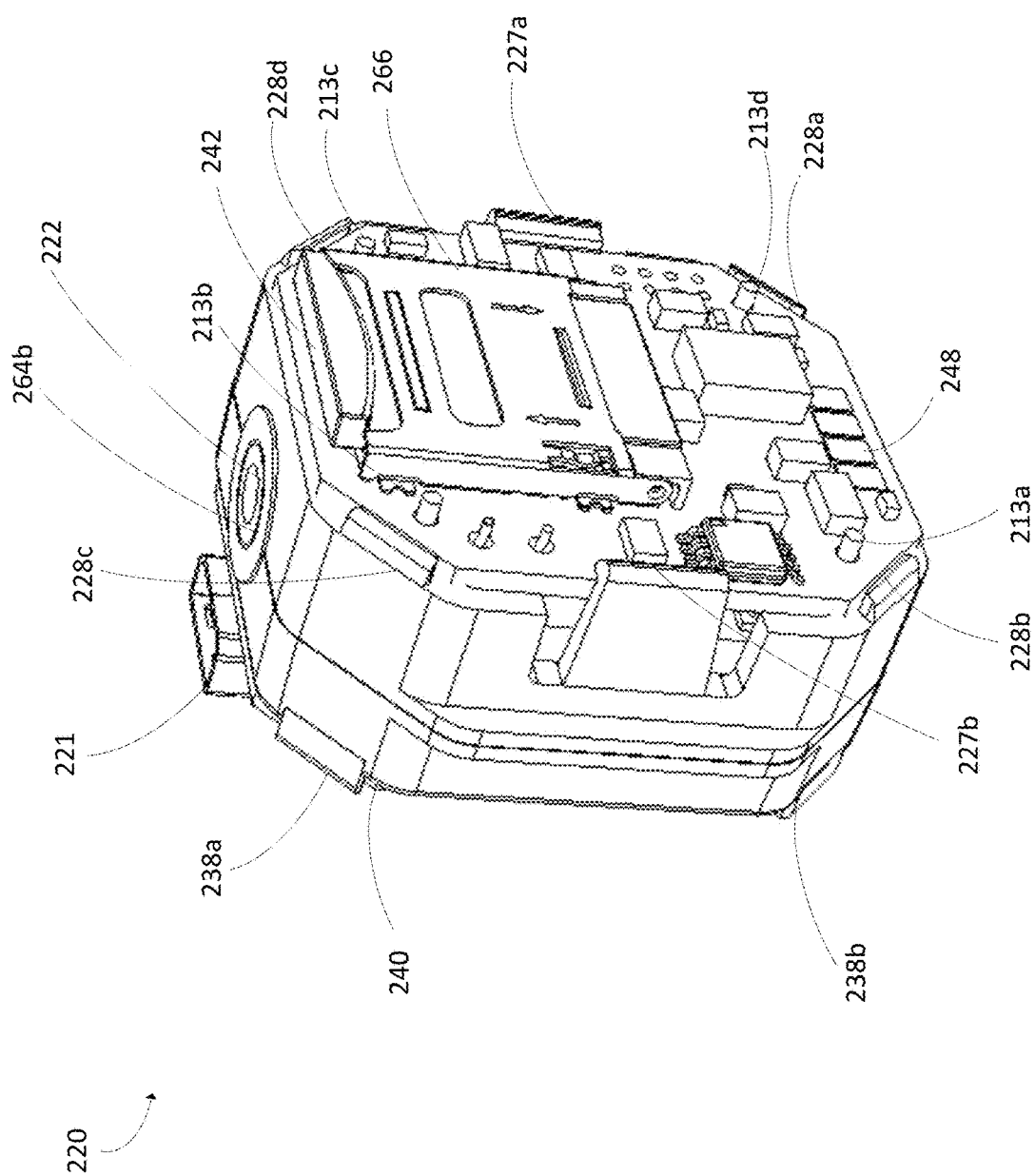
FIG. 13B is a perspective view of the inner frame and an acoustic sensor platform of the sensor device of FIG. 12.

Referring still to FIGS. 12 and FIGS. 13A-13B, the sensor device 200 includes at least one sensor 280, similar to the sensor 180 of the sensor device 100, and an acoustic sensor 244 for sensing acoustic properties of the fluid and fluid conduit. The acoustic sensor 280 may be, for example, a piezo transducer.

The sensor device 200 may include a pressure-temperature sensor 243 for sensing both pressure and temperature.

In this embodiment, the acoustic sensor 244 includes a piezo transducer 282 mounted to the acoustic sensor 244 through an epoxy resin 256a. The piezo transducer 282 converts the vibration of the outer capsule of the sensor device 200 to electrical signals as known in the art. Electrical signals are received by the acoustic sensor 244 for further processing. The acoustic sensor 244 can be used for, e.g., detecting presence of a leak within the fluid conduit and size of the detected leak, as discussed in more detail below.

In this embodiment, the sensor device 200 includes a sensor platform 240, similar to the sensor platform 140 of the sensor device 100. In addition to the sensor platform 240, the sensor device 200 includes an acoustic sensor platform 242 for the acoustic sensor 244. The acoustic sensor platform 242 can provide electronics for signal condition, digitizing, processing compressing and/or storing data related to the acoustic sensor 244. In other words, the acoustic sensor platform 242 may provide a processing unit separate from and/or in addition to the sensor platform 240 for the acoustic sensor 244, thereby increasing the versatility and computing power of the sensor device 200. The acoustic sensor platform 242 may be provided on a printed circuit board with soldered components, similar to sensor platforms 140, 240.

Referring to FIG. 12, after both physically and electrically connecting the piezo transducer 282 through the epoxy resin 256a and its wires, respectively, to the acoustic sensor 244, internal connectors 252 of the acoustic sensor 244 are connected to internal connectors 248 of the acoustic sensor platform 242 through wires 246. An epoxy resin 254 attaches the acoustic sensor 244 underneath the acoustic sensor platform 242. In other embodiments, other types of electrical and physical connections, other than wires and epoxy resins, may be used, as known in the art and as described heretofore with respect to the sensor device 100.

In the embodiment illustrated in FIG. 12, the conductors 230a and 230b are in electrical communication with both the sensor platform 240 and the acoustic sensor platform 242. The conductors 230a and 230b are exposed on the surface of outer capsule of the sensor device 200, so as to allow signals to be sent to and/or received from the sensor platform 240 and the acoustic sensor platform 242 for, e.g., activating the sensor 280 and the acoustic sensor 244. While the sensor device 200 uses two conductors, in other embodiments, different number of conductors may be used.

The sensor device 200 also includes on an inner frame 220, which can be physically installed in and removed from the interior compartment 270. In this example, the inner frame 220 includes a plate element 226 with a first non-conductive surface 225 and a second non-conductive surface (not shown) opposite the first non-conductive surface 225. Both the acoustic sensor platform 242 and the sensor platform 240 are mounted on the inner frame 220. The inner frame 220 provides a conduit for the conductors 230a, 230b to activate the sensor 280 and the acoustic sensor 244 via the sensor platform 240 and acoustic sensor platform 242, respectively.

In the embodiment illustrated in FIGS. 12 and 13A-C, the conductors 230a and 230b include fasteners to close the first capsule portion 212 to the second capsule portion 214. The fasteners are threaded bolts that are received in multi-purpose threaded inserts (multiserts) 264b and 264a inserted within bores 222 and 224, respectively, of the inner frame 220. The conductors 230a, 130b close the first capsule portion 212 to the second capsule portion 214 by each attaching the respective capsule portion 212, 214 to the inner frame 220. In other embodiments, the first capsule portion 212 and the second capsule portion 214 may be closed using fitted self-locking grooves disposed along the outer capsule seam 216. In other embodiments, the conductors 230a and 230b may not be necessary to close the first capsule portion 212 to the second capsule portion 214.

Referring still to FIGS. 12 and 13A-C, the inner frame 220 provides a frame for mounting the sensor platform 240 and the acoustic sensor platform 242. The inner frame 220 includes clips 227a, 227b and spacing ridges 228a, 228b, 228c, 228d for holding the acoustic sensor platform 240 in place. The inner frame 220 also includes clips 238a, 238b, 238c, 238d for holding the sensor platform 240 in place.

Referring specifically to FIG. 13B, the spacing ridges 228a, 228b, 228c, 228d prevent the acoustic sensor platform 242 from sliding out from under the clips 227a, 227b. The clips 227a, 227b may be the only elements that hold the acoustic sensor platform 242 in place, such that no other component is needed to affix the sensor platform 242 to the inner frame 220, increasing the simplicity of the design of the inner frame 220. The clips 227a and 227b can be similar to the clips 127a, 127b.

In the embodiment illustrated, the sensor platform 240 is prevented from sliding out of the inner frame 220 by clips 238a, 238b, 238c, 238d. In other embodiments, the inner frame 220 may have different clip configurations for securing the sensor platform 240. In other embodiments, the sensor platform 240 and the acoustic sensor platform 242 may be affixed to the inner frame 220 using, for example, glue, fasteners, etc., or may form a part of the inner frame 220 itself.

In this embodiment, the inner frame 220 also includes a plate element 226 for separating the acoustic sensor platform 242 from other components, such as a power source 258 and the sensor platform 240. The plate element 226 may include a non-conductive surface 225, to protect the circuitry of the acoustic sensor platform 242 and/or to prevent shorting with the power source. The acoustic sensor platform 242 sits on the non-conductive surface 225 while the sensor platform 240 sits atop the power source 258 which itself attaches to a surface opposite the non-conductive surface 225 of the plate element 226 via an epoxy resin 256b. In other embodiments, the power source 258 may be attached to the plate element 226 through other means known in the art or described in relation with the sensor device 100.

In some embodiments, the inner frame 220 may also include a back plate for securing the power source 258 to the inner frame 220, and/or to protect the power source 258. The back plate may be glued to the body of the inner frame 220, or may snap in place and/or be removed to service the power source. In the example illustrated, the power source 258 is a 3.7 lithium polymer battery. In other examples, the power source may be of any other types and configurations. In the example illustrated, the power source is in electrical contact with the acoustic sensor platform 242 and sensor platform 240 through four bus bar wires 213a, 213b, 213c, 214d. In other embodiments, any other suitable electrical connection known in the art may be used.

Figure 13C:
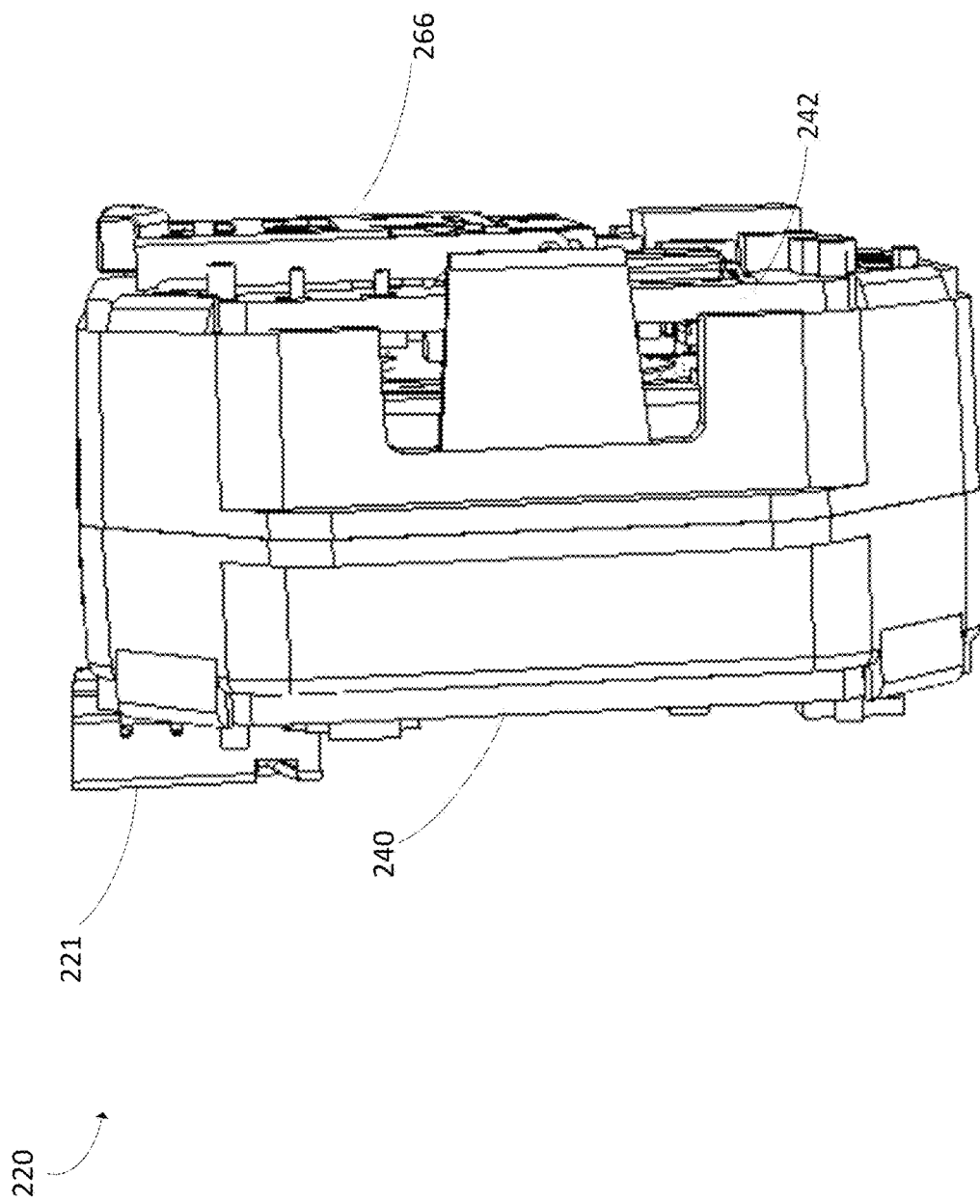
FIG. 13C is a side view of the inner frame, the sensor platform and the acoustic sensor platform of the sensor device of FIG. 12.

Referring to FIGS. 13A-C, the sensor platform 240 includes a USB port for communicating with a USB cable (e.g., the proprietary cable 300 shown in FIGS. 14A and 14B, discussed below) for, e.g., charging the power source 258, receiving instructions from an external computer system (such as computer system 2360 of FIG. 19), transmitting data to the external computing device, testing the sensor 280, etc.

In the example shown in FIG. 13B, the acoustic sensor platform 242 includes a memory slot 266 for receiving a compatible removable memory card, e.g., a SD card so that the collected data, including acoustic data such as audio, can be stored, easily transferred or new instructions can be uploaded to the acoustic sensor platform 242. In other examples, other types of memory cards and memory card slots may be used. Alternatively, the acoustic sensor platform 242 may have its own USB port or any other types of connector and a fixed memory, as known in the art, for transmission of stored data on the fixed memory or instructions to and from the acoustic sensor platform 242. In other embodiments, the acoustic sensor platform 242 may be able to transmit its data and receive instructions through the USB port 221 of the sensor platform 240.

When equipped with the USB port 221, the inner frame 220 does not need to be removed from the interior compartment 270 to be inserted, e.g., into the cradle 400. By removing only the first capsule portion 212, a USB cable, such as cable 300 of FIG. 14A, may be connected to the USB port 221. In these embodiments, the connectors 231a and 231b need not to necessarily be fasteners since the inner frame 220 may be an integral part of, e.g., the second capsule portion 214. In these embodiments the first capsule portion 212 may threadedly engage the second capsule portion 214 to make the interior compartment 270 fluid-tight.

Other aspects of the sensor device 200 and its components such as the first capsule portion 212, the second capsule portion 214, the O-ring 250, the inner frame 220, the power source 258, the sensor platform 240, the at least one sensor 280, etc. may be similar to those described above in relation to the sensor device 100, both the illustrated embodiments, and possible other embodiments described above but not illustrated. As noted above, features such as weights 160a and 160b are not discussed in detail in relation to the sensor device 200. However, as said before, the sensor device 200 may also include all the features, components and elements described in relation to the sensor device 100. For example, in some embodiments, the sensor device 200 may also have an external-facing pressure sensor similar to the sensor 142 installed in an aperture in one the first and/or second capsule portions 212 and 214, such as aperture 145 of the sensor device 100. As an another non-limiting example, in some embodiments, the shape and size of the sensor device 200 may be similar to the shape and size specification discussed above in relation to the sensor device 100.

Figure 14A:
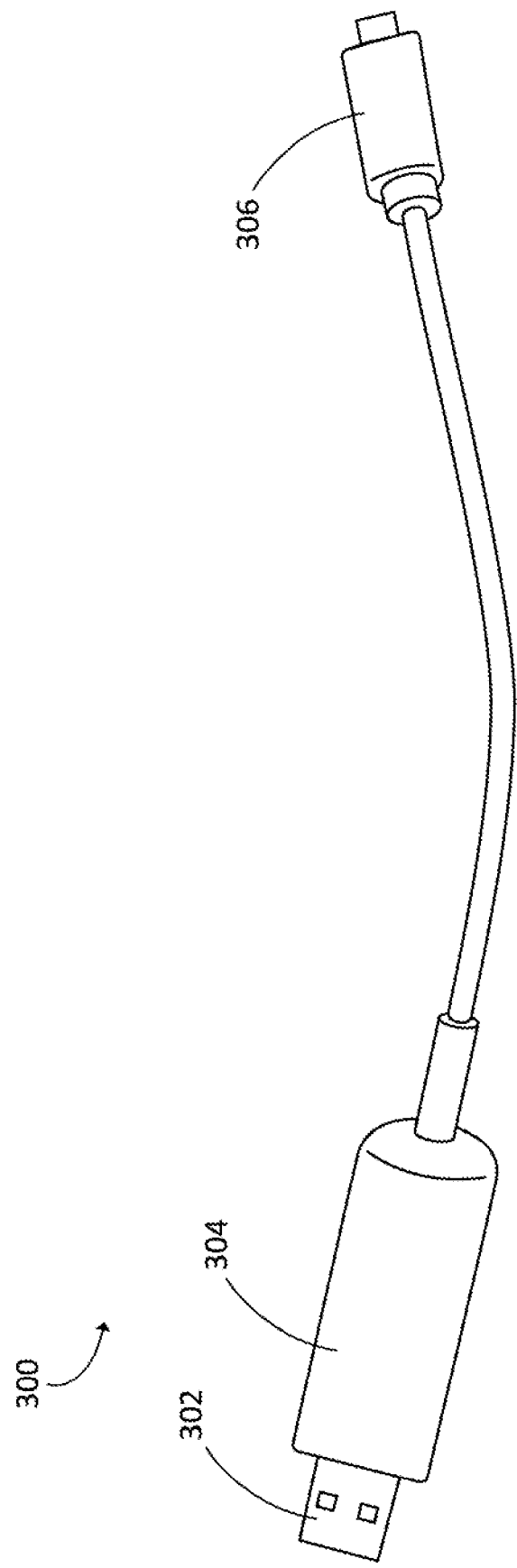
FIG. 14A is a top view of a proprietary cable for the sensor device of FIG. 12 and the sensor device of FIG. 1A, in accordance with an embodiment.
Figure 14B:
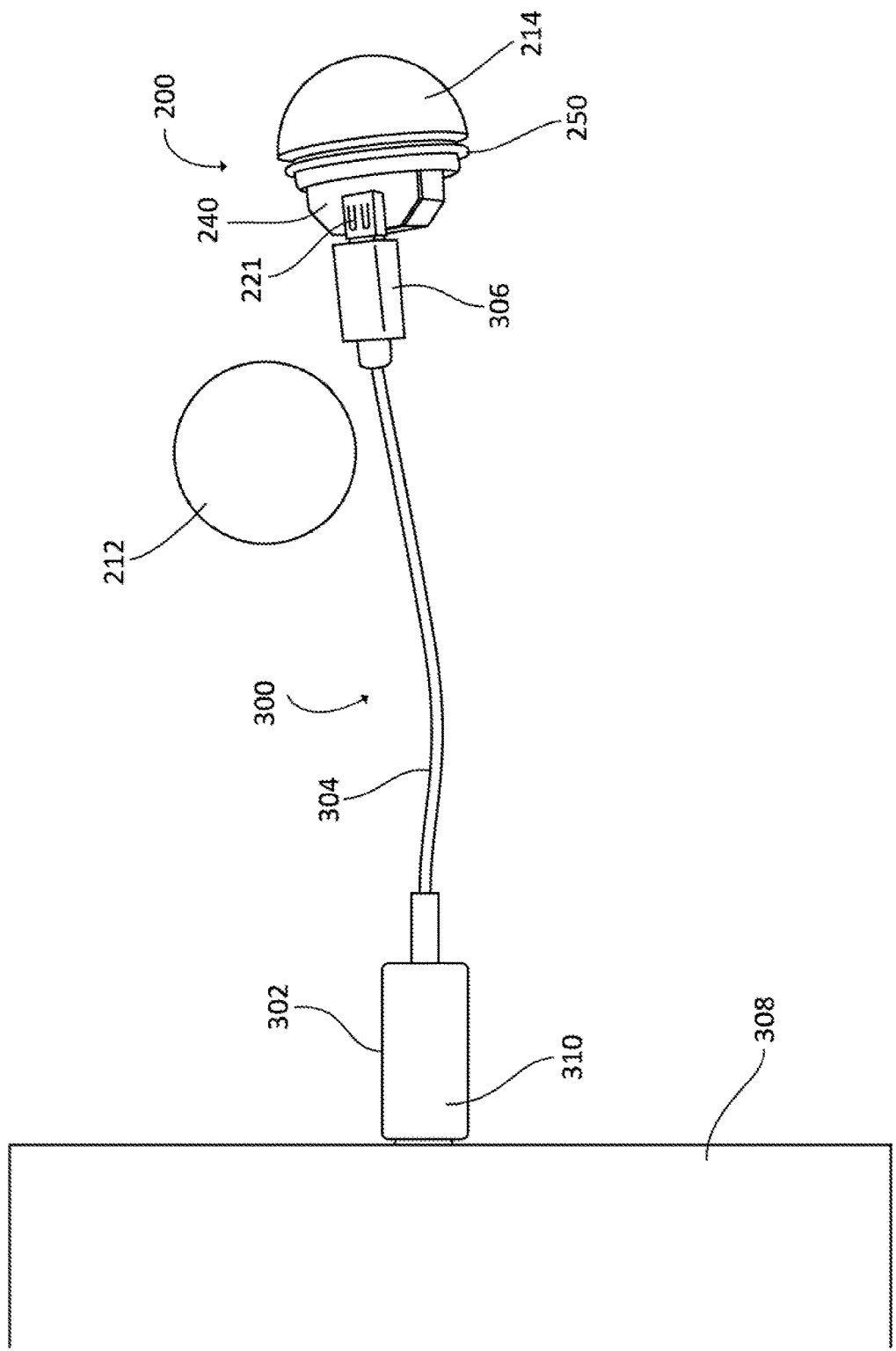
FIG. 14B is a top view of the proprietary cable of FIG. 14A connecting the sensor device of FIG. 12 to an external computer system.
Figure 19:
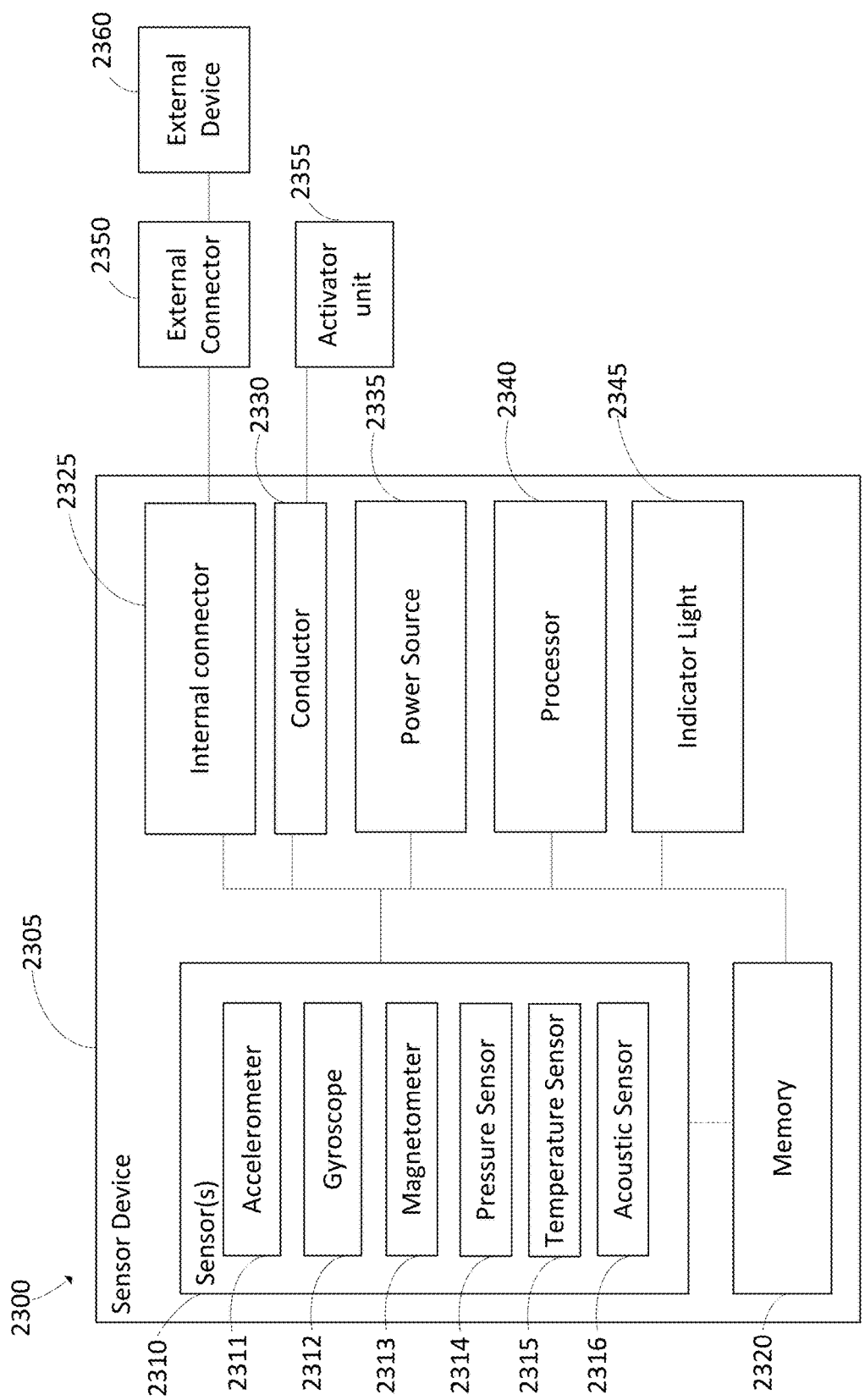
FIG. 19 is a block diagram of a system for collecting fluid data and fluid conduit data, in accordance with another embodiment.

Reference is now made to FIGS. 14A-B illustrating a proprietary cable 300 that can be used, instead of a cradle, with the sensor device 100, 200 to connect the sensor device 100, 200 to an external computer system, such as the computer system 690 of FIG. 6 or computer system 2360 of FIG. 19, for transmitting data to and from the computer system, charging the power source 258 of the sensor device, programming the sensor 180, 280 and the acoustic sensor 244, testing (including factory-testing) the sensor device 100, 200, reading the collected data stored in the memory of the sensor platform 140, 240 and acoustic sensor platform 242, and other functions that cradles described above can perform.

When using the proprietary cable 300, instead of removing the inner frame 120, 220 from the interior compartment 170, 270 of the sensor device 100, 200 and placing the inner frame 120, 220 in the cradles described above, the first capsule portion 112, 212 would be detached from the second capsule portion 114, 214 to expose the USB port 221. The proprietary cable from a capsule head 306 is received by the USB port, 221. The proprietary cable also has a computer system head 302 to be received by a computer system, such as the computer system 690 of FIG. 6 or computer system 2360 of FIG. 19. The capsule head 306 is connected to the computer system head 306 through a connecting cable 304.

In the example illustrated, the proprietary cable also includes a charging circuitry 302. When using the proprietary cable 300, the sensor device 100, 200 may not need to be equipped with a separate charging circuitry. In this embodiment, the proprietary cable also includes an indicator light 310. Accordingly, the sensor device 100, 200 may not need to have a set of indicator lights 650, described above and illustrated in FIG. 6, for showing the charging status. In this embodiment, the sensor device 100, 200 may only have a white indicator light showing on/off status of the sensor as the charging status may be illustrated by indicator light 310 of the proprietary cable 300.

In an embodiment, the proprietary cable does not program the acoustic sensor and platform or set or read data. In this case, the acoustics platform includes a dedicated memory (for example a micro-SD card) which may be removable. The dedicated memory may be connected (for example via a SD card reader) to a computer for read out.

Figure 15A:
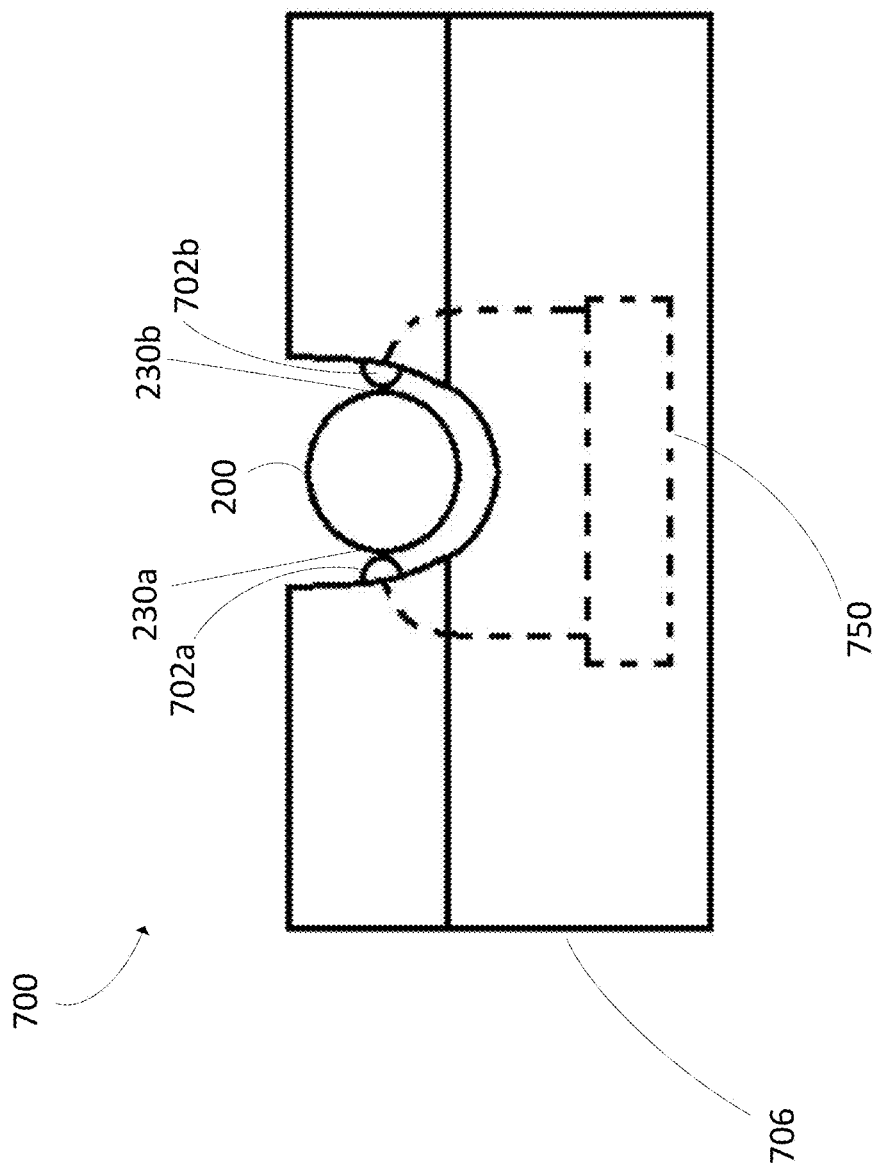
FIG. 15A is a schematic representation of an activator unit for the sensor device of FIG. 12 and the sensor device of FIG. 1A, in accordance with another embodiment.
Figure 15B:
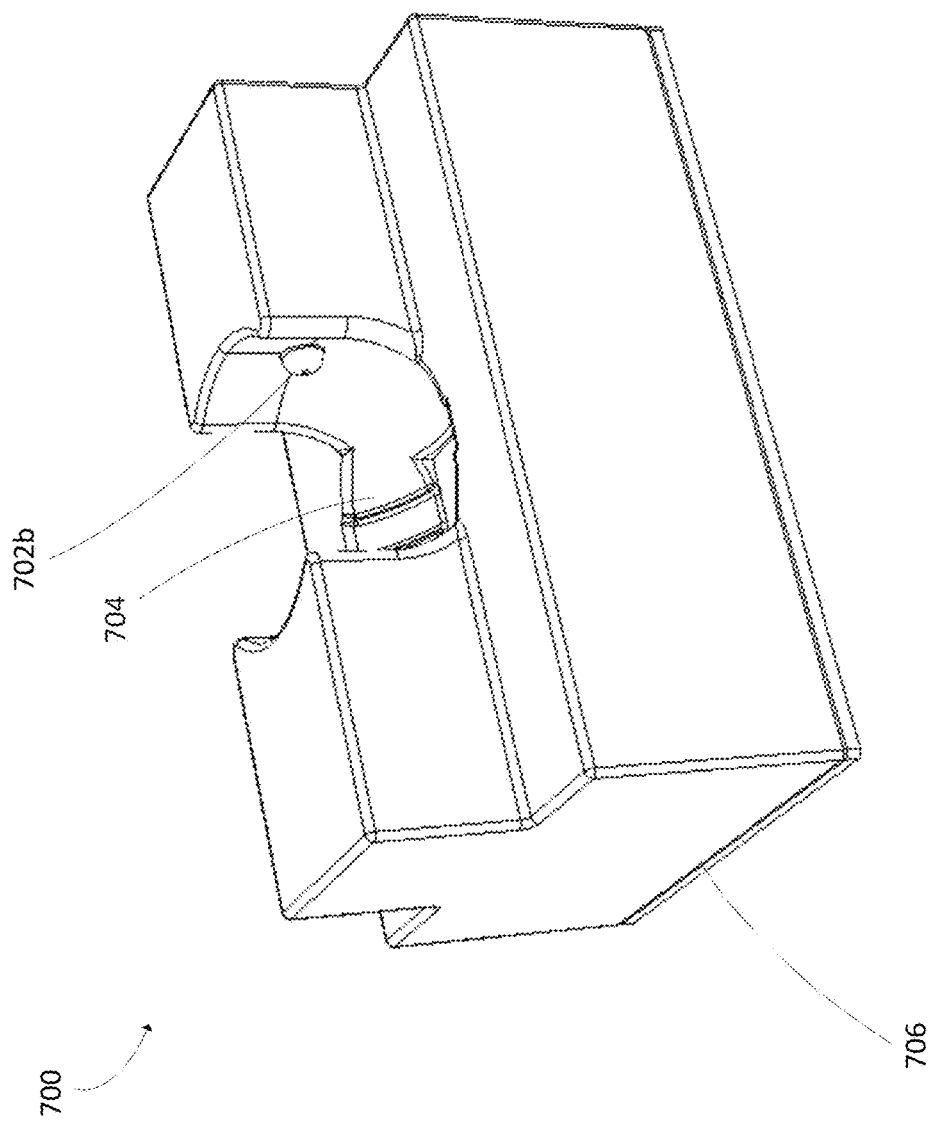
FIG. 15B is a perspective view of the activator unit of FIG. 15A.
Figure 15C:
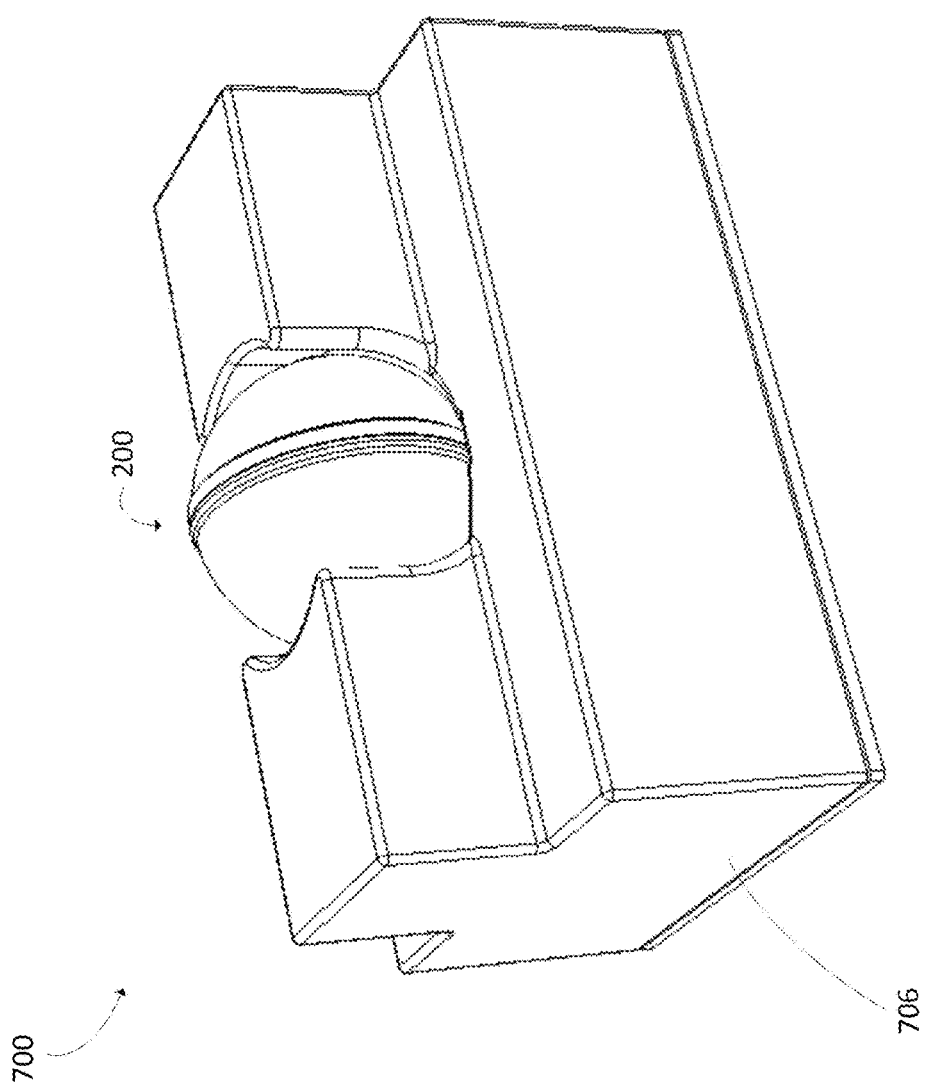
FIG. 15C is a perspective view of the activator unit of FIG. 15A showing the sensor device of FIG. 12 received by the activator unit.

Reference is now made to FIGS. 15A-C illustrating another embodiment of an activator unit 700. Similar to the activator unit 500, the activator unit 700 may be used to apply a signal across the conductors of the sensor device 100, 200 (e.g. 130a, 130b, 230a, 230b). The activator unit 700 includes a base 706 supporting a pair of conducting hemispheres 702a, 702b connected to an activator power source 750. The activator power source 750 may be similar to the activator power source 550. The activator unit 700 includes a cavity 704 for receiving the sensor device 100, 200. In some embodiments, the activator unit 700 may include an on/off switch similar to on/off switch 570 of the activator unit 500.

The conducting hemispheres 702a, 702b may apply a signal across the conductors of the sensor device 100, 200 (e.g. 130a, 130b, 230a, 230b) when connected to those conductors. Various signals may be applied using conducting hemispheres 702a, 702b. For example, a signal may be applied by applying, through the conducting hemispheres 702a, 702b, the activator power source 750 to the conductors of the sensor device 100, 200 (e.g. 130a, 130b, 230a, 230b) for 2 or more seconds. This signal may be interpreted by the sensor device 100, 200 differently than, for example, a signal that is less than 2 seconds long. In some embodiments, a signal provided by the activator unit 700 may be used to activate the sensor device 100, 200.

Reference is now made to FIG. 19, which illustrates a system 2300 for collecting fluid data and fluid conduit data, in accordance with another embodiment. The system 2300 includes an encapsulated sensor device 2305, such as the sensor device 100 described with reference to FIGS. 1A-F, 2A-C, and 3A-D, or the sensor device 200 described with reference to FIGS. 12 and 13A-C, for immersing in a fluid to collect the fluid data and fluid conduit data. The system 2300 also includes an external connector 2350 for communicating with an external device such as a computer system 2360. The external connector 2350 can be a cradle such as the cradle 400, or any other cradles described heretofore, a cable such as the proprietary cable 300, a memory card reader for receiving a memory card installed on the sensor device 2305, or any other means known in the art for transmission of data.

The sensor device 2305 includes a sensor 2310 for taking measurements about a property of the fluid and the fluid conduit. The sensor may 2310 include any one or more of a triaxial accelerometer 2311, a triaxial gyroscope 2312, a triaxial magnetometer 2313, a pressure sensor 2314, a temperature sensor 2315 and an acoustic sensor 2316. In other embodiments, the sensor 2310 may include other sensors, such as an ultrasonic sensor, as well. In other embodiments, the sensor device 2305 can have more than one of each of the accelerometer 2311, gyroscope 2312, magnetometer 2313, pressure sensor 2314, temperature sensor 2315 and acoustic sensor 2316. For example, when the sensor device 2305 have multiple accelerometer 2311 and gyroscope 2312 the measurement errors caused by, e.g., rotation of the sensor device 2305 about its own axis, tipping over or capsizing of the sensor device 2305, etc., can be reduced or cancelled out.

In an embodiment, the acoustic sensor 2316 is not integrated with the main architecture of the sensors 3210 and may be connected directly to a dedicated acoustic processor which amplifies, digitizes, and compresses the data and writes it to a dedicated memory, there being at least two memories in the system. The acoustic processor may be operatively connected to the processor 2340.

The sensor device 2305 includes a memory 2320 for storing measurements taken by the sensor 2310. The memory 2320 may include 1 GB of Serial NOR Flash Memory. In other embodiments, the memory 2320 may include other forms and sizes of computer-readable memory. The memory 2320 may also be removable and/or swappable. For example, the memory 2320 may be an SD or microSD card fitted to an appropriate interface. The memory 2320 may receive data directly from the sensor 2310, or it may communicate with sensor 2310 via a processor 2340. When the memory 2320 is full, it may shut down the sensor device 2305 automatically by signaling the memory status to the processor 2340. The sensor device 2305 may have more than one memory 2320. For example, similar to the sensor device 200, the acoustic sensor 2316 may have a dedicated memory of its own while the rest of the sensors may share another memory.

The sensor device 2305 includes at least one internal connector 2325 (USB port 221 of FIG. 13A) for communicating with the computer system 2360. The internal connector 2325 is electrically connected to the processor 2340. When the sensor device 2305 is interfaced with the external connector 2350, the processor 2340 can be connected to the computer system 2360.

The sensor device 2325 may also include conductors 2330 (e.g. 130a and 130b of the sensor device 100 or 230a and 230b of the sensor device 200). The processor 2340 may accept different instructions through the internal connector 2325 than through the conductors 2330. For example, the processor 2340 may only turn on or off the sensor device 2305 in response to signals received through the conductors 2330 via an activator unit 2355. In other embodiments, all signals from sensor device 2305 to the computer system 2360 may be routed through the conductors 2330. The activator unit 2355 may be similar to the activator units 500, 700 described above.

The sensor device 2305 includes a power source 2335 for providing power to the components of the sensor device 2305. The power source 2335 provides stored power to perform continuous measurements by the sensor 2310. The power source 2335 may be similar to power source 258 of the sensor device 200 or power source 670. All the related discussions above with respect to the power source 670 may be applicable to the power source 2335 as well. The power source 2335 may be chargeable through the set of conductors 2330 with the activator unit 2355 or it may be charged through the internal connector 2325 interfacing with the external connector 2350. The charging circuitry may be within the external connector 2350.

The sensor device 2305 includes the processor 2340 for performing logical operations. The processor 2340 may include more than one processor. For example, similar to the sensor device 200, the acoustic sensor 2316 may have a dedicated processor while the rest of the sensors within the sensor 2310 may share another processor. The processor 2340 may be an ATxmega128A4U-CU processor manufactured by Atmel. The processor 2340 may be reprogrammable (e.g. using instructions from computer system 2360) to change the capabilities and configuration of sensor device 2305, as discussed above in relation to the processor 660.

The sensor device 2305 includes at least one indicator light 2345 for indicating the status of the sensor device 2305. The indicator light 2345 may be similar to the indicator lights 650 of the sensor device 610, described above. Alternatively, the indicator light 2345 may be a single white light-emitting diode for indicating the on/off status of the sensor device 2305.

The computer system 2360 may be a general purpose computer that includes a USB port and other features described above in relation to the computing system 690.

Figure 16A:
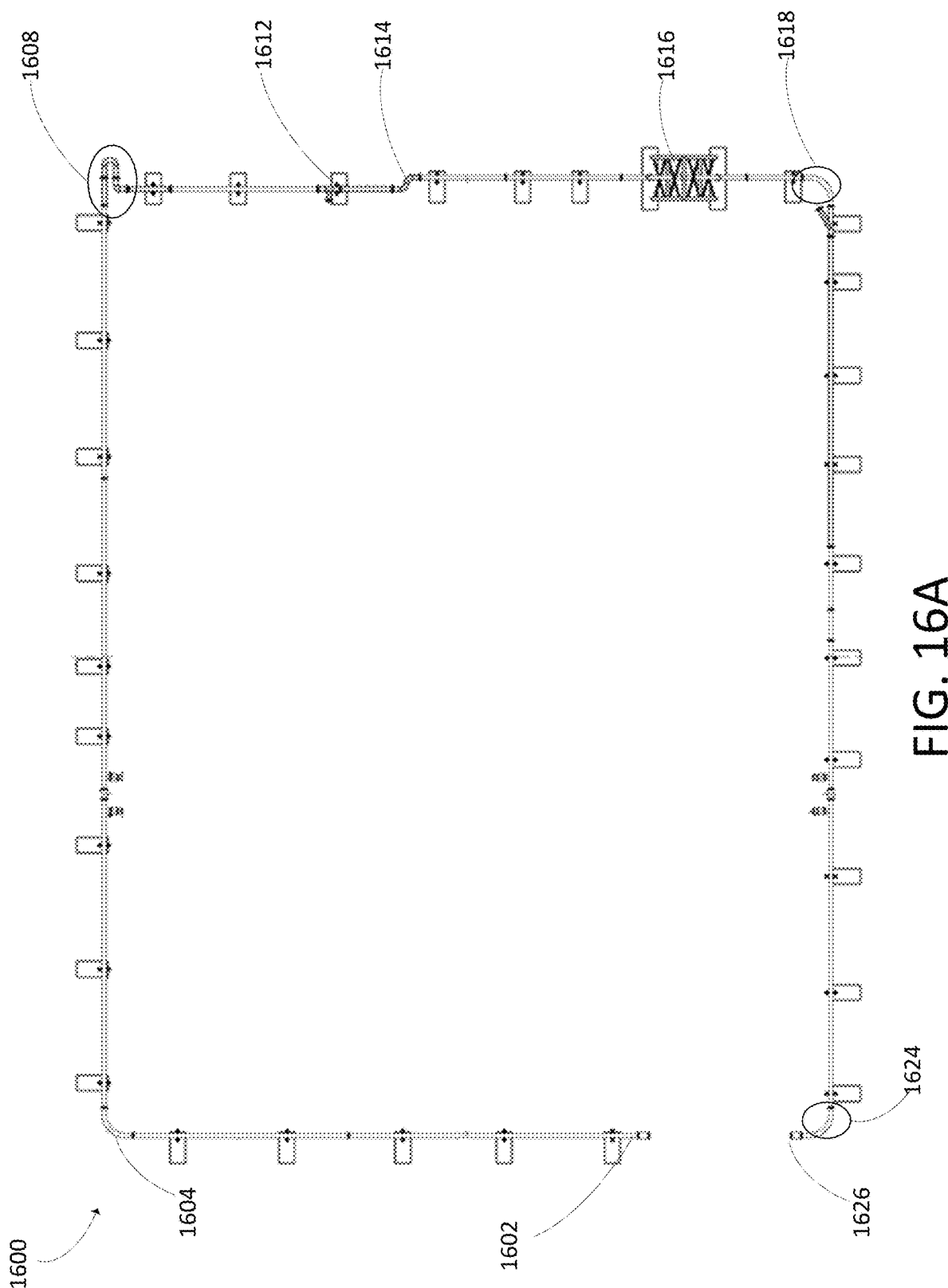
FIG. 16A is a schematic representation of a pipeline loop used in an experiment for collecting data using the sensor device of FIG. 12.
Figure 16B:
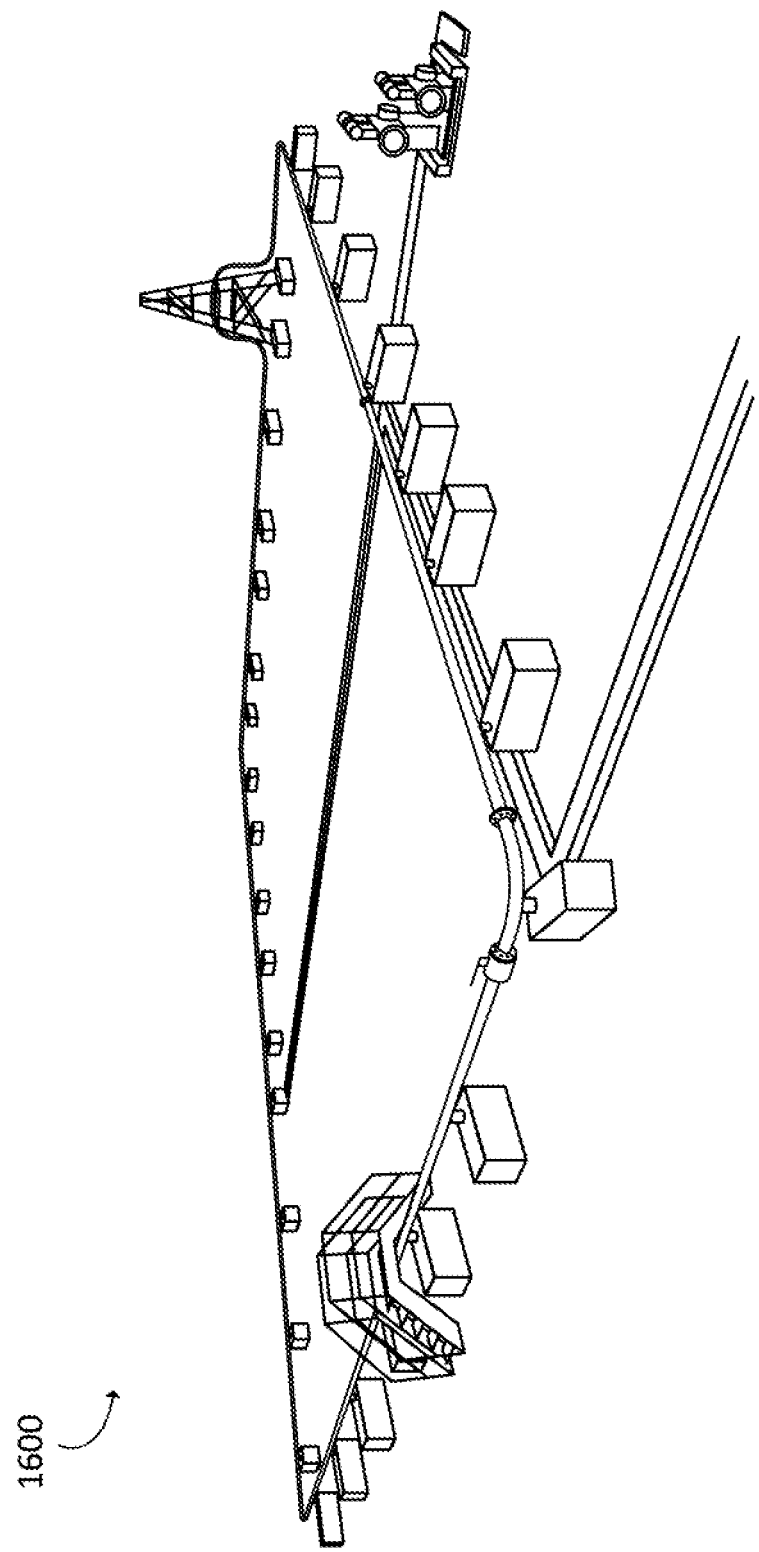
[FIG. 16B is a photograph of the pipeline loop of FIG. 16A, in perspective.

Reference is now made to FIG. 16A demonstrating an experiment conducted to collect data with a sensor device within a pipeline loop and various graphs showing the collected data. Referring now to FIGS. 16A and 16B, a pipeline loop 1600, and its various components and sections, used in an experiment for collecting data using the sensor device of FIG. 12 or FIG. 19 is illustrated. FIG. 16A shows the schematic of the pipeline 1600. FIG. 16B shows a perspective photograph of the pipeline 1600. The pipeline includes a launching pigging valve 1602, a first bend 1604, a second bend 1608, a ball valve region 1612, a jumper section 1616, a third bend 1618, and a fourth bend 1624 and a receiving pigging valve 1626 of the pipeline loop 1600, respectively. Pipes used in the pipeline loop 1600 have generally a dimeter of 6 inches.

The embodiment of the sensor device 200 used in the experiment has a diameter of 1.5 inches, is capable of resisting pressure up to 30 bar, can operate in temperature condition of −4° F. to 140° F., and has a specific gravity of 0.8 to 1.75 of water's specific gravity. The measurement duration is 3 hours. The sensor device 200 can measure a pressure range of 0 to 30 bar with ±3.5 mbar accuracy; measure temperature of −4° F. to 140 F with ±0.027° F. accuracy; and measure a maximum acceleration of ±16 g. The gyroscope of the sensor device 200 can operate between 0 dps to ±2000 dps while the magnetometer can measure magnetic field between 0 Gauss and ±16 Gauss. The acoustic sensor of the sensor device 200 can detect a leak within the fluid conduit with a leak rate of at least 2 gpm.

Referring now to FIG. 16A, the sensor device 200, 2305 can be introduced into the pipeline loop 1600 through the launching pigging valve 1602. Cap 1632 of the launching pigging valve 1602 can be removed. Then, the sensor device can be placed within launching cavity 1636. Afterwards, the cap 1632 would be placed back and lever 1634 can be engaged to align the cavity 1646 and the sensor device 200 with the flow path of fluid within the pipeline loop 1600. Thus, the sensor device 200 is now launched and inserted within the pipeline loop 1600. The launching pigging valve 1602 can operate according to methods known and used in the art.

The sensor device 200 follows the pipeline loop from the launching pigging valve 1602 by passing through the first bend 1604, the second bend 1608, the s-bend 1614, the jumper section 1616, the fourth bend 1618, and the fifth bend 1624 towards the receiving pigging valve 1626. The receiving pigging valve 1626 can be generally similar to the launching pigging valve 1602. In the embodiment illustrated, the receiving pigging valve 1626 includes a removable catch device 1630 in its receiving cavity 1640 to facilitate retrieval of the sensor device 200 from the pipeline loop 1600. The receiving pigging valve 1626 can operate according to methods known and used in the art.

When the sensor device 200 reaches the receiving pigging valve 1626, it either can be extracted from the pipeline loop 1600 so that the collected data can be analyzed or can continue and loop the pipeline loop 1600 again to conduct more runs of the experiment, thereby to collect more data. Regardless, during each loop that the sensor device 200 is within the pipeline loop 1600, the sensor device 200 can collect data using its sensors. In this embodiment, the sensor device 200 can collect acceleration, gyroscopic, magnetic, pressure, temperature and acoustic data using its triaxial accelerometer, triaxial gyroscope, magnetometer, pressure sensor, temperature sensor and piezo transducer based acoustic sensor, respectively.

In this experiment, the sensor device 200 can measure acceleration, rotation, and magnetic fields at a frequency of 400 Hz, pressure and temperature at a frequency of 30 Hz. The sensor device 200 can also record acoustic data with a frequency of 48 KHz. Before analyzing the collected data, the data can be pre-processed by calibrating the sensors of the sensor device 200 and reducing the electronic noise present. After doing so, the data can be analyzed by: analyzing the individual sensors of the sensor device 200, combining the data collected by each sensor per run of the experiment and comparing the results for different runs of the experiment, as discussed above in more detail in relation to method 900.

As discussed above in relation to method 900, and discussed below in more detail, the data collected may show information about the system that the fluid is passing through, such as fluid conduit data, and the fluid itself. For example, the data may show the flow speed, whether there is laminar flow, whether there is turbulent flow, wave patterns, the existence of sedimentation ("waxing"), the existence of air pockets, pipe diameter changes, the existence of flow-interrupting artifacts in a pipeline, the position of bends, the position of flow-ups in a pipeline, the position of flow-downs in a pipeline, blockages in a pipeline, location of flanges, location of pipeline clamps, location of valves and pressure regulators, location of welds, existence of a leak in the fluid conduit, location of the leak, size of the leak, etc.

Many of the observations regarding the data graphs, and spectrum signatures that can be attributed to certain flow properties or conduit properties, discussed in relations to FIGS. 10A-10R and FIG. 11 are present and apply to the graphs in FIGS. 17A to 19C as well. Accordingly, observations discussed before are not discussed in as much details below.

Reference is now made to FIGS. 17A to 17D, depicting examples of data collected by the sensor device 200 during its travel within the pipeline loop 1600 in a run of the experiment, and observations that can be made from this data.

Figure 17A:
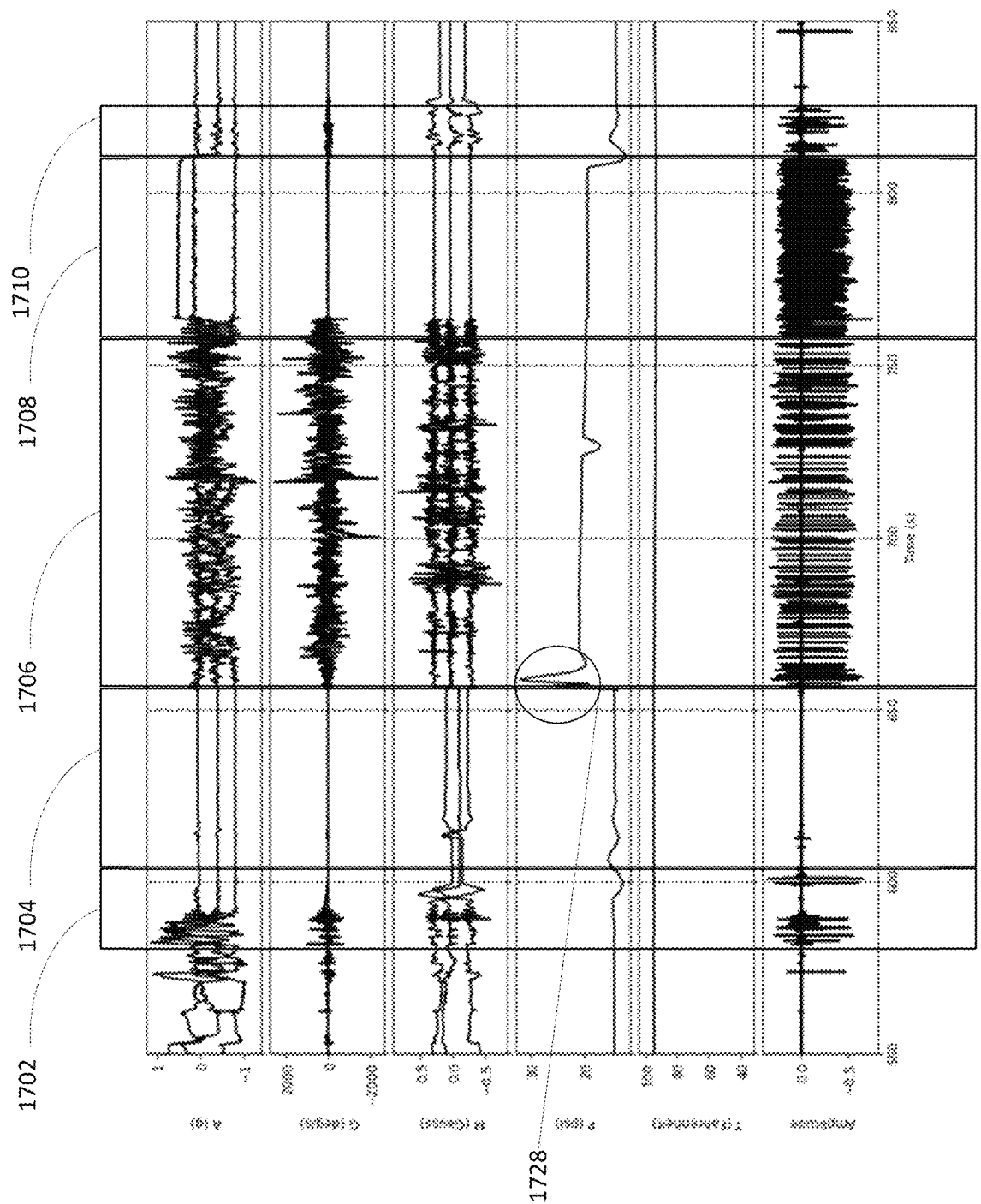
FIG. 17A is a set of graphs of acceleration, gyroscopic, magnetic, pressure, temperature and acoustic data collected by the sensor device of FIG. 12 during its travel within the pipeline loop of FIG. 16A from the launching pigging valve to the receiving pigging valve.

FIG. 17A shows a set of graphs of acceleration, gyroscopic, magnetic, pressure, temperature and acoustic data, top graph to bottom graph, respectively, collected by the sensor device 200 during its travel within the pipeline loop 1600 from the launching pigging valve 1602 to the receiving pigging valve 1626.

Regions 1702 and 1710 can correspond to the insertion of the sensor device 200 into and extraction of the sensor device 200 from the launching pigging valve 1602 and receiving pigging valve 1626, respectively. Spikes in the data and irregular patterns of data can correspond to handling of the sensor device 200 and its placement or extraction from the pigging valves by a human operator. After inserting the sensor device 200 into the launching pigging valve 1602, the sensor device 200 is stationary within the launching pigging valve 1602 for approximately 50 seconds. Region 1704 may correspond to this time period. As can be seen the acceleration and gyroscopic data graphs show a value of almost zero. There is also no significant change in the amplitude of the acoustic data. Region 1706 may correspond to the time that the sensor device 200 is flowing in the pipeline loop 1600. Spikes 1728 in the pressure readout at the beginning of the flow may correspond to the moment the sensor device 200 starts moving with and catching up with the fluid flow. Region 1708 may correspond to the moment the sensor device 200 arrives at the receiving pigging valve 1626 but the fluid is still flowing. As can be seen from the pressure readouts, the moment the flow of the fluid is stopped, the pressure readout dips.

Figure 17B:
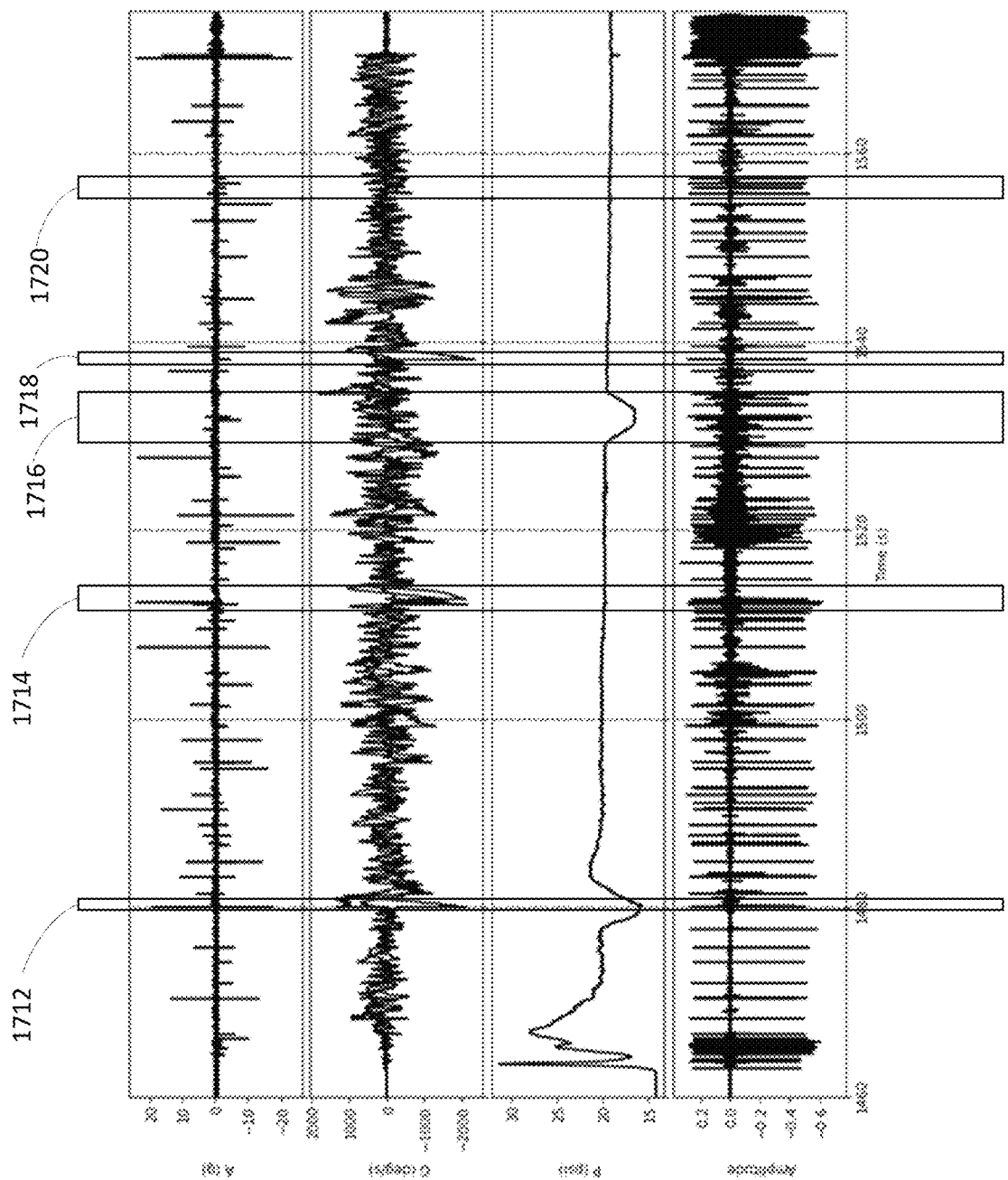
FIG. 17B is a set of graphs of acceleration, gyroscopic, pressure and acoustic data collected by the sensor device of FIG. 12 during its travel through the first bend, the second bend, jumper section and third bend of the pipeline loop of FIG. 16A.

FIG. 17B depicts a set of graphs of acceleration, gyroscopic, pressure and acoustic data, top graph to bottom graph, respectively, collected by the sensor device 200 when passing through the first bend 1604, the second bend 1608, the jumper section 1616 and the third bend 1618 of the pipeline loop 1600. Regions 1712, 1714, and 1718 may correspond to the first bend 1604, the second bend 1608 and the third bend 1618, respectively. Region 1716 may correspond to where the sensor device 200 passes through the jumper section 1616, while region 1720 (for example) may correspond to where the sensor device 200 is bouncing against the pipeline wall in the region 1620.

As can be seen, when the sensor device 200 passes through a bend, spikes in the acceleration and gyroscopic data, that may be due to change in the direction of the flow, collision of the sensor device with the pipeline wall as a result of the change in the direction of motion, rotation of the sensor device as its passes through a bend, transfer of motion to rotation, and/or the flow becoming turbulent as a result of change in the direction, can be observed.

When moving up and then down through the jumper section 1616, the sensor device 200 may record a pressure drop. When the sensor device 200 is bouncing against the wall of the pipeline in the region 1720 (for example), sudden changes in the gyroscope measurements and sudden changes in the amplitude of the acoustic data as a result of the sensor device hitting the pipeline walls, rotating, and/or changing direction can be observed. The bouncing occurs throughout the run and not only in the region 1720.

Figure 17C:
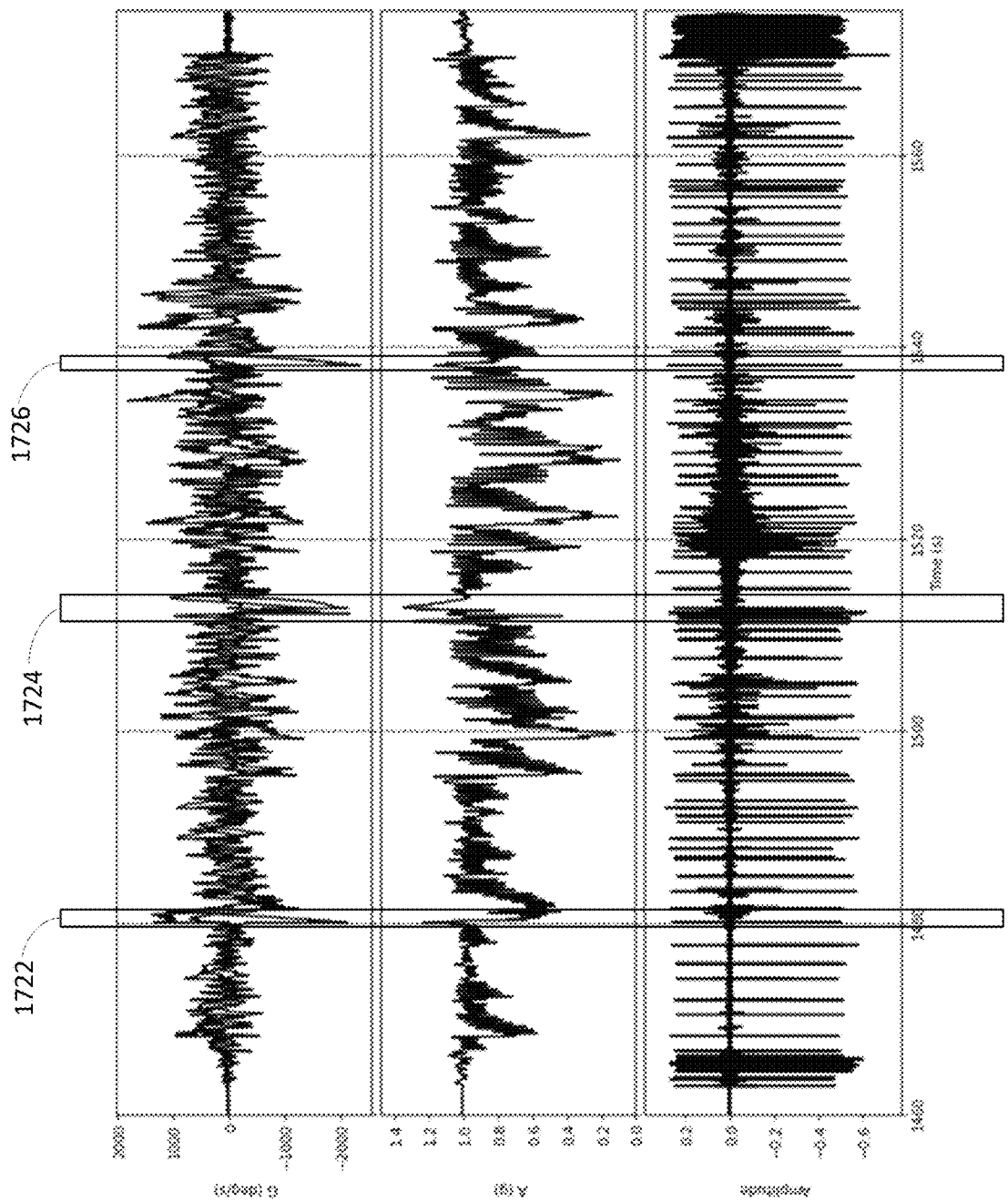
FIG. 17C is a set of graphs of gyroscopic, acceleration and acoustic data collected by the sensor device of FIG. 12 during its travel through the first bend, second bend, jumper section and third bend of the pipeline loop of FIG. 16A.

FIG. 17C depicts a set of graphs of gyroscopic, acceleration and acoustic data, top graph to bottom graph, respectively, collected by the sensor device 200 during its travel through the first bend 1604, the second bend 1608, the jumper section 1616 and the third bend 1618 of the pipeline loop 1600. FIG. 17C is similar to FIG. 17B with the following exception: FIG. 17C does not show the pressure data. FIG. 17C is a slightly zoomed in version of the gyroscopic, acceleration and acoustic data of FIG. 17B to show them in more details. Regions 1722, 1724 and 1726 may correspond to where the sensor device passes the first bend 1604, the second bend 1608, and the third bend 1618, of the pipeline loop 1600, i.e. the same as regions 1712, 1714, and 1718 of FIG. 17B, respectively.

As discussed above, in these regions, 1722, 1724, 1726, the gyroscope may show the rotation of the sensor device 200 when the sensor device 200 passes through the bends. Reference is made to the fluctuations of the gyroscope readouts in these regions between spikes and dips, i.e., a repeating pattern of a readout having a positive value followed by a readout having a negative value. Changes and fluctuations in the acceleration readouts may correspond to the shift that the sensor device 200 may experience in its kinetic behaviors: from generally a rectilinear motion in a straight section of the pipeline loop 1600 to a rotation along one of its own axes as a result of passing through the bends.

Figure 17D:
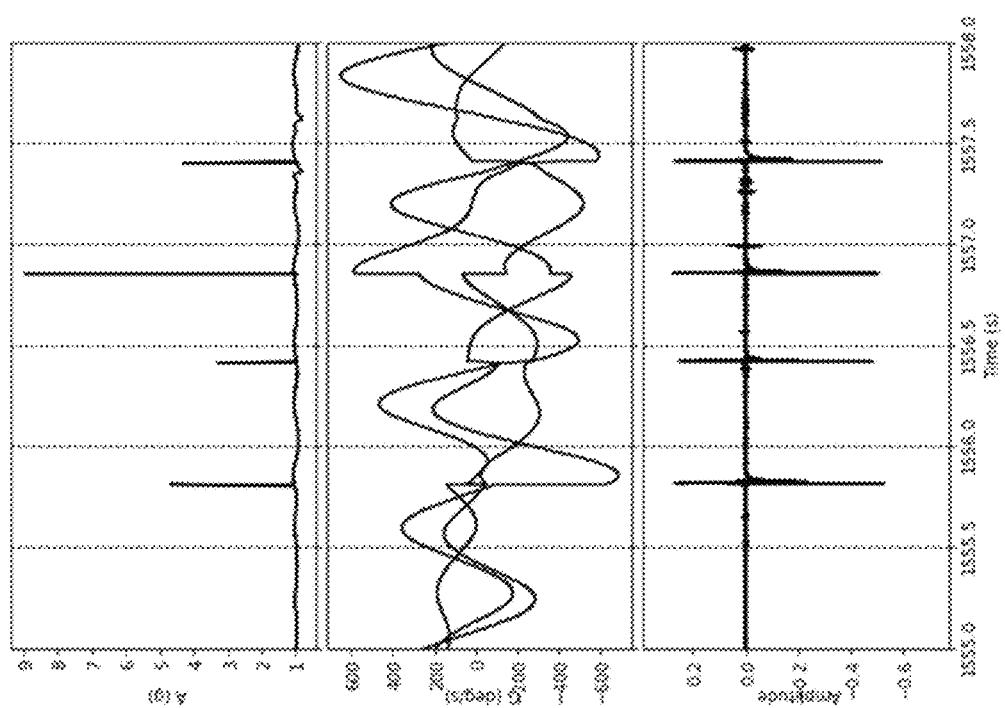
FIG. 17D is a set of graphs of acceleration, gyroscopic and acoustic data collected by the sensor device of FIG. 12 showing effects of the sensor device bouncing against walls of the pipeline loop of FIG. 16A on the collected data.

FIG. 17D is a set of graphs of acceleration, gyroscopic and acoustic data, top graph to bottom graph, respectively, collected by the sensor device 200 showing effects of the sensor device 200 bouncing against the walls of the pipeline loop 1600 on the collected data. As can be seen, bounces may cause a sharp spike in the accelerometer and acoustic data, and an abrupt change in the gyroscopic data.

Reference is now made to FIGS. 18A to 18D, depicting examples of data collected by the sensor device 200 during its travel within the pipeline loop 1600 in another run of the experiment for demonstrating the leak detection capabilities of the sensor device 200. A leak can be simulated in the pipeline loop 1600 by partly opening the ball valve 1628 positioned at region 1612 of the pipeline loop 1600. The leak size is determined by the time it took to fill a 5 gallon bucket. Leak size between 0.2 and 22 gpm are tested.

What follows is a summary of how each leak detection run of the test can be conducted: 1) the sensor device 200 is positioned in the launching pigging valve 1602 and the launching pigging valve 1602 is brought into fluid communication with the rest of the pipeline loop 1600 by actuating lever 1634; 2) the flow is started within the pipeline loop 1600 and the leak is created simultaneously by at least partially opening the ball valve 1628 to create a leak; 3) the sensor device 200 starts its run and data collection within the pipeline loop 1600; 4) the actual leak size is determined during the run; 5) the sensor device is caught in the receiving pigging valve 1626, as discussed above; and 6) the flow is stopped.

Figure 18A:
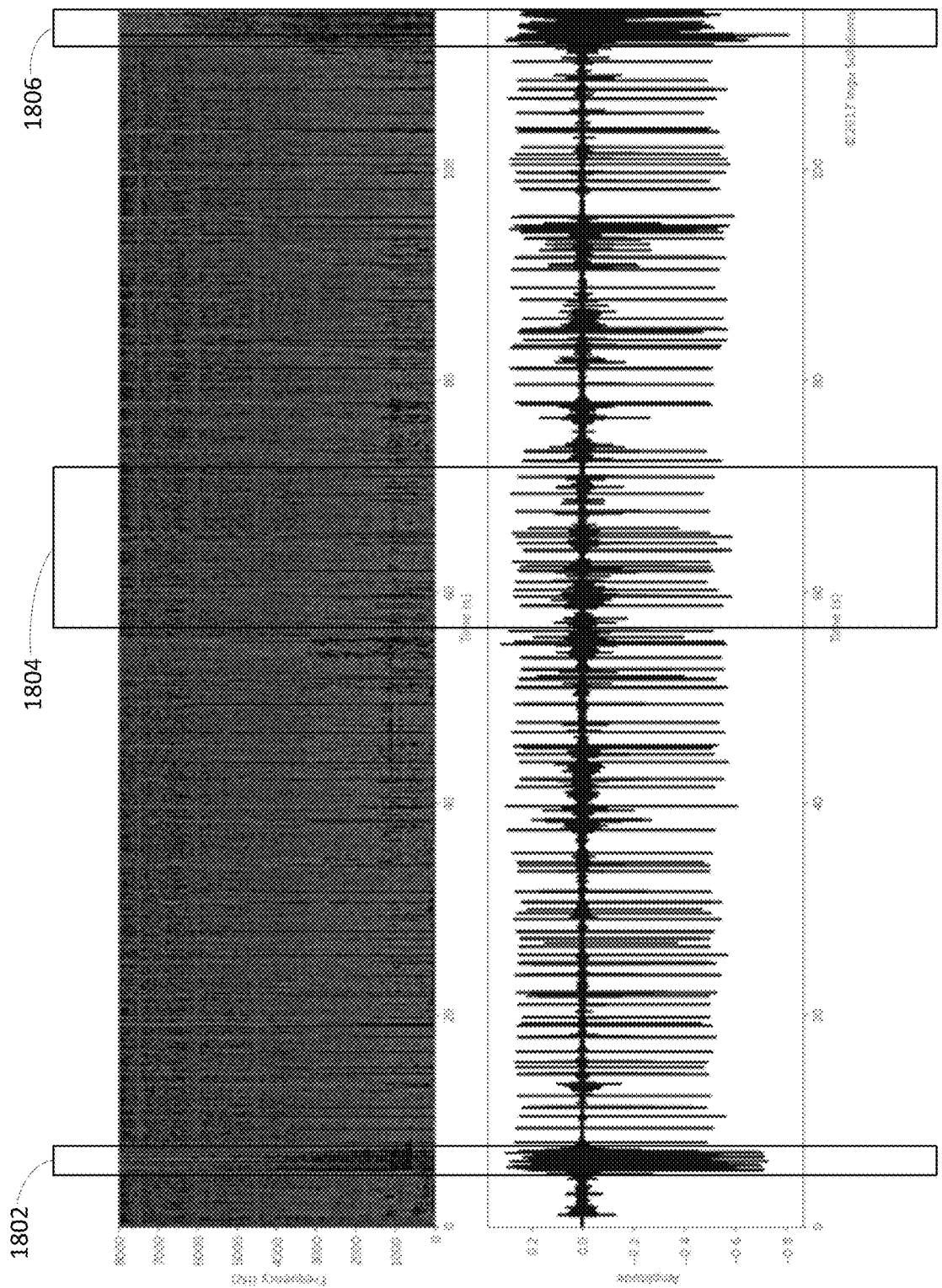
FIG. 18A is a set of graphs of acoustic data, showing frequency spectrum and amplitude spectrum, collected by the sensor device of FIG. 12 while passing through the ball valve of FIG. 16G when the ball valve is closed.

Referring now to FIG. 18A, a set of graphs of acoustic data, showing frequency spectrum and amplitude spectrum, top and bottom graphs, respectively, collected by the sensor device 200 while passing through the ball valve region 1612 of the pipeline loop 1600 when ball valve 1628 is closed, are shown. Both the frequency spectrum and amplitude spectrum are depicted as functions of time. It should be noted that the intense spikes at the beginning of both the frequency and amplitude spectra, region 1802, may be caused by a number of hits, e.g. three, on the pipeline loop 1600 by a human operator for the purpose of verifying the start of the test run. As can be seen, these hits are recorded by the acoustic sensor 244 of the sensor device 200. Region 1804 may correspond to where the ball valve 1628 is, i.e., where the leak can be created. In this run of the experiment, the ball valve 1628 is closed and thereby no leak was created. As can be seen, amplitude and frequency patterns within the region 1804 are not significantly different than amplitude and frequency patterns immediately before and after this region. Region 1806 may correspond to the sensor device 200 bouncing against the receiving pigging valve 1626 at the end of the experiment run. As a result of the sensor device 200 colliding with the receiving pigging valve 1626, intense spikes in both the frequency and amplitude spectra may be observed.

Figure 18B:
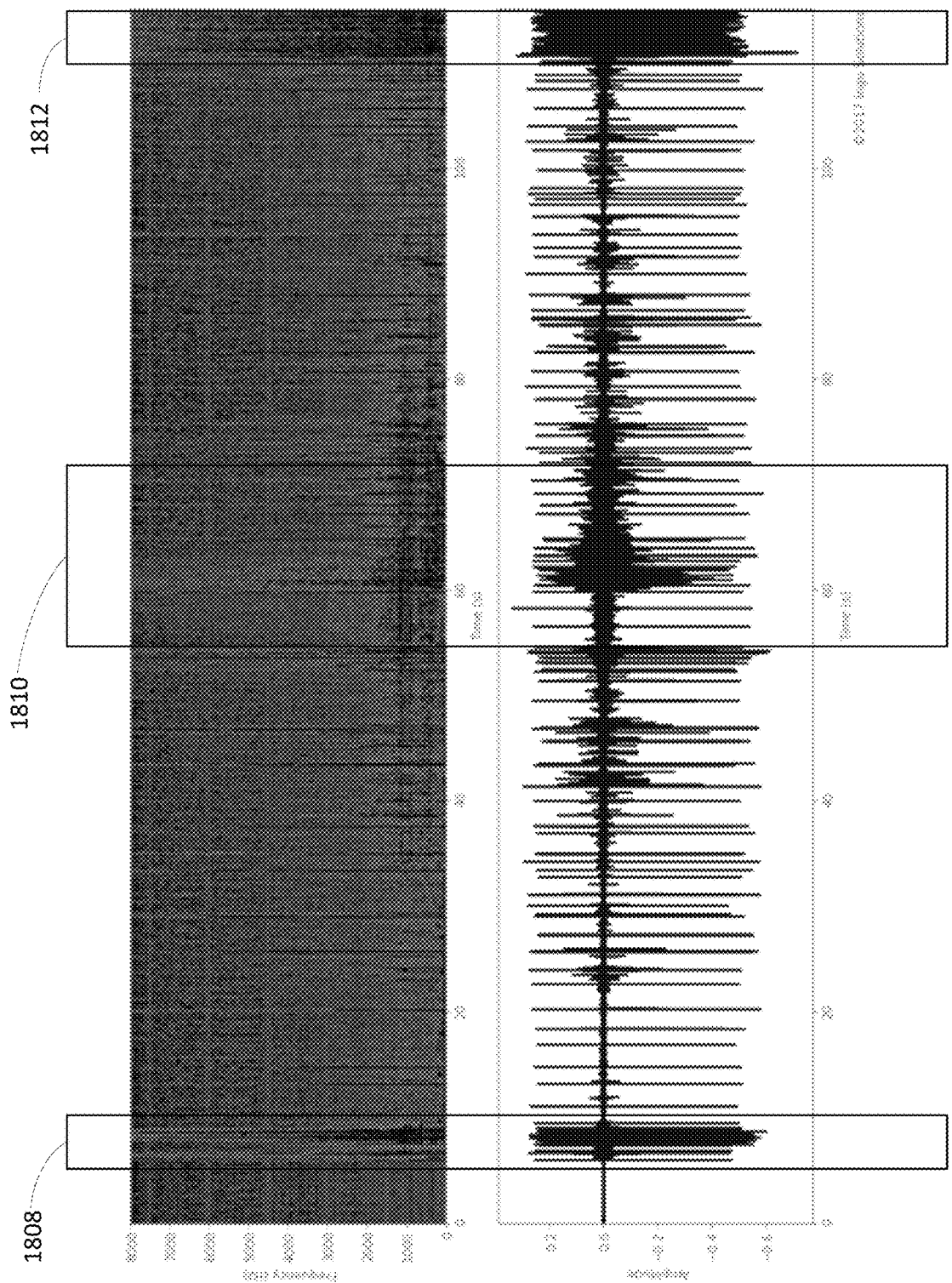
FIG. 18B is a set of graphs of acoustic data, showing frequency spectrum and amplitude spectrum, collected by the sensor device of FIG. 12 while passing through the ball valve of FIG. 16G when the ball valve is partly open to simulate a leak condition at a rate of 10.7 gpm within the pipeline loop.

FIG. 18B is a set of graphs of acoustic data, showing frequency spectrum and amplitude spectrum, collected by the sensor device 200, while passing through the ball valve 1628 when the ball valve 1628 is at least partially open to simulate a leak condition at a rate of 10.7 gpm within the pipeline loop 1600. Similar to FIG. 18A, the intense spikes at region 1808 may correspond to a number of hits on the pipeline loop 1600 by the operator to verify start of the run while the intense spikes at region 1812 may correspond to the sensor device 200 bouncing against the walls of the receiving pigging valve 1626. Region 1810 may correspond to where the ball valve 1628 is and a leak of 10.7 gpm in the pipeline loop 1600 is being created. Comparing region 1810 to region 1804, intense spikes, and changes in the frequency and amplitude patterns, can be observed. This may be a signature that a leak is present in the pipeline loop 1600. In other words, the leak may cause an unambiguous audio signal, having frequency and amplitude characteristics such as those observed in region 1810, which may also be detected by the human operator's ears upon listening to the audio data.

Figure 18C:
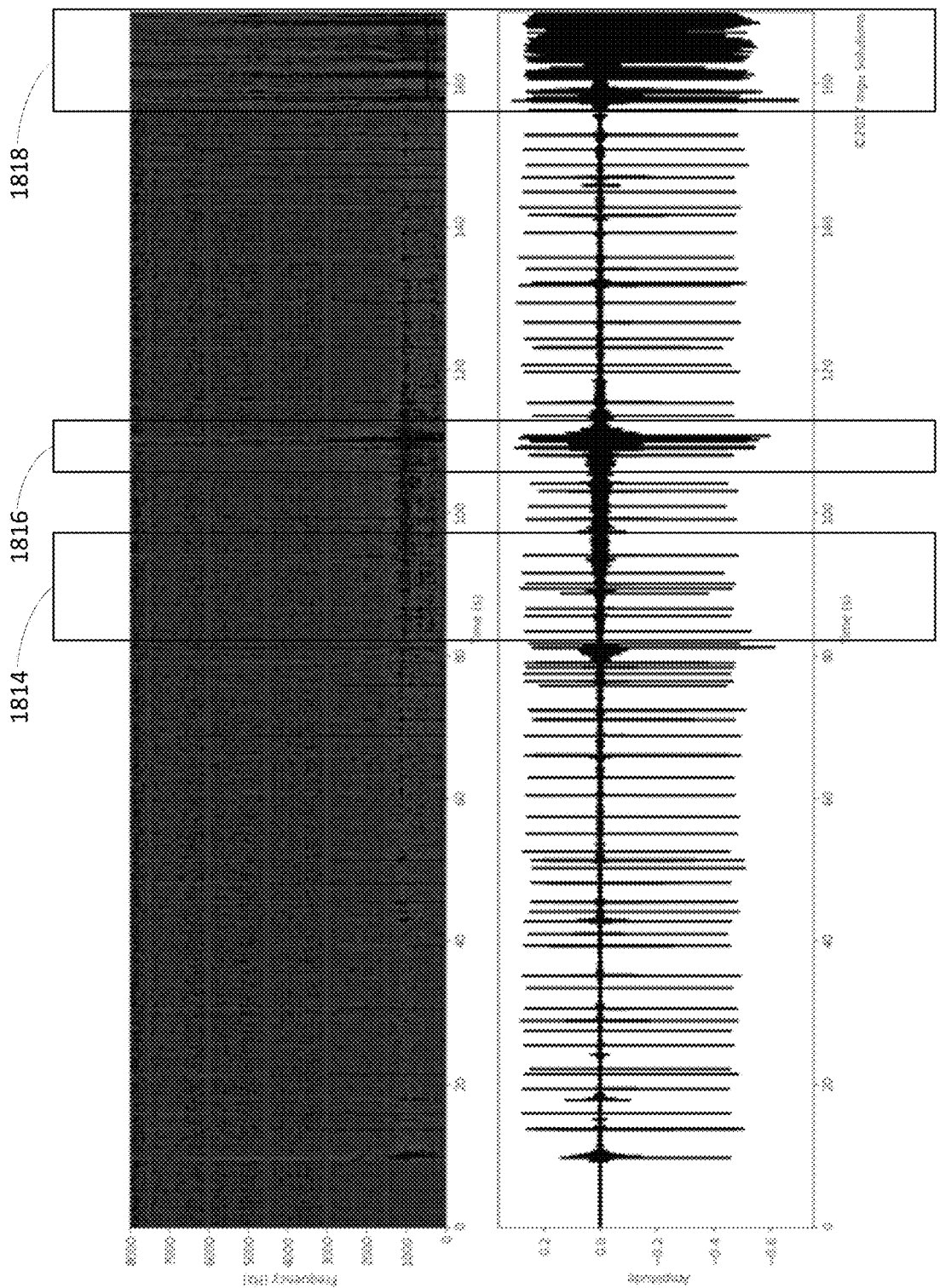
FIG. 18C is a set of graphs of acoustic data, showing frequency spectrum and amplitude spectrum, collected by the sensor device of FIG. 12 while passing through the ball valve of FIG. 16G and the jumper section of FIG. 16I, when the ball valve is closed.

Referring now to FIG. 18C, a set of graphs of acoustic data, showing frequency spectrum and amplitude spectrum, top and bottom graphs, respectively, collected by the sensor device 200 while passing through the ball valve region 1612 of the pipeline loop 1600, when ball valve 1628 is closed, and the jumper section 1616 are shown. Region 1814 may correspond to where the leak can be created, i.e., where the ball valve 1826 is while region 1816 may correspond to where the jumper section 1616 is. Similar to FIG. 18A, as there is no leak in the system, the amplitude and frequency within region 1814 and regions before and after region 1814 are not significantly different. The intense spikes in region 1816 may be the results of air pockets existing in the jumper section 1616, that might have been absent in the experiment runs depicted in FIGS. 18A and 18B. The intense spikes in region 1818 may correspond to the sensor device 200 continuously bouncing against the receiving pigging valve 1626.

Figure 18D:
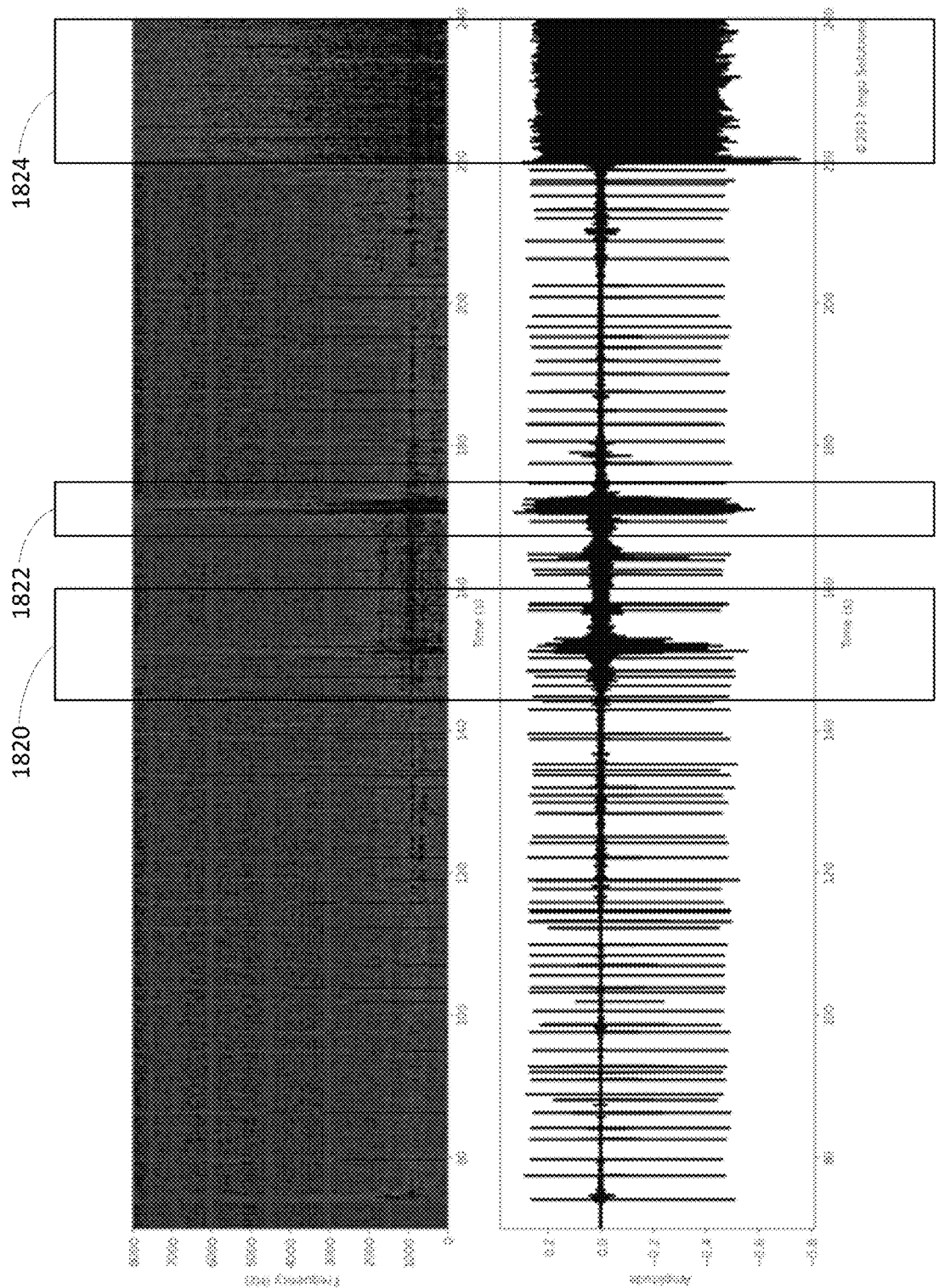
FIG. 18D is a set of graphs of acoustic data, showing frequency spectrum and amplitude spectrum, collected by the sensor device of FIG. 12 while passing through the ball valve of FIG. 16G and the jumper section of FIG. 16I, when the ball valve is partly open to simulate a leak condition at a rate of 2 gpm within the pipeline loop.

FIG. 18D is a set of graphs of acoustic data, showing frequency spectrum and amplitude spectrum, collected by the sensor device 200, while passing through the ball valve 1628 when the ball valve 1628 is at least partially open to simulate a leak condition at a rate of 2 gpm within the pipeline loop 1600. Similar to FIG. 18C, the intense spikes at region 1822 may correspond to presence of air pockets with the jumper section 1616 that might have been absent in the experiment runs depicted in FIGS. 18A and 18B. Region 1824 may similarly correspond to the sensor device 200 continuously bouncing against the receiving pigging valve 1626. Region 1820 may correspond to where the ball valve 1628 is and a leak of 2 gpm in the pipeline loop 1600 is being created. Comparing region 1820 to region 1814, intense spikes, and changes in the frequency and amplitude patterns, can be observed. This may be a signature that a leak is present in the pipeline loop 1600. In other words, the leak may cause an unambiguous audio signal, having frequency and amplitude characteristics such as those observed in region 1820, which may also be detected by the human operator's ears upon listening to the audio data.

Although the leak diameter in the experiment run depicted in FIG. 18D is significantly smaller than in the experiment run depicted in FIG. 18B, the leak still seems to be clearly visible in the spectrum. Smaller size of the leak may be observed from the intense spikes in the region 1820 being less dense than the intense spikes in the region 1810. Also, the intense spikes in the region 1820 fading out faster than those in the region 1810. Moreover, it can be observed from the amplitude that amplitude of the sound corresponding to the smaller size leak may be less than that of the bigger size leak. The leak signal, or audio signatures corresponding to a region with a leak, appears to be distinct. It can be identified in the audio spectrum even without knowing the physical location of the leak along the pipeline through, e.g., the human operator listening to the audio recordings, or automatically through a computing system by analyzing the frequency and amplitude spectra based on the above observations.

The experiment runs described above may demonstrate that the sensor device 200, in one embodiment, may be capable of leak detection up to a minimum leak size of 2 gpm. Alternatively, in other embodiments, the sensor device may be capable of leak detection up to a minimum value that is more or less than 0.2 gpm.

Reference is now made to FIGS. 19A to 19C, depicting examples of pressure data collected by the sensor device 200 during its travel within the pipeline loop 1600 in another run of the experiment. These examples may show observations that can be made based on pressure readouts.

Referring again to FIGS. 9 and 23, in order to determine a leak using the sensor device system 2300 in a pipeline loop such as the pipeline loop 1600, in accordance with the method 900, some aspects of the method 900 may be modified. If no modifications or additions to an aspect of the method 900 is needed, that aspect is not discussed below to avoid repetition.

As discussed above, for placing each activated sensor device 2300 at 920 into the fluid, the sensor device 2300 may be placed in a launching pigging valve, e.g., launching pigging valve 1602, if the fluid is in a pipeline. To do so, a cap of the launching pigging valve, e.g., cap 1632, may be removed. The sensor device 2300 may then be placed in a cavity underneath the cap, e.g., launching cavity 1636. Then, the cap may be fastened back to the launching pigging valve. The sensor device 2300 may now be placed within the flow path by actuating a lever of the launching pigging valve, e.g., the lever 1634. The foregoing was just a non-limiting example of how a launching pigging valve in one embodiment may operate. Other pigging valves and other methods of operating a pigging valve as known in the art can be used at 920 for placing the sensor device 2300 in the pipeline.

At 930, each activated sensor of the sensor device 2300, including the acoustic sensor 2316, may collect data from fluid. The acoustic processor may be configured to collect data at regular time intervals. For example, in the runs of experiment depicted in FIGS. 16A-19B, the acoustic processor collects data at a rate of 48 kHz. In embodiments that the acoustic sensor 2316 of the sensor device 2300 uses a piezo transducer, e.g., the piezo transducer 282 of the sensor device 200, acoustic data can be collected by the acoustic sensor 2316 through converting vibrations of the outer shell of the sensor device 2300 to electrical signals, as known in the art. The electrical signals can then be conditioned, digitized and optionally compressed by the audio processor for conversion into raw audio files and storing these audio files in the audio memory as a first acoustic dataset. The calibration and pre-processing can be performed by a computer system receiving the data, as discussed below at 960. For example, the computer system may be used to calibrate the sensors and data and remove or reduce electronic noise through methods known in the art.

At 940, the sensor device 2300 is extracted from the fluid through, e.g., a receiving pigging valve such as the receiving pigging valve 1626. As discussed above, the receiving pigging valve may be modified by adding a removable catch device, such as the catch device 1630, within a receiving cavity of the receiving pigging valve, e.g., receiving cavity 1640, to facilitate retrieval of the sensor device 2300 from the pipeline.

At 950, one of the first capsule portion or the second capsule portion of the outer capsule of the sensor device 2300 is opened to get access to, e.g., the memory card within the memory card slot 266 or USB port 221.

At 960, the sensor device 2300 is connected to a computer system, such as the computer system 2360 through an external connector 2350, which as discussed before can be, e.g., a cable such as the proprietary cable 300, a memory card reader of the computer device 2360 etc.

At 970, the computer system receives the stored acoustic data, e.g., raw audio data, from the sensor device 2300. The data may be received as compressed audio files.

At 980, the received data can be processed for determining presence of a leak within the pipeline. Presence of a leak can be determined according to the following procedure. 1) The recorded audio spectrum in the frequency domain can be dissected into various regions called categorized and uncategorized, categorized regions including audio signatures that may correspond to easily recognizable events that may take place during the data collection run, e.g., placing the sensor device 2300 into the launching pigging valve, hitting in the launching pigging valve to specify start of the data collection run, receiving the sensor device 2300 from the receiving pigging valve, the sensor device 2300 passing through a bend, a jumper section, etc., the sensor device 2300 bouncing against the walls of the pipeline, etc. 2) The audio signatures within the uncategorized regions, if any, can be compared with the audio signatures within the neighboring categorized regions by identifying intense spikes, changes in the density of intense spikes, irregular patterns, etc. 3) If in 2) no difference between the audio signatures of the uncategorized regions and the audio signatures of the neighboring categorized regions is detected, then there may be no leak present in the pipeline. Otherwise a leak may be present. A human operator may also listen to the audio recording to determine whether the difference between the audio signatures may correspond to presence of a leak.

The free-flowing nature of the sensor device may be particularly advantageous. In particular, the sensor device may freely flow with the fluid and thus limits the created background noise (e.g. no scraping over the pipeline wall). Further, any created background noise can be removed during processing.

Advantageously, the system may combine the data of the different sensors to create signatures to identify pipeline features and determine positioning of the sensor device. For example, changes or anomalies in the data set are identified by comparing different runs and/or looking at deviations from the background in the same run. These anomalies are identified based and stored in a sensor database. The sensor database will become increasingly better with every additional dataset which may be analyzed with machine learning technology. The system will learn to automatically distinguish between categorized and uncategorized regions. As more data is collected, more uncategorized regions become categorized regions and the system learns.

In addition or as an alternative to 2) and 3), above, instead of collecting one run of data, multiple runs of data can be collected from the pipeline by not extracting the sensor device 2300 after flowing within the pipeline for just one run. Data collected from multiple runs of the sensor device 2300 within the pipeline can be compared in determining the presence of a leak. To do so, each set of data is dissected into categorized and uncategorized regions, as discussed above. Uncategorized regions of different runs may be compared together. If any difference exists between the uncategorized regions of different runs, the difference may correspond to presence of a leak in the run having a different uncategorized region. The leak for example might have been absent in prior runs and might have appeared during the run having a different uncategorized region. As said before, the human operator may verify the findings by listening to multiple recordings and performing a comparison.

Where the pipeline is not continuous, the sensor device may not be extracted for an additional run. Either the same or another sensor device may be launched in the pipeline to collect another set of data from the same pipeline. The sensitivity and accuracy may continuously increase per additional data set.

Collecting additional datasets over time, e.g. each month, also provides additional information. The system compares the new dataset to the previous dataset and identifies changes with respect to the previous datasets, e.g. whether a leak was created.

For comparing these datasets of the same pipeline, the system may not need to dissect the data in categorized and uncategorized regions, but will compare the acoustic data of the whole pipeline for different runs to look for changes.

Procedures discussed above can be performed manually by the human operator, can be performed automatically by computer software running on the computer system, or by using both the software and the human operator.

While the above description provides examples of one or more apparatus, methods, or systems, it will be appreciated that other apparatus, methods, or systems may be within the scope of the claims as interpreted by one of skill in the art.

The invention claimed is:

1. A system for predicting presence of a leak in a fluid conduit, the system comprising:
a sensor device for freely flowing with a first fluid within the fluid conduit to sense acoustic properties of the first fluid, the sensor device having an adjustable specific gravity such that the specific gravity of the sensor device is adjustable to a first specific gravity for neutral buoyancy in the first fluid and to at least one other specific gravity for neutral buoyancy in a second fluid having a specific gravity different from a specific gravity of the first fluid, wherein the first specific gravity of the sensor device is constant as the sensor device freely flows with the first fluid, the sensor device having at least one acoustic sensor for sensing the acoustic properties of the first fluid, the sensor device having a memory for storing the sensed acoustic properties as a first audio recording, and wherein the sensor device is transported with the flow of fluid directly and not required to ride on a surface of the fluid conduit; and an external electrical connector for connecting to the memory, the external electrical connector for providing the first audio recording to a computer system;

wherein the computer system is configured to identify a potential leak location in the fluid conduit by:

dissecting the first audio recording into categorized and uncategorized regions, wherein a categorized region includes an audio signature that corresponds to a recognizable event during a data collection run;

comparing a first audio spectrum of the uncategorized regions of the first audio recording with a second audio spectrum of uncategorized regions of a second audio recording , the second audio recording collected from the fluid conduit during a different data collection run, wherein each of the first and second audio spectrums include a plurality of frequency or amplitude values associated with time values indicating when the respective frequency or amplitude values were recorded relative to one another;

detecting an unambiguous audio signal in the second audio recording that is not present in the first audio recording by detecting any one or more of (i) changes in presence of intense spikes between corresponding uncategorized regions in the first and second audio spectrums, (ii) changes in frequency patterns between corresponding uncategorized regions in a first frequency spectrum of the first audio spectrum and a second frequency spectrum of the second audio spectrum, and (iii) changes in amplitude patterns between corresponding uncategorized regions in a first amplitude spectrum of the first audio spectrum and a second amplitude spectrum of the second audio spectrum; and identifying a location in the fluid conduit at which the unambiguous audio signal was recorded as the potential leak location using time data associated with the second audio recording.

2. The system of claim 1, wherein the acoustic sensor of the sensor device comprises a piezo transducer for converting vibrations imposed on the piezo transducer by the first fluid to electrical signals representing the sensed acoustic properties of the first fluid.

3. The system of claim 1 wherein the comparison of the uncategorized audio signature of the uncategorized regions to the recognizable audio signature of the neighbouring categorized region comprises determining any one or more of presence of the intense spikes, density of the intense spikes and presence of the frequency patterns.

4. The system of claim 1, further comprising the fluid conduit, wherein the fluid conduit comprises a plurality of different sections, the acoustic properties of the first fluid within the plurality of different sections substantially corresponding to a plurality of recognizable section-specific audio signatures, the acoustic properties of the first fluid within each section of the plurality of different sections substantially corresponding to at least one recognizable section-specific audio signature of the plurality of recognizable section-specific audio signatures, the at least one recognizable section-specific audio signature being identifiable from the at least one audio recording.

5. The system of claim 4, wherein, the plurality of different sections comprises any one or more of a launching section, a straight section, a bend section, a welded section, a flange section, a valve section, a regulator section, an actuator section, a rising section, a falling section, and a receiving section.

6. The system of claim 1, wherein the sensor device comprises an outer capsule including a first capsule portion and a second capsule portion that are joinable to enclose an interior compartment and provide fluid-tight containment to the interior compartment and that are separable to provide access to at least one predetermined location in the interior compartment for receiving a weight for adjusting the specific gravity of the sensor device.

7. The system of claim 6, wherein the system further comprises the weight for adjusting the specific gravity of the sensor device, the weight configured for insertion into the interior compartment at the predetermined location.

8. The system of claim 7, wherein the predetermined location is positioned such that the weight, when inserted into the interior compartment at the predetermined location, adjusts a center of mass of the sensor device to be different from a geometrical center of the sensor device.

9. The system of claim 6, wherein the predetermined location includes a groove for receiving and positioning the weight in the interior compartment.

10. The system of claim 9, wherein the groove for receiving and positioning the weight in the interior compartment is on an inner surface of the outer capsule.

11. A method for predicting presence of a leak in a fluid conduit carrying a first fluid, the method comprising:

sensing acoustic properties of the first fluid with a sensor device that flows freely along a path of the fluid conduit and storing the sensed acoustic properties as a first acoustic dataset, wherein the sensor device is transported with the flow of fluid directly and not required to ride on a surface of the fluid conduit, and wherein the sensor device has an adjustable specific gravity such that the specific gravity of the sensor device is adjustable to a first specific gravity for neutral buoyancy in the first fluid and to at least one other specific gravity for neutral buoyancy in a second fluid having a specific gravity different from a specific gravity of the first fluid, wherein the first specific gravity of the sensor device is constant as the sensor device freely flows with the first fluid;

after waiting a period of time, sensing acoustic properties of the first fluid with the sensor device along the same path and storing the sensed acoustic properties as a second acoustic dataset; and identifying a potential leak location in the fluid conduit by:

dissecting the first and second acoustic datasets into categorized and uncategorized regions, wherein a categorized region includes an audio signature that corresponds to a recognizable event during a data collection run;

comparing a first audio spectrum of the uncategorized regions of the first acoustic dataset with a second audio spectrum of the uncategorized regions of the second acoustic dataset, wherein each of the first and second audio spectrums include a plurality of frequency or amplitude values associated with time values indicating when the respective frequency or amplitude values were recorded relative to one another;

detecting an unambiguous audio signal in the second audio recording that is not present in the first audio recording by detecting any one or more of (i) changes in presence of intense spikes between corresponding uncategorized regions in the first and second audio spectrums, (ii) changes in frequency patterns between corresponding uncategorized regions in a first frequency spectrum of the first audio spectrum and a second frequency spectrum of the second audio spectrum, and (iii) changes in amplitude patterns between corresponding uncategorized regions in a first amplitude spectrum of the first audio spectrum and a second amplitude spectrum of the second audio spectrum; and identifying a location in the fluid conduit at which the unambiguous audio signal was recorded as the potential leak location using time data associated with the second acoustic dataset.

12. The method of claim 11 further comprising connecting the sensor device to an external device for providing the external device with the first acoustic dataset and the second acoustic dataset and performing the comparison of the first acoustic dataset with the second acoustic dataset for determining the presence of the leak in the fluid conduit on the external device.

13. The method of claim 12 wherein the determination of the presence of the leak in the fluid conduit on the external device comprises: comparing the first acoustic dataset with the second acoustic dataset; identifying differences between the first acoustic dataset and the second acoustic dataset; determining whether the differences are attributable to the presence of the leak within the fluid conduit by listening to audio recording corresponding to the differences.

* * * * *